US008927281B2

(12) United States Patent
Boitano et al.

(10) Patent No.: US 8,927,281 B2
(45) Date of Patent: Jan. 6, 2015

(54) METHOD FOR EXPANDING HEMATOPOIETIC STEM CELLS

(75) Inventors: Anthony E. Boitano, San Diego, CA (US); Michael Cooke, San Diego, CA (US); Shifeng Pan, San Diego, CA (US); Peter G. Schultz, La Jolla, CA (US); John Tellew, La Jolla, CA (US); Yongqin Wan, Irvine, CA (US); Xing Wang, San Diego, CA (US)

(73) Assignees: IRM LLC, Hamilton (BM); The Scripps Research Institute, La Jolla, CA (US)

( * ) Notice: Subject to any disclaimer, the term of this patent is extended or adjusted under 35 U.S.C. 154(b) by 1018 days.

(21) Appl. No.: 12/608,946

(22) Filed: Oct. 29, 2009

(65) Prior Publication Data

US 2010/0183564 A1 Jul. 22, 2010

Related U.S. Application Data

(60) Provisional application No. 61/109,821, filed on Oct. 30, 2008, provisional application No. 61/242,765, filed on Sep. 15, 2009.

(51) Int. Cl.
*C12N 5/00* (2006.01)
*C12N 5/0789* (2010.01)
*C07D 487/04* (2006.01)
*C07D 473/34* (2006.01)
*C07D 473/16* (2006.01)
*A61K 38/00* (2006.01)
*C07D 495/04* (2006.01)

(52) U.S. Cl.
CPC .......... *C07D 473/34* (2013.01); *C12N 2501/38* (2013.01); *C12N 2501/60* (2013.01); *C12N 5/0647* (2013.01); *C07D 487/04* (2013.01); *C07D 473/16* (2013.01); *A61K 38/00* (2013.01); *C07D 495/04* (2013.01)
USPC ........... 435/384; 435/383; 435/366; 435/375; 435/377

(58) Field of Classification Search
CPC .............. A61K 2300/00; A61K 45/06; A61K 39/3955; A61K 39/39558; A61K 31/337; A61K 2039/505; A61K 31/282; A61K 31/517; A61K 31/519; A61K 31/7068; A61K 31/4745; A61K 31/513; A61K 31/138; A61K 31/4184; A61K 31/506; A61K 31/573
See application file for complete search history.

(56) References Cited

U.S. PATENT DOCUMENTS

| | | | |
|---|---|---|---|
| 5,117,830 A | 6/1992 | McAfee et al. | |
| 5,437,994 A | 8/1995 | Emerson et al. | |
| 7,282,201 B2 | 10/2007 | Miura et al. | |
| 7,957,909 B2 * | 6/2011 | Bevilacqua et al. | 702/19 |
| 2001/0020030 A1 | 9/2001 | Stewart et al. | |
| 2003/0054549 A1 * | 3/2003 | Takebe et al. | 435/366 |
| 2003/0139427 A1 | 7/2003 | Castelhano et al. | |
| 2004/0043394 A1 * | 3/2004 | Ohkawa | 435/6 |
| 2006/0281791 A1 | 12/2006 | Keating et al. | |
| 2007/0161582 A1 | 7/2007 | Mijikovic et al. | |
| 2007/0275984 A1 | 11/2007 | Imogai et al. | |

FOREIGN PATENT DOCUMENTS

| | | |
|---|---|---|
| CN | 1280187 A | 1/2001 |
| EP | 0082369 | 6/1983 |
| EP | 0682027 | 11/1995 |
| EP | 1724268 | 11/2006 |
| WO | WO9720842 | 6/1997 |
| WO | 0028987 A1 | 5/2000 |
| WO | 0035446 A1 | 6/2000 |
| WO | WO 00/44750 | 8/2000 |
| WO | 0066112 A1 | 11/2000 |
| WO | 0117349 A1 | 3/2001 |
| WO | 0121180 A1 | 3/2001 |
| WO | 0134585 A1 | 5/2001 |
| WO | 0139773 A1 | 6/2001 |
| WO | WO0144260 | 6/2001 |
| WO | WO0149688 | 7/2001 |
| WO | 0189457 A2 | 11/2001 |
| WO | 0249413 A2 | 6/2002 |
| WO | 02085343 A1 | 10/2002 |
| WO | WO03031406 | 4/2003 |
| WO | 03103686 A1 | 12/2003 |
| WO | 2004054515 A2 | 7/2004 |
| WO | WO2005026164 | 3/2005 |
| WO | WO2005063258 | 7/2005 |
| WO | WO2006024174 | 3/2006 |
| WO | WO2006035061 | 4/2006 |
| WO | WO2006042949 | 4/2006 |

(Continued)

OTHER PUBLICATIONS

Biagi, et al., "erythro- and threo-2-Hydroxynonyl substituted 2-phenyladenines and 2-phenyl-8-azaadenines: ligands for A1 adenosine receptors and adenosine deaminase", Il Farmaco, 2002, pp. 221-233, vol. 57, Elsevier Science Ltd.

(Continued)

*Primary Examiner* — Blaine Lankford
(74) *Attorney, Agent, or Firm* — Chihang Amy Smith; Genomics Institute of the Novartis Research Foundation

(57) ABSTRACT

The present invention relates to compounds and compositions for expanding the number of CD34+ cells for transplantation. The invention further relates to a cell population comprising expanded hematopoietic stem cells (HSCs) and its use in autologous or allogeneic transplantation for the treatment of patients with inherited immunodeficient and autoimmune diseases and diverse hematopoietic disorders to reconstitute the hematopoietic cell lineages and immune system defense.

22 Claims, 13 Drawing Sheets

(56) References Cited

FOREIGN PATENT DOCUMENTS

| WO | WO2006061380 | 6/2006 |
| WO | 2007009120 A2 | 1/2007 |
| WO | 2007022269 A2 | 2/2007 |
| WO | 2007145227 A1 | 12/2007 |
| WO | 2008028645 A1 | 3/2008 |
| WO | WO2008051502 | 5/2008 |
| WO | 2008073748 A1 | 6/2008 |
| WO | WO2008116909 | 10/2008 |
| WO | WO2008116910 | 10/2008 |
| WO | WO2009097446 | 8/2009 |

OTHER PUBLICATIONS

Brun, et al., "Traceless solid-phase synthesis of 2,6,9-trisubstituted purines from resin bound 6-thiopurines", Tetrahedron, 2002, pp. 7911-7923, vol. 58, Elsevier Science Ltd.

Ding, et al., "Expanding the diversity of purine libraries", Tetrahedron Letters, 2001, pp. 8751-8755, vol. 42, Elsevier Science Ltd.

Giorgi, eta l., "N6-1,3-Diphenylurea derivatives of 2-phenyl-9-benzyladenines and 8-azaadenines: Synthesis and biological evaluation as allosteric modulators of A2A adenosine receptors", European Journal of Medicinal Chemistry, 2008, pp. 1639-1647, vol. 43, Elsevier Science Ltd.

Oumata, et al., "Roscovitine-Drived, Dual Specificity Inhibitors of Cyclin-Dependent Kinases and Casein Kinases 1", J. Med. Chem., 2008, pp. 5229-5242, vol. 51, American Chemical Society.

Vandromme, et al., "Suzuki-type Pd(0) coupling reactions in the synthesis of 2-arylpurines as Cdk inhibitors", "Bioorganic & medicinal Chemistry Letters", 2006, pp. 3144-3146, vol. 16, Elsevier Science Ltd.

Wan, et al., "N-Phenyl-N-purin-6-yl Ureas: The Design and Synthesis of p38a MAP Kinase Inhibitors", Bioorganic & Medicinal Chemistry Letters, 2003, pp. 1191-1194, vol. 13, No. 6, Elsevier Science Ltd.

Singh, et al., "The aryl hydrocarbon receptor has a normal function in the regulation of hematopoietic and other stem/progenitor cell populations", Biochemical Pharmacology, 2009, pp. 577-587, vol. 77, Elsevier, Inc.

Singh, et al., "Treatment of mice with the Ah receptor agonist and human carcinogen dioxin results in altered numbers and function of hematopoietic stem cells", Carinogenesis, 2009, pp. 11-19, vol. 3, No. 1, Oxford University Press.

CAS Registry No. 1031948-62-5, Entry Date Jul. 1, 2008, American Chemical Society.

Frericks, et al., "Microarray analysis of the AHR system: Tissue-specific flexibility in signal and target genes", Toxicology and Applied Pharmacology, 2007, pp. 320-332, vol. 220, No. 3.

"Thomas' Hematopoietic Cell Transplantation", Karl G. Blume, Stephen J. Forman, Frederik R. Applebaum (Eds.), Apr. 2008, Wiley-Blackwell.

Hannum, et al., "Ligand for FLT3/FLK2 receptor tyrosine kinase regulates growth of haematopoietic stem cells and is encoded by variant RNAs", Letters to Nature, Apr. 14, 1994, pp. 643-648, vol. 368, Nature Publishing Group.

Kaushansky, "Lineage-Specific Hematopoietic Growth Factors", The New England Journal of Medicine, May 11, 2006, pp. 2034-2045, vol. 354, No. 9, Massachusetts Medical Society.

Kishimoto, "Interleukin-6: From Basic Science to Medicine—40 Years in Immunology", Annu. Rev. Immunol., 2005, pp. 1-21; vol. 23, Annual Reviews.

Pearce, et al., "Interaction of the Aryl Hydrocarbon Receptor Ligand 6-Methyl-1,3,8-trichlorodibenzofuran with Estrogen Receptor a", Cancer Research, Apr. 15, 2004, pp. 2889-2897, vol. 64, American Association for Cancer Research.

Saulnier, et al., "An Efficient Method for the Synthesis of Guanidino Prodrugs", Bioorganic & Medicinal Chemistry Letters, 1994, pp. 1985-1990, vol. 4, No. 16, Elsevier Science Ltd.

Savouret, et al., "The aryl hydrocarbon receptor and its xenobiotic ligands: a fundamental trigger for cardiovascular disease", Nutr Metab Cardiovas Dis, 2003, pp. 104-113, vol. 13.

Smith, et al., "Stem Cell Factor: Biology and Relevance to Clinical Practice", Acta Haematol., 2001, pp. 143-150, vol. 105, S. Karger AG, Basel.

Zatloukalova, et al., "B-Naphthoflavone and 3'-methoxy-4'-nitroflavone exert ambiguous effects on Ah receptor-dependent cell proliferation and gene expression in rat liver 'stem-like' cells", Biochemical PHarmacology, 2007, pp. 1622-1634, vol. 73, Elsevier Inc.

* cited by examiner

Fig 1 Free molecule (no salt) Example 1 PXRD
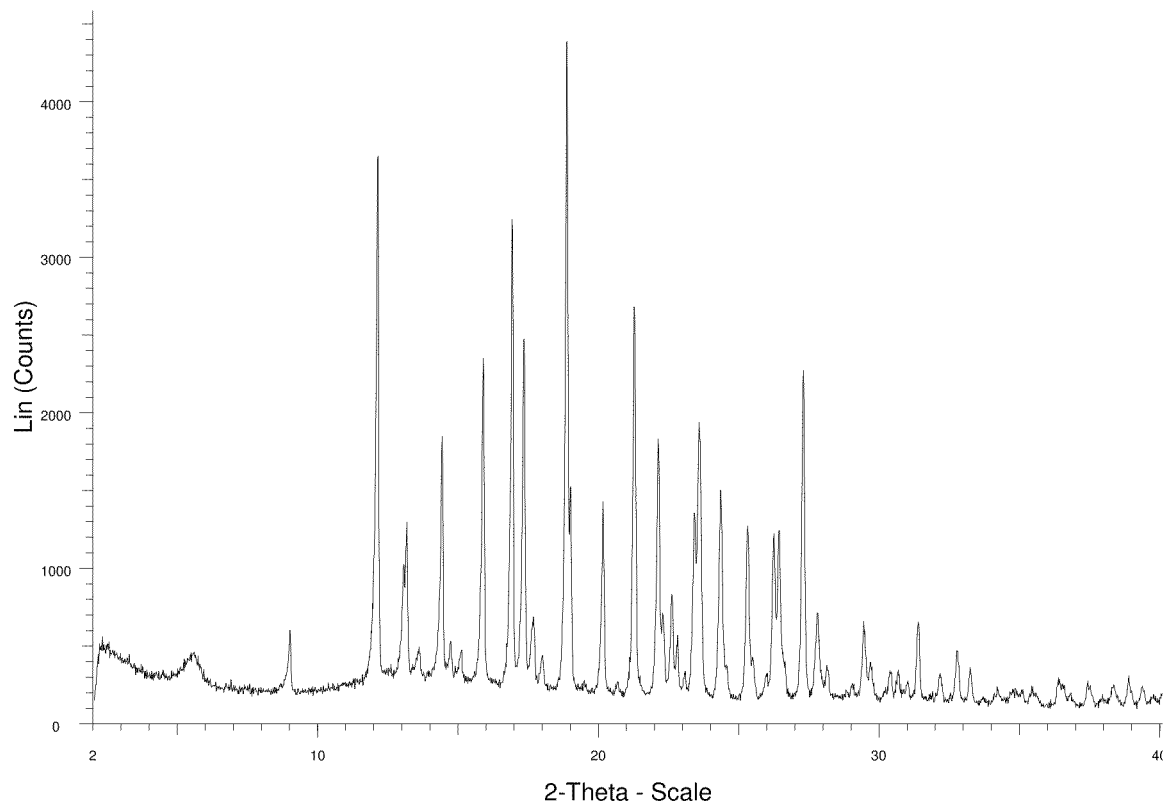

Fig 2 Example 1 nitrate salt PXRD
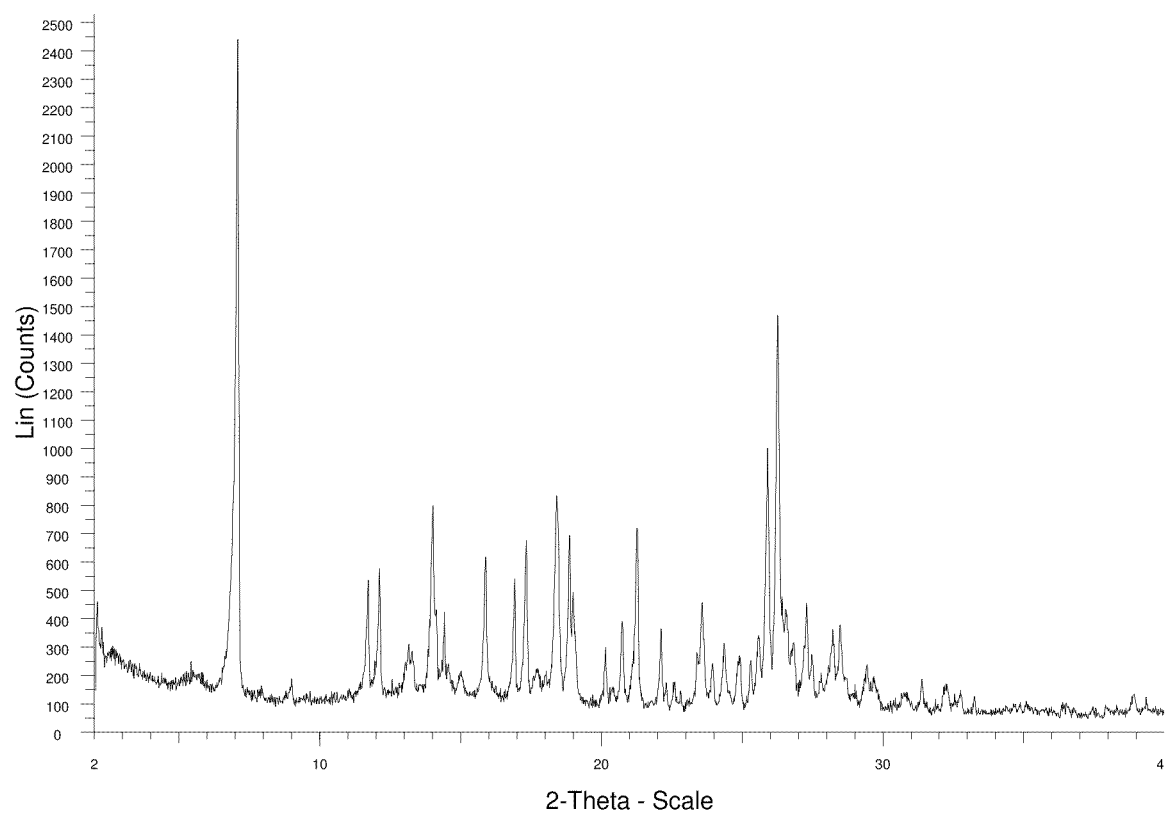

Figure 3 Example 1 mesylate salt PXRD
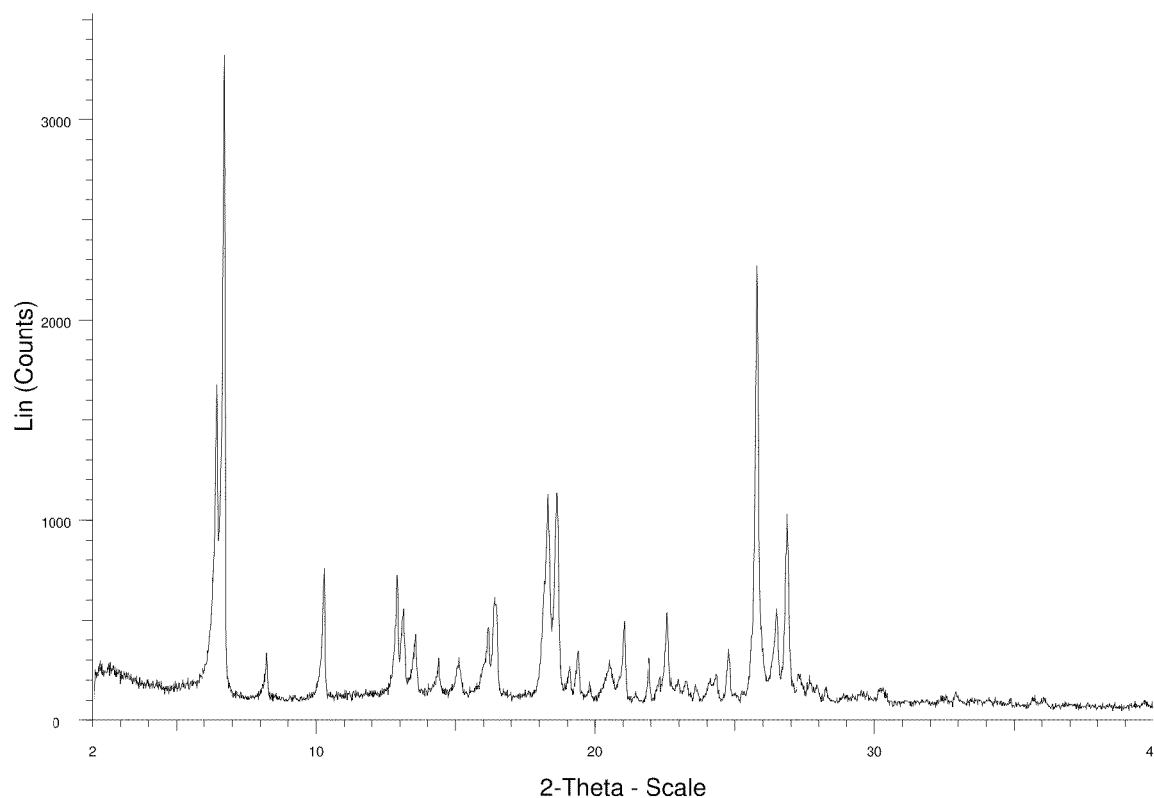

Figure 4 Example 1 tosylate salt PXRD
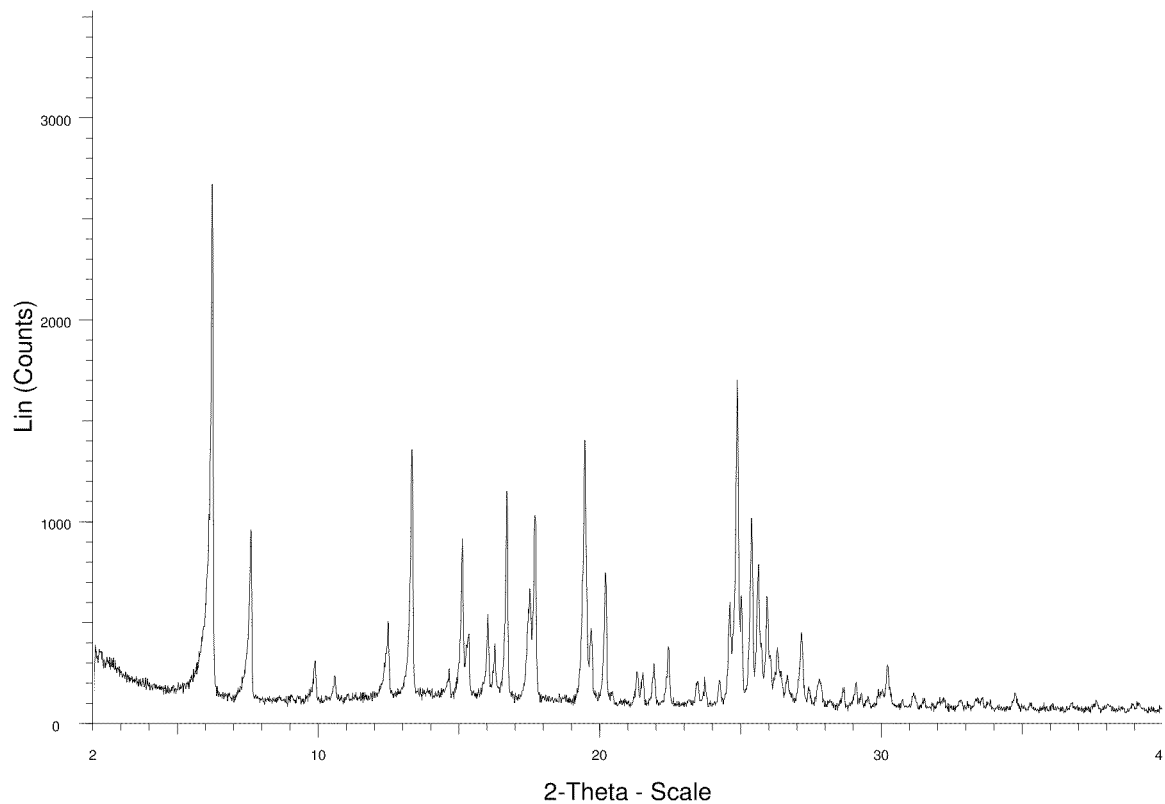

Figure 5 Example 1 hydrochloride salt PXRD
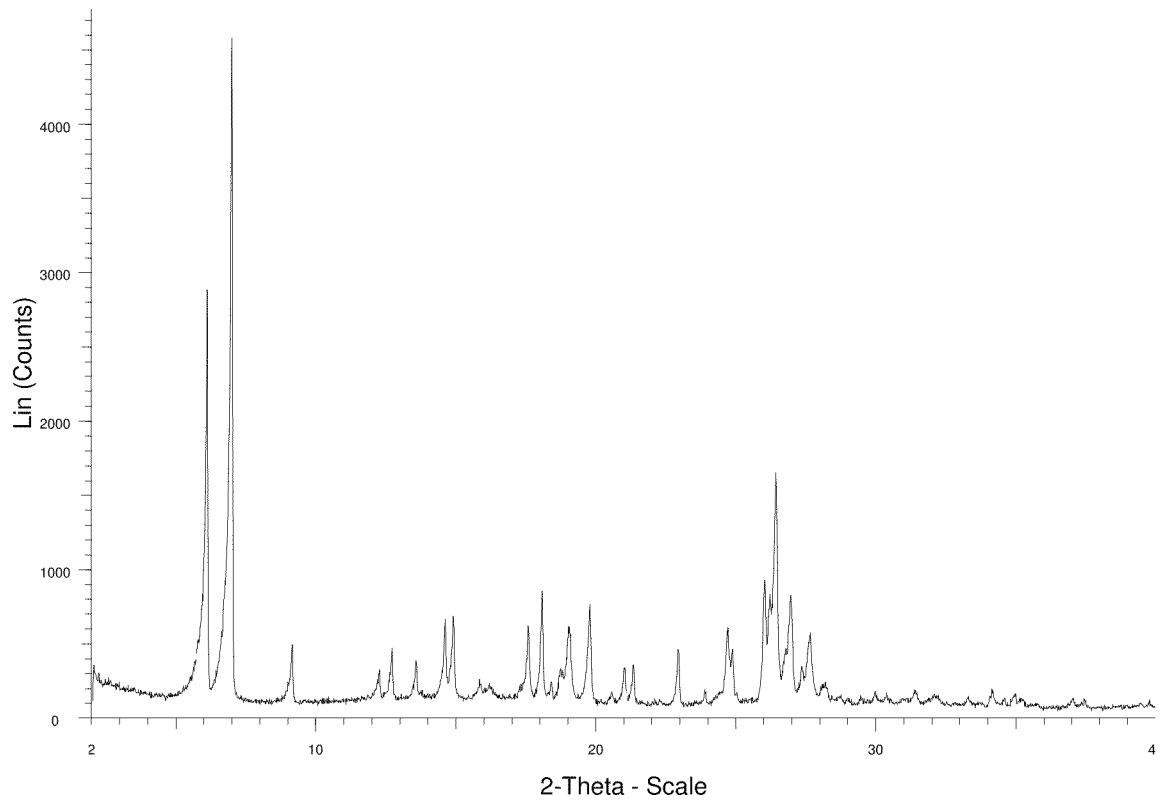

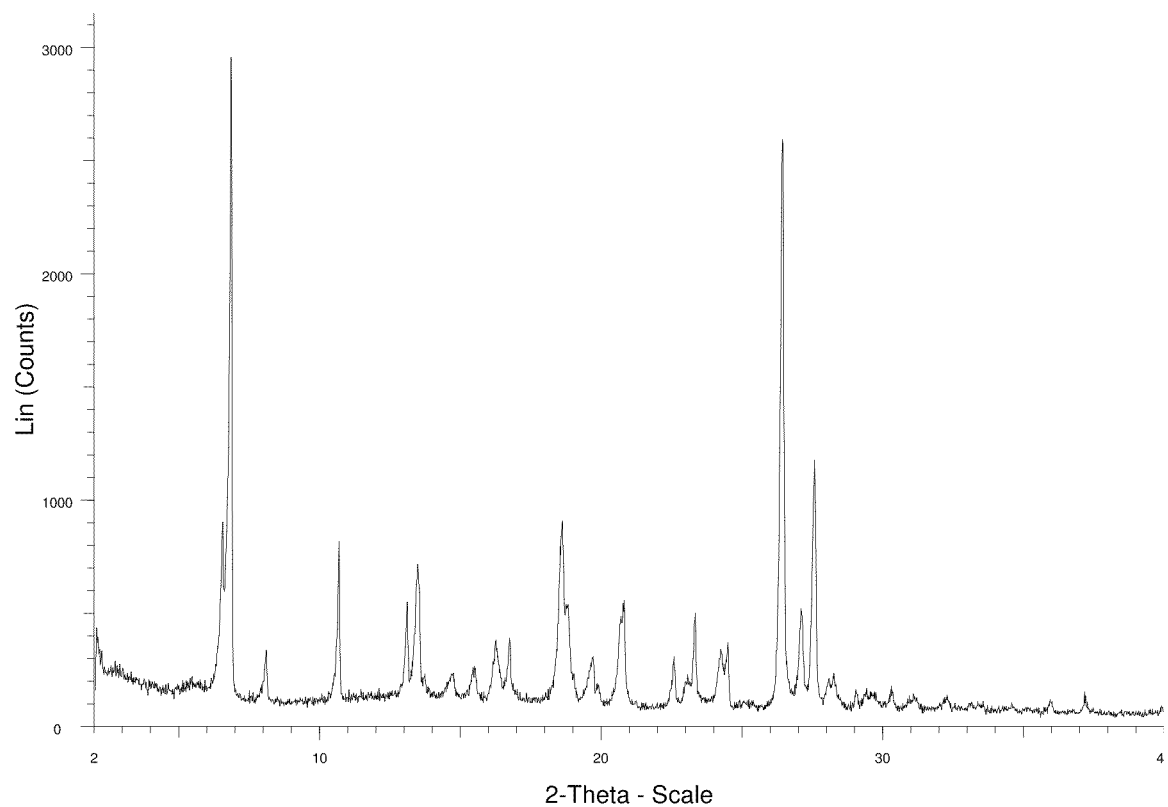
Figure 6  Example 1 sulphate salt PXRD

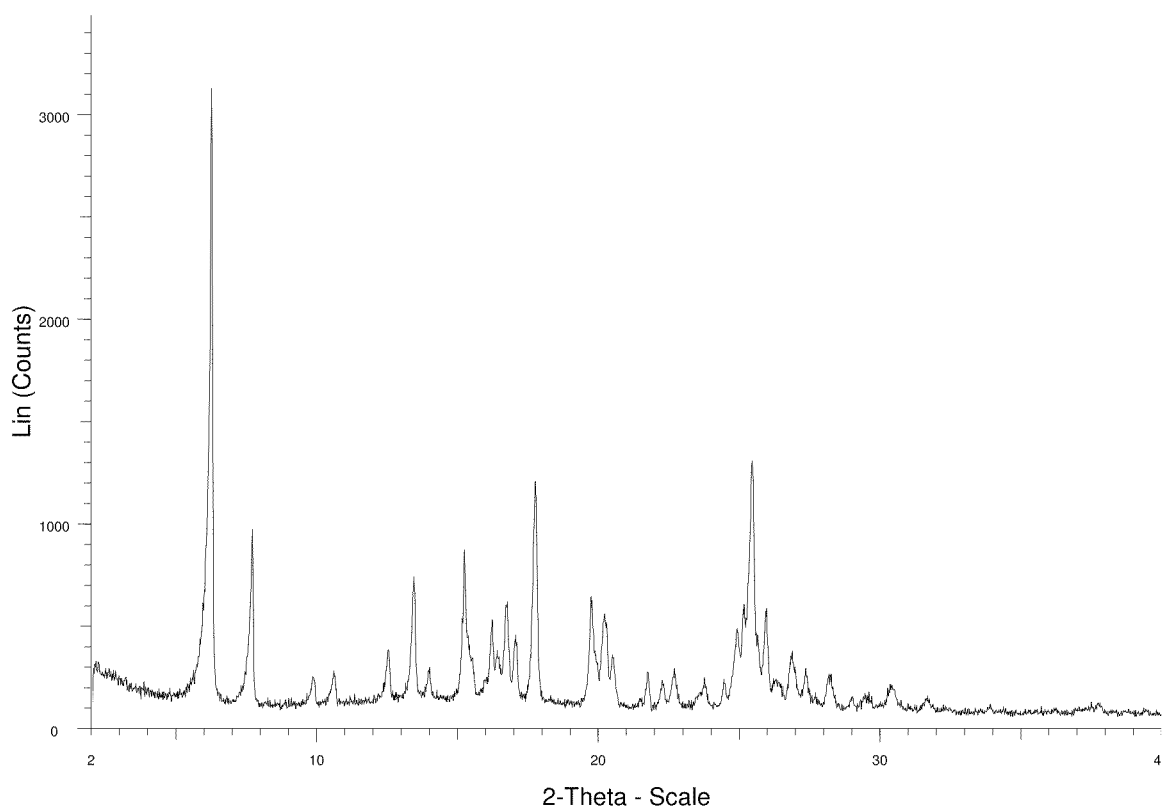
Figure 7 Example 1 besylate salt PXRD

Figure 8 Example 1 esylate salt PXRD
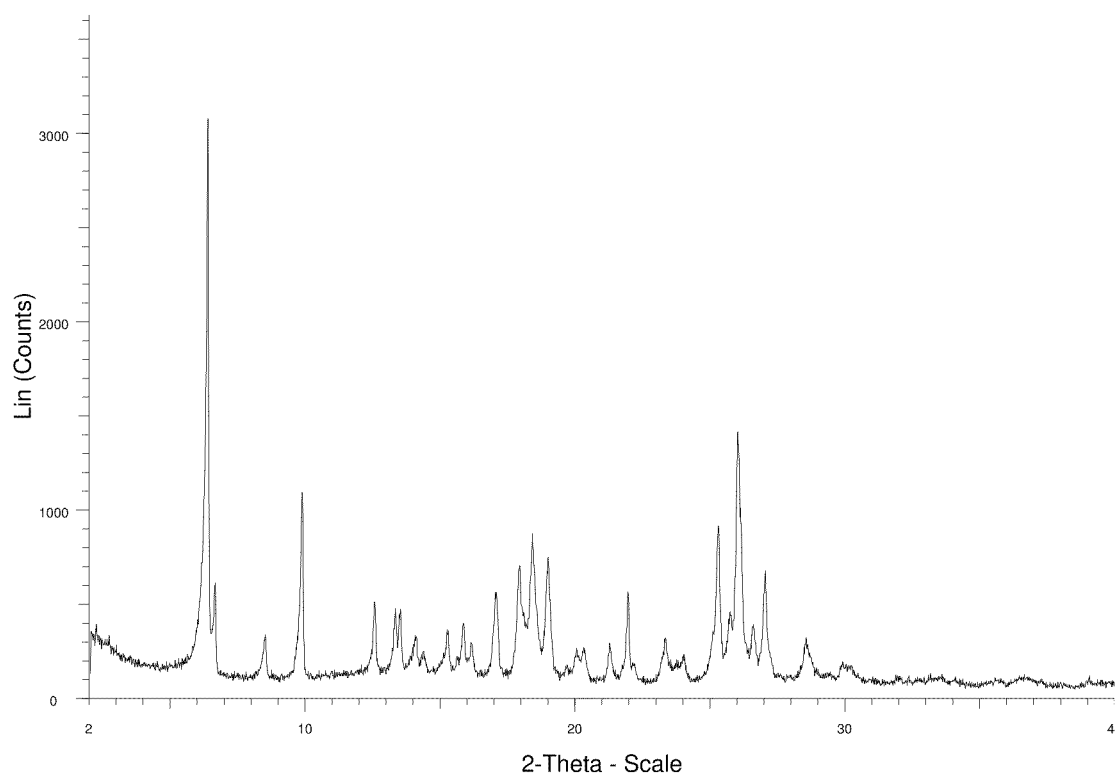

Figure 9 Example 1 hydrobromide salt PXRD
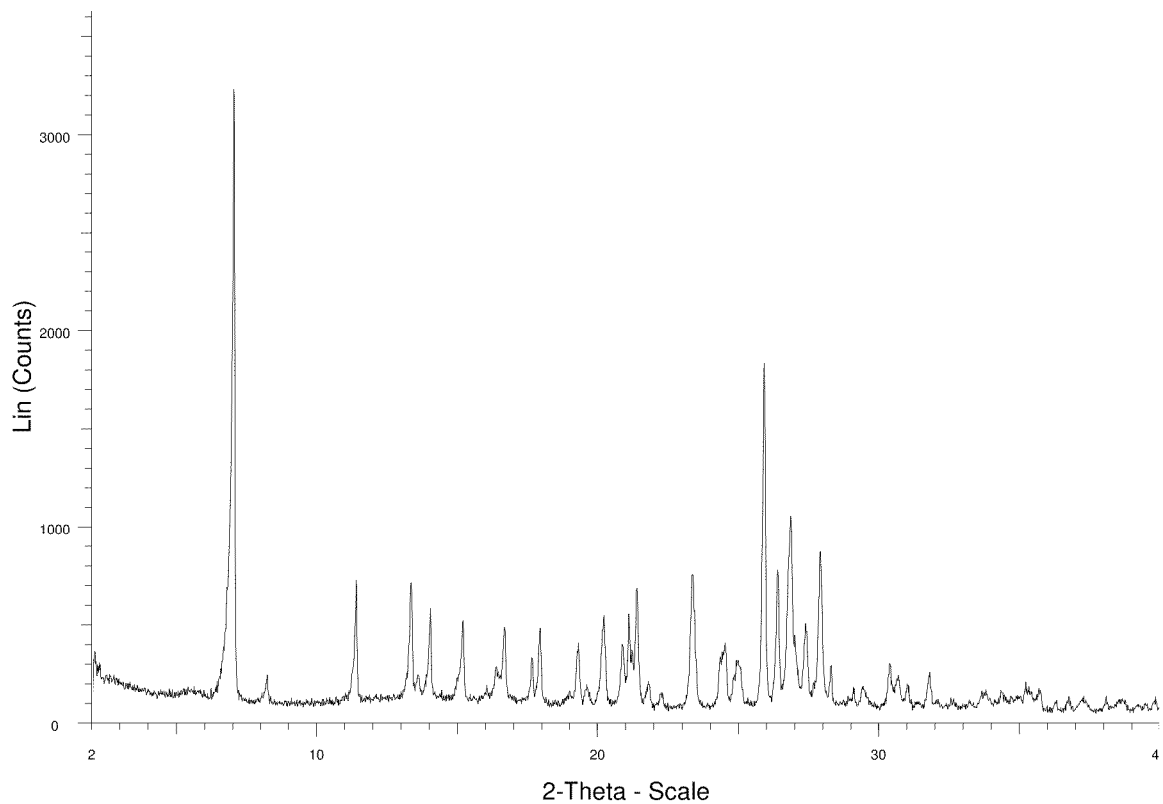

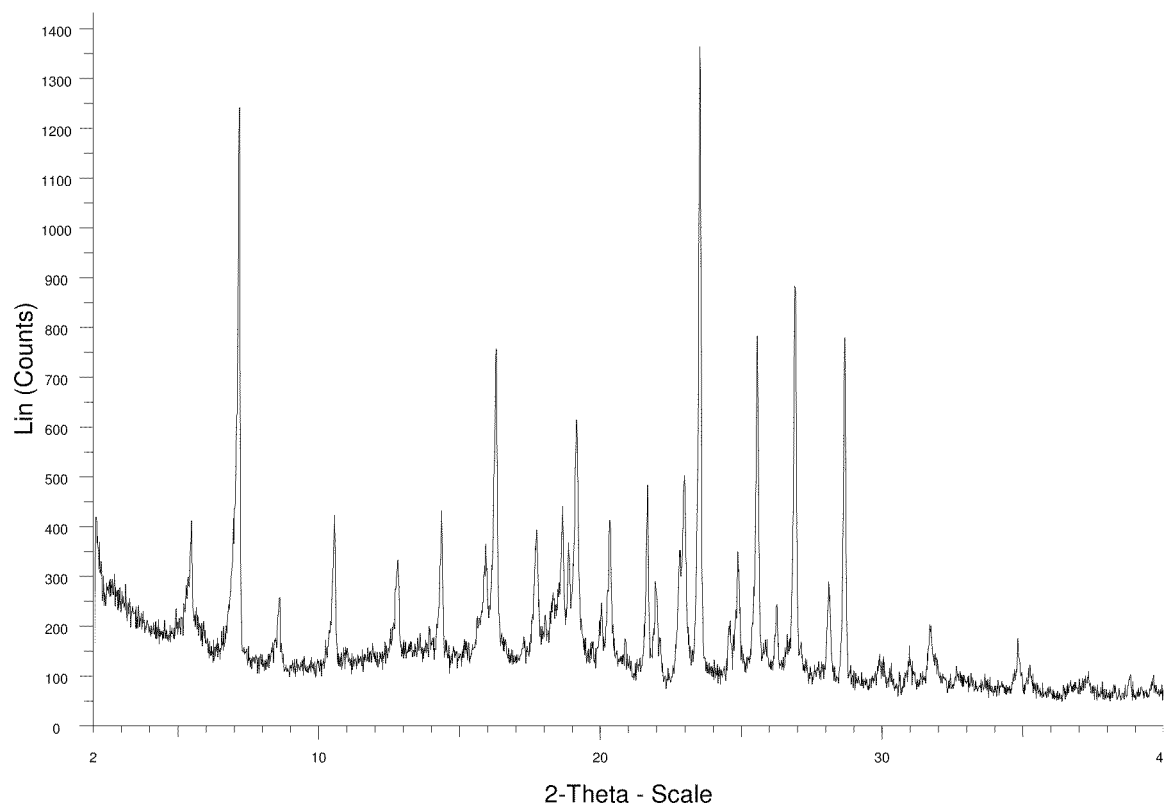
Figure 10 Example 1 orotate salt PXRD

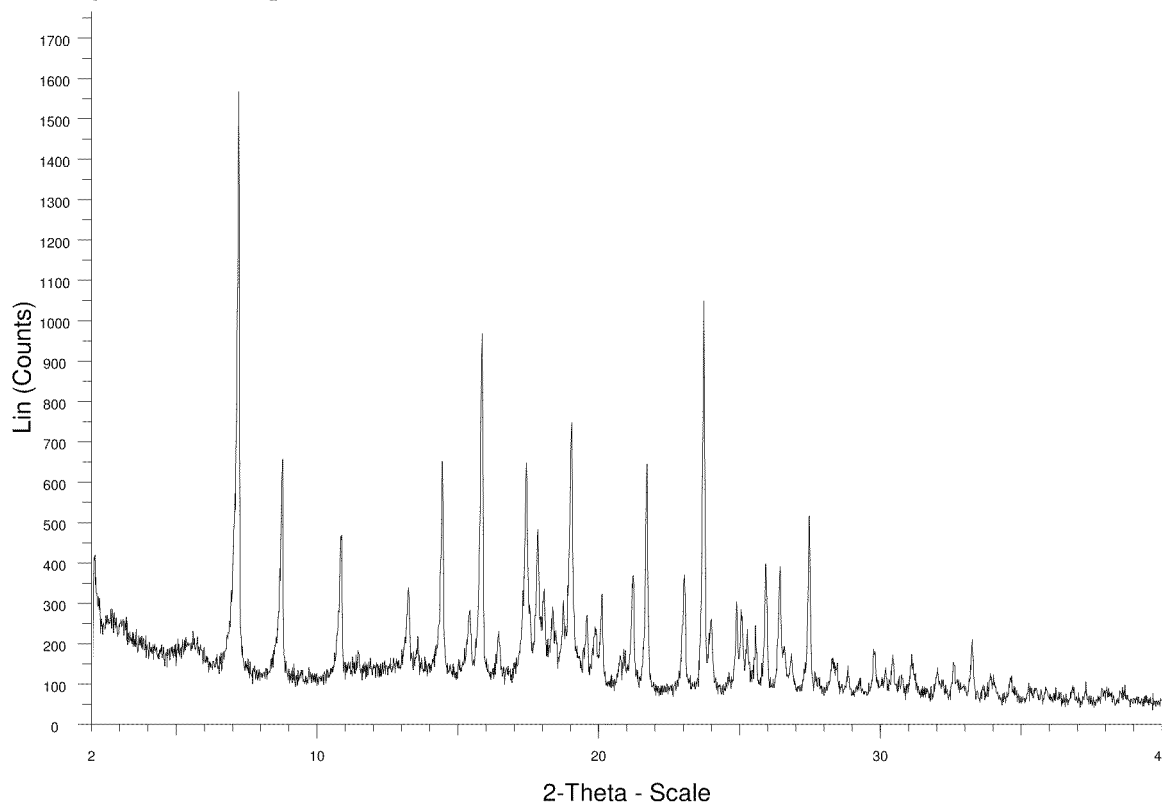
Figure 11 Example 1 Fumarate salt PXRD

Figure 12 Example 1 Napadysilate salt PXRD
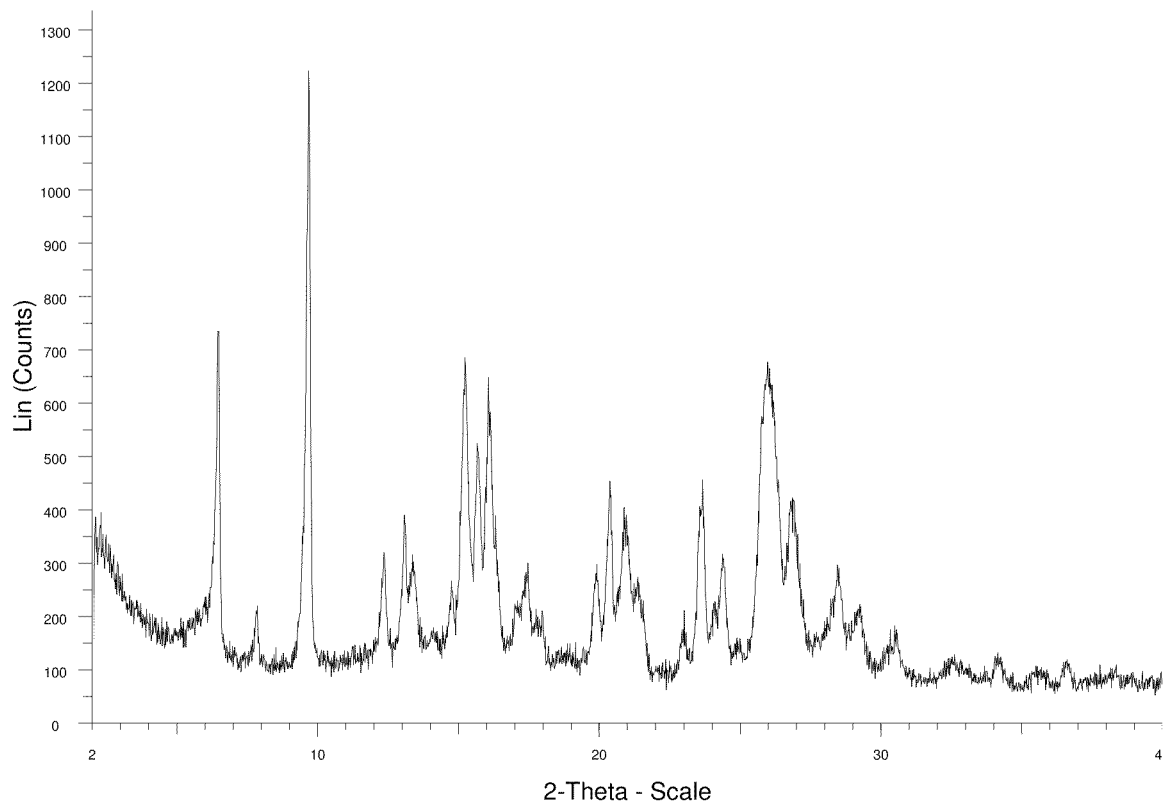

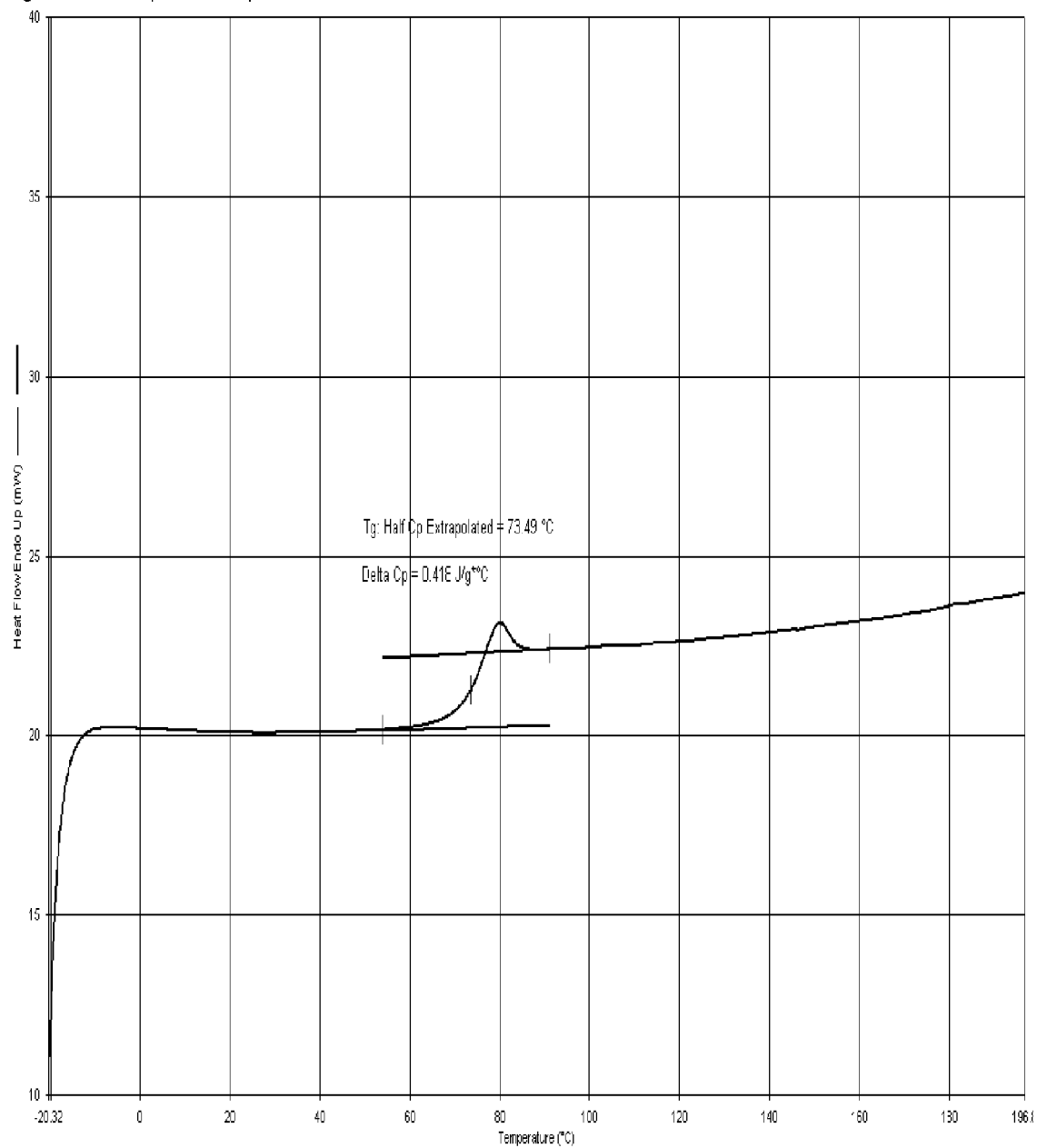
Figure 13 Example 1 amorphous material

```
                          SEQUENCE LISTING

<160> NUMBER OF SEQ ID NOS: 4

<210> SEQ ID NO 1
<211> LENGTH: 61
<212> TYPE: DNA
<213> ORGANISM: Homo sapiens

<400> SEQUENCE: 1
gcggcataga gaccgactta atttcaagag aattaagtcg gtctctatgc cgcttttttg     60
g                                                                    61

<210> SEQ ID NO 2
<211> LENGTH: 65
<212> TYPE: DNA
<213> ORGANISM: Homo sapiens

<400> SEQUENCE: 2
cgcgccaaaa aagcggcata gagaccgact taattctctt gaaattaagt cggtctctat    60
gccgc                                                                65

<210> SEQ ID NO 3
<211> LENGTH: 61
<212> TYPE: DNA
<213> ORGANISM: Homo sapiens

<400> SEQUENCE: 3
ggcttctttg atgttgcatt aattcaagag attaatgcaa catcaaagaa gccttttttg    60
g                                                                    61

<210> SEQ ID NO 4
<211> LENGTH: 65
<212> TYPE: DNA
<213> ORGANISM: Homo sapiens

<400> SEQUENCE: 4
cgcgccaaaa aaggcttctt tgatgttgca ttaatctctt gaattaatgc aacatcaaag    60
aagcc                                                                65
```

METHOD FOR EXPANDING HEMATOPOIETIC STEM CELLS

CROSS-REFERENCED TO RELATED APPLICATIONS

This application claims the benefit of priority to U.S. Provisional Patent Application No. 61/109,821, filed 30 Oct. 2008 and U.S. Provisional Patent Application No. 61/242,765, filed 15 Sep. 2009. The full disclosures of these applications are incorporated herein by reference in their entirety and for all purposes.

BACKGROUND OF THE INVENTION

1. Field of the Invention

The present invention relates to compounds and compositions for expanding the number of CD34+ cells for transplantation. The invention further relates to a cell population comprising expanded hematopoietic stem cells (HSCs) and its use in autologous or allogeneic transplantation for the treatment of patients with inherited immunodeficient and autoimmune diseases and diverse hematopoietic disorders to reconstitute the hematopoietic cell lineages and immune system defense.

2. Background

Hematopoietic stem cells (HSCs) are capable of regenerating all blood products throughout the life of an individual, balancing their self-renewal with progeny differentiation. Hematopoietic stem cells have therapeutic potential as a result of their capacity to restore blood and immune cells in transplant recipients. Furthermore, HSCs have the potential to generate cells for other tissues such as brain, muscle and liver. Human autologous and allogeneic bone marrow transplantation methods are currently used as therapies for leukemia, lymphoma, and other life-threatening diseases. For these procedures, a large number of stem cells must be isolated to ensure that there are enough HSCs for engraftment. The number of HSCs available for treatment is a clinical limitation.

The present invention relates to compounds and compositions for expanding hematopoietic stem cell populations and uses thereof.

SUMMARY OF THE INVENTION

In one aspect, the present invention provides a compound of Formula I:

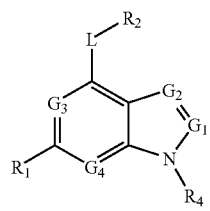

in which:

$G_1$ is selected from N and $CR_3$;

$G_2$, $G_3$ and $G_4$ are independently selected from CH and N; with the proviso that at least 1 of G3 and G4 is N; with the proviso that $G_1$ and $G_2$ are not both N;

L is selected from —$NR_{5a}(CH_2)_{0-3}$— (0-3 herein means 0, 1, 2 or 3), —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—; wherein $R_{5a}$ and $R_{5b}$ are independently selected from hydrogen and $C_{1-4}$alkyl;

$R_1$ is selected from hydrogen, phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl; wherein said phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl or thiazolyl of $R_1$ can be optionally substituted by 1 to 3 radicals independently selected from cyano, hydroxy, $C_{1-4}$alkyl, $C_{1-4}$alkoxy, halo, halo-substituted-$C_{1-4}$alkyl, halo-substituted-$C_{1-4}$alkoxy, hydroxy, amino, —$C(O)R_{8a}$, —$S(O)_{0-2}R_{8a}$, —$C(O)OR_{8a}$ and —$C(O)NR_{8a}R_{8b}$; wherein $R_{8a}$ and $R_{8b}$ are independently selected from hydrogen and $C_{1-4}$alkyl; with the proviso that $R_1$ and $R_3$ are not both hydrogen;

$R_2$ is selected from —$S(O)_2NR_{6a}R_{6b}$, —$NR_{9a}C(O)R_{9b}$, —$NR_{6a}C(O)NR_{6b}R_{6c}$, phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl; wherein $R_{6a}$, $R_{6b}$ and $R_{6c}$ are independently selected from hydrogen and $C_{1-4}$alkyl; wherein said phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl or 1H-indazolyl of $R_2$ is optionally substituted with 1 to 3 radicals independently selected from hydroxy, halo, methyl, methoxy, amino, —$O(CH_2)_nNR_{7a}R_{7b}$, —$S(O)_2NR_{7a}R_{7b}$, —$OS(O)_2NR_{7a}R_{7b}$ and —$NR_{7a}S(O)_2R_{7b}$; wherein $R_{7a}$ and $R_{7b}$ are independently selected from hydrogen and $C_{1-4}$alkyl;

$R_3$ is selected from hydrogen, $C_{1-4}$alkyl and biphenyl; and $R_4$ is selected from $C_{1-10}$alkyl, prop-1-en-2-yl, cyclohexyl, cyclopropyl, 2-(2-oxopyrrolidin-1-yl)ethyl, oxetan-3-yl, benzhydryl, tetrahydro-2H-pyran-3-yl, tetrahydro-2H-pyran-4-yl, phenyl, tetrahydrofuran-3-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said alkyl, cyclopropyl, cyclohexyl, 2-(2-oxopyrrolidin-1-yl)ethyl, oxetan-3-yl, oxetan-2-yl, benzhydryl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl) ethyl can be optionally substituted with 1 to 3 radicals independently selected from hydroxy, $C_{1-4}$alkyl and halo-substituted-$C_{1-4}$alkyl; or the N-oxide derivatives, prodrug derivatives, protected derivatives, individual isomers and mixture of isomers thereof; or the salts (preferably the pharmaceutically acceptable salts) and solvates (e.g. hydrates) of such compounds.

BRIEF DESCRIPTION OF DRAWINGS

FIG. 1 discloses the PXRD pattern of solid form modification A of 4-(2-(2-(benzo[b]thiophen-3-yl)-9-isopropyl-9H-purin-6-ylamino)ethyl)phenol.

FIGS. 2 to 12 disclose the PXRD patterns of solid forms of 4-(2-(2-(benzo[b]thiophen-3-yl)-9-isopropyl-9H-purin-6-ylamino)ethyl)phenol salts, respectively the nitrate, mesylate, tosylate, hydrochloride, sulphate, besylate, esylate, hydrobromide, orotate, fumarate and napadysilate salts.

FIG. 13 discloses the DSC pattern of the amorphous form of 4-(2-(2-(benzo[b]thiophen-3-yl)-9-isopropyl-9H-purin-6-ylamino)ethyl)phenol.

DETAILED DESCRIPTION OF THE INVENTION

Definitions

"Alkyl" as a group and as a structural element of other groups, for example halo-substituted-alkyl and alkoxy, can be either straight-chained or branched. For example, alkyl includes methyl, ethyl, propyl, isopropyl, butyl, isobutyl, sec-butyl, t-butyl, etc. $C_{1-4}$-alkoxy includes methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl where one or more of the ring members are a heteroatom or moiety selected from —O—, —N=, —NR—, —C(O)—, —S—, —S(O)— or —S(O)$_2$—, wherein R is hydrogen, $C_{1-4}$alkyl or a nitrogen protecting group. For example heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 2-Oxo-pyrrolidin-1-yl, 1,4-dioxa-8-aza-spiro[4.5]dec-8-yl, etc.

"Halogen" (or halo) preferably represents chloro or fluoro, but may also be bromo or iodo.

"Hematopoietic stem cells" (HSCs) as used herein refer to immature blood cells having the capacity to self-renew and to differentiate into more mature blood cells comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages). HSCs are interchangeably described as stem cells throughout the specification. It is known in the art that such cells may or may not include CD34$^+$ cells. CD34$^+$ cells are immature cells that express the CD34 cell surface marker. CD34+ cells are believed to include a subpopulation of cells with the stem cell properties defined above. It is well known in the art that HSCs include pluripotent stem cells, multipotent stem cells (e.g., a lymphoid stem cell), and/or stem cells committed to specific hematopoietic lineages. The stem cells committed to specific hematopoietic lineages may be of T cell lineage, B cell lineage, dendritic cell lineage, Langerhans cell lineage and/or lymphoid tissue-specific macrophage cell lineage. In addition, HSCs also refer to long term HSC (LT-HSC) and short term HSC (ST-HSC). ST-HSCs are more active and more proliferative than LT-HSCs. However, LT-HSC have unlimited self renewal (i.e., they survive throughout adulthood), whereas ST-HSC have limited self renewal (i.e., they survive for only a limited period of time). Any of these HSCs can be used in any of the methods described herein. Optionally, ST-HSCs are useful because they are highly proliferative and thus, quickly increase the number of HSCs and their progeny. Hematopoietic stem cells are optionally obtained from blood products. A blood product includes a product obtained from the body or an organ of the body containing cells of hematopoietic origin. Such sources include un-fractionated bone marrow, umbilical cord, peripheral blood, liver, thymus, lymph and spleen. All of the aforementioned crude or un-fractionated blood products can be enriched for cells having hematopoietic stem cell characteristics in ways known to those of skill in the art.

"Treat", "treating" and "treatment" refer to a method of alleviating or abating a disease and/or its attendant symptoms.

"Expansion" in the context of cells refers to increase in the number of a characteristic cell type, or cell types, from an initial cell population of cells, which may or may not be identical. The initial cells used for expansion may not be the same as the cells generated from expansion.

"Cell population" refers to eukaryotic mammalian, preferably human, cells isolated from biological sources, for example, blood product or tissues and derived from more than one cell.

"Enriched" when used in the context of cell population refers to a cell population selected based on the presence of one or more markers, for example, CD34+.

The term "CD34+ cells" refers to cells that express at their surface CD34 marker. CD34+ cells can be detected and counted using for example flow cytometry and fluorescently labeled anti-CD34 antibodies.

"Enriched in CD34+ cells" means that a cell population has been selected based on the presence of CD34 marker. Accordingly, the percentage of CD34+ cells in the cell population after selection method is higher than the percentage of CD34+ cells in the initial cell population before selecting step based on CD34 markers. For example, CD34+ cells may represent at least 50%, 60%, 70%, 80% or at least 90% of the cells in a cell population enriched in CD34+ cells.

"Cord blood unit" refers to the blood collected from umbilical cord of a single birth.

DESCRIPTION OF THE PREFERRED EMBODIMENTS

The present invention relates to methods and compositions for expanding HSC populations using an agent capable of down-regulating the activity and/or expression of aryl hydrocarbon receptor and/or a downstream effector of aryl hydrocarbon receptor pathway.

In one embodiment, said agent capable of down-regulating the activity and/or expression of aryl hydrocarbon receptor is a compound of Formula I.

In one embodiment, with reference to compounds of Formula I, are compounds selected from Formulae Ia, Ib, Ic, Id and Ie:

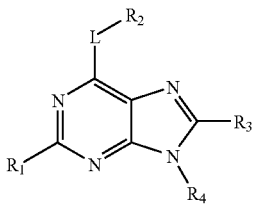

Ia

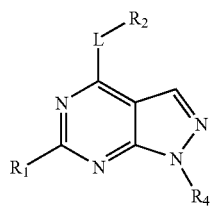

Ib

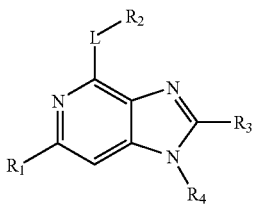

Ic

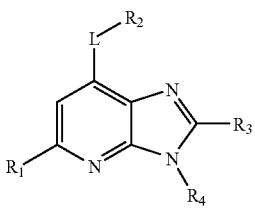

Id

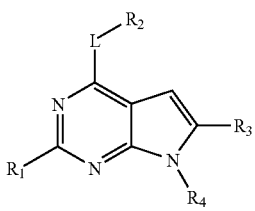

Ie in which:

L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH$_2$CH(OH)— and —NR$_{5a}$CH(CH$_3$)CH$_2$—; wherein R$_{5a}$ and R$_{5b}$ are independently selected from hydrogen and C$_{1-4}$alkyl; wherein the right side of the L moiety as shown is attached to R$_2$, for example: —NR$_{5a}$(CH$_2$)$_{0-3}$—R$_2$, —NR$_{5a}$CH(C(O)OCH$_3$)CH$_2$—R$_2$, —NR$_{5a}$(CH$_2$)$_2$NR$_{5b}$—R$_2$, —NR$_{5a}$(CH$_2$)$_2$S—R$_2$, —NR$_{5a}$CH$_2$CH(CH$_3$)CH$_2$—R$_2$, —NR$_{5a}$CH$_2$CH(OH)—R$_2$ and —NR$_{5a}$CH(CH$_3$)CH$_2$—R$_2$.

R$_1$ is selected from hydrogen, phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl;

wherein said phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl or thiazol-5-yl of R$_1$ can be optionally substituted by 1 to 3 radicals independently selected from cyano, hydroxy, C$_{1-4}$alkyl, C$_{1-4}$alkoxy, halo, halo-substituted-C$_{1-4}$alkyl, —S(O)$_{0-2}$R$_{8a}$ and —C(O)OR$_{8a}$; wherein R$_{8a}$ and R$_{8b}$ are independently selected from hydrogen and C$_{1-4}$alkyl; with the proviso that R$_1$ and R$_3$ are not both hydrogen;

R$_2$ is selected from —NR$_{6a}$C(O)NR$_{6b}$R$_{6c}$, phenyl, 1H-pyrrolo[2,3-b]pyridin-3-yl, 1H-pyrrolo[2,3-b]pyridin-5-yl, 1H-indol-3-yl, thiophen-3-yl, pyridin-2-yl, pyridin-3-yl, pyridin-4-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl and 1H-indazol-3-yl; wherein R$_{6a}$, R$_{6b}$ and R$_{6c}$ are independently selected from hydrogen and C$_{1-4}$alkyl; wherein said phenyl, 1H-pyrrolo[2,3-b]pyridin-3-yl, 1H-pyrrolo[2,3-b]pyridin-5-yl, 1H-indol-3-yl, thiophen-3-yl pyridin-2-yl, pyridin-3-yl, pyridin-4-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl or 1H-indazol-3-yl of R$_2$ is optionally substituted with 1 to 3 radicals independently selected from hydroxy, halo, methoxy, amino, —OS(O)$_2$NR$_{7a}$R$_{7b}$ and —NR$_{7a}$S(O)$_2$R$_{7b}$; wherein R$_{7a}$ and R$_{7b}$ are independently selected from hydrogen and C$_{1-4}$alkyl;

R$_3$ is selected from hydrogen, C$_{1-4}$alkyl and biphenyl; and

R$_4$ is selected from isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl, 2-(2-oxopyrrolidin-1-yl)ethyl, oxetan-3-yl, oxetan-2-yl, benzhydryl, tetrahydro-2H-pyran-2-yl, phenyl, tetrahydrofuran-3-yl and benzyl; wherein said cyclohexyl, 2-(2-oxopyrrolidin-1-yl)ethyl, oxetan-3-yl, oxetan-2-yl, benzhydryl, tetrahydro-2H-pyran-4-yl, phenyl, tetrahydrofuran-3-yl or benzyl can be optionally substituted with 1 to 3 radicals independently selected from C$_{1-4}$alkyl and halo-substituted-C$_{1-4}$alkyl.

In another embodiment, L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH(CH$_3$)CH$_2$— and —NR$_{5a}$CH$_2$CH(OH)—; wherein R$_{5a}$ and R$_{5b}$ are independently selected from hydrogen and methyl; and R$_1$ is selected from hydrogen, phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl; wherein said phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl or thiazol-5-yl of R$_1$ can be optionally substituted by 1 to 3 radicals independently selected from cyano, hydroxy, C$_{1-4}$alkyl, C$_{1-4}$alkoxy, halo, halo-substituted-C$_{1-4}$alkyl, —S(O)$_{0-2}$R$_{8a}$ and —C(O)OR$_{8a}$; wherein R$_{8a}$ and R$_{8b}$ are independently selected from hydrogen and C$_{1-4}$alkyl; with the proviso that R$_1$ and R$_3$ are not both hydrogen.

In another embodiment, when L is —NR$_{5a}$(CH$_2$)$_{0-3}$, it is preferably —NR$_{5a}$(CH$_2$)$_{1-3}$ (where 1-3 herein 1, 2 or 3).

In another embodiment, R$_2$ is selected from urea, phenyl, 1H-indol-2-yl, 1H-indol-3-yl, thiophen-3-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl, 1H-benzo[d]imidazol-5-yl and 1H-imidazol- 4-yl; wherein said phenyl, 1H-indol-2-yl, 1H-indol-3-yl, thiophen-3-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl or 1H-benzo[d]imidazol-5-yl of $R_2$ is optionally substituted with hydroxy, methoxy, methyl, halo, amino and amino-sulfonyl.

In another embodiment, $R_3$ is selected from hydrogen, methyl and biphenyl; and $R_4$ is selected from isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl, 2-(2-oxopyrrolidin-1-yl)ethyl, oxetan-3-yl, oxetan-2-yl, benzhydryl, tetrahydro-2H-pyran-2-yl, phenyl, tetrahydrofuran-3-yl and benzyl; wherein said cyclohexyl, 2-(2-oxopyrrolidin-1-yl)ethyl, oxetan-3-yl, oxetan-2-yl, benzhydryl, tetrahydro-2H-pyran-4-yl, phenyl, tetrahydrofuran-3-yl or benzyl can be optionally substituted with 1 to 3 radicals independently selected from methyl and trifluoromethyl.

In another embodiment are compounds selected from: 4-(2-(2-(benzo[b]thiophen-3-yl)-9-isopropyl-9H-purin-6-ylamino)ethyl)phenol; 4-(2-(2-(benzo[b]thiophen-3-yl)-9-sec-butyl-9H-purin-6-ylamino)ethyl)phenol; 4-(2-(9-benzhydryl-2-(benzo[b]thiophen-3-yl)-9H-purin-6-ylamino)ethyl)phenol; 4-(2-(2-(benzo[b]thiophen-3-yl)-9-(tetrahydro-2H-pyran-3-yl)-9H-purin-6-ylamino)ethyl)phenol; 4-(2-(9-isopropyl-2-(thiophen-2-yl)-9H-purin-6-ylamino)ethyl)phenol; 4-(2-(2-(benzo[b]thiophen-3-yl)-9-(4-(trifluoromethyl)benzyl)-9H-purin-6-ylamino)ethyl)phenol; 4-(2-(2-(benzo[b]thiophen-3-yl)-9-isobutyl-9H-purin-6-ylamino)ethyl)phenol; 4-(2-(2-(benzo[b]thiophen-3-yl)-9-methyl-9H-purin-6-ylamino)ethyl)phenol; 4-(2-(2-(benzo[b]thiophen-3-yl)-9-(4-methylbenzyl)-9H-purin-6-ylamino)ethyl)phenol; N-(2-(1H-indol-3-yl)ethyl)-2-(benzo[b]thiophen-3-yl)-9-isopropyl-9H-purin-6-amine; 2-(benzo[b]thiophen-3-yl)-9-isopropyl-N-(2-(thiophen-3-yl)ethyl)-9H-purin-6-amine; 3-(2-(2-(benzo[b]thiophen-3-yl)-9-isopropyl-9H-purin-6-ylamino)ethyl)phenol; 2-(benzo[b]thiophen-3-yl)-N-(4-fluorophenethyl)-9-isopropyl-9H-purin-6-amine; N-(4-aminophenethyl)-2-(benzo[b]thiophen-3-yl)-9-isopropyl-9H-purin-6-amine; 4-(2-(9-isopropyl-2-(pyrimidin-5-yl)-9H-purin-6-ylamino)ethyl)phenol; 4-(2-(9-isopropyl-2-(pyridin-3-yl)-9H-purin-6-ylamino)ethyl)phenol; 4-(2-(9-isopropyl-2-phenyl-9H-purin-6-ylamino)ethyl)phenol; 4-(2-(9-isopropyl-2-(thiophen-3-yl)-9H-purin-6-ylamino)ethyl)phenol; 4-(2-(2-(furan-3-yl)-9-isopropyl-9H-purin-6-ylamino)ethyl)phenol; 2-(benzo[b]thiophen-3-yl)-N-(4-fluorophenethyl)-9-phenyl-9H-purin-6-amine; N-benzyl-8-(biphenyl-4-yl)-9-isopropyl-9H-purin-6-amine; 4-(2-(2-(benzo[b]thiophen-3-yl)-9-(nonan-2-yl)-9H-purin-6-ylamino)ethyl)phenol; N-(2-(1H-indol-3-yl)ethyl)-2-(benzo[b]thiophen-3-yl)-9-sec-butyl-9H-purin-6-amine; 3-(2-(2-(benzo[b]thiophen-3-yl)-9-isopropyl-9H-purin-6-ylamino)ethyl)-1H-indol-5-yl, 5-((3aS,4S,6aR)-2-oxohexahydro-1H-thieno[3,4-d]imidazol-4-yl)pentanoate; N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide; 4-(2-(9-isopropyl-2-(pyridin-4-yl)-9H-purin-6-ylamino)ethyl)phenol; ethyl 5-(6-(4-hydroxyphenethylamino)-9-isopropyl-9H-purin-2-yl)nicotinate; ethyl 5-(6-(4-hydroxyphenethylamino)-9-isopropyl-9H-purin-2-yl)nicotinate; 4-(2-(2-(6-fluoropyridin-3-yl)-9-isopropyl-9H-purin-6-ylamino)ethyl)phenol; 4-(2-(9-isopropyl-2-(4-methylpyridin-3-yl)-9H-purin-6-ylamino)ethyl)phenol; 5-(6-(4-hydroxyphenethylamino)-9-isopropyl-9H-purin-2-yl)nicotinonitrile; 4-(2-(9-isopropyl-2-(pyrrolidin-1-yl)-9H-purin-6-ylamino)ethyl)phenol; 4-(2-(2-(1H-imidazol-1-yl)-9-isopropyl-9H-purin-6-ylamino)ethyl)phenol; 4-(2-(9-isopropyl-2-(pyridazin-4-yl)-9H-purin-6-ylamino)ethyl) phenol; 4-(2-(9-isopropyl-2-(pyrazin-2-yl)-9H-purin-6-ylamino)ethyl)phenol; 4-(2-(9-isopropyl-2-(pyridin-2-yl)-9H-purin-6-ylamino)ethyl)phenol; 4-(2-(9-isopropyl-2-(5-(methylsulfonyl)pyridin-3-yl)-9H-purin-6-ylamino)ethyl) phenol; 4-(2-(9-isopropyl-2-(5-methylpyridin-3-yl)-9H-purin-6-ylamino)ethyl)phenol; 4-(2-(2-(4-chloropyridin-3-yl)-9-isopropyl-9H-purin-6-ylamino)ethyl)phenol; 4-(2-(2-(5-fluoropyridin-3-yl)-9-isopropyl-9H-purin-6-ylamino) ethyl)phenol; 4-(2-(9-isopropyl-2-(1-methyl-1H-pyrazol-4-yl)-9H-purin-6-ylamino)ethyl)phenol; 4-(2-(9-isopropyl-2-(pyridin-3-yl)-9H-purin-6-ylamino)ethyl)-2-methoxyphenol; 4-(2-(9-isopropyl-2-(pyridin-3-yl)-9H-purin-6-ylamino)ethyl)-2-methoxyphenol; N-[2-(6-methoxy-1H-indol-3-yl)ethyl]-9-(propan-2-yl)-2-(pyridin-3-yl)-9H-purin-6-amine; N-[2-(5-methyl-1H-indol-3-yl)ethyl]-9-(propan-2-yl)-2-(pyridin-3-yl)-9H-purin-6-amine; 1-(2-{[9-(propan-2-yl)-2-(pyridin-3-yl)-9H-purin-6-yl]amino}ethyl)imidazolidin-2-one; N-(2-{[9-(propan-2-yl)-2-(pyridin-3-yl)-9H-purin-6-yl]amino}ethyl)pyridin-2-amine; 9-(propan-2-yl)-N-[3-(1H-pyrazol-4-yl)propyl]-2-(pyridin-3-yl)-9H-purin-6-amine; N-{2-[(3-methyl-1H-1,2,4-triazol-5-yl)sulfanyl]ethyl}-9-(propan-2-yl)-2-(pyridin-3-yl)-9H-purin-6-amine; 1-(2-{[2-(1-benzothiophen-3-yl)-9-(propan-2-yl)-9H-purin-6-yl]amino}ethyl)imidazolidin-2-one; N-[2-(5-amino-1H-1,2,4-triazol-3-yl)ethyl]-2-(1-benzothiophen-3-yl)-9-(propan-2-yl)-9H-purin-6-amine; N-(2-{[2-(1-benzothiophen-3-yl)-9-(propan-2-yl)-9H-purin-6-yl]amino}ethyl)pyridin-2-amine; 2-(1-benzothiophen-3-yl)-9-(propan-2-yl)-N-[3-(1H-pyrazol-4-yl)propyl]-9H-purin-6-amine; 2-(1-benzothiophen-3-yl)-N-[3-(3,5-dimethyl-1H-pyrazol-4-yl)propyl]-9-(propan-2-yl)-9H-purin-6-amine; (2-{[2-(1-benzothiophen-3-yl)-9-(propan-2-yl)-9H-purin-6-yl]amino}ethyl)urea; 5-({[2-(1-benzothiophen-3-yl)-9-(propan-2-yl)-9H-purin-6-yl]amino}methyl)-2,3-dihydro-1H-1,3-benzodiazol-2-one; N-[2-(1H-indol-3-yl)ethyl]-9-(propan-2-yl)-2-(pyridin-3-yl)-9H-purin-6-amine; N-(4-(2-(9-isopropyl-2-(pyridin-3-yl)-9H-purin-6-ylamino)ethyl)phenyl)methane-sulfonamide; 4-(2-(2-(pyridin-3-yl)-9-(tetrahydrofuran-3-yl)-9H-purin-6-ylamino)ethyl)phenol; 4-(2-(9-isopropyl-2-(pyridin-3-yl)-9H-purin-6-ylamino)propyl)phenol; 4-(2-(9-(oxetan-3-yl)-2-(pyridin-3-yl)-9H-purin-6-ylamino)ethyl)phenol; 5-(6-(4-hydroxyphenethylamino)-9-isopropyl-9H-purin-2-yl)-N-methylnicotinamide; 4-(2-(9-(1-hydroxypropan-2-yl)-2-(pyridin-3-yl)-9H-purin-6-ylamino)ethyl)phenol; 4-(2-(9-isopropyl-2-(pyridin-3-yl)-9H-purin-6-ylamino)ethyl)phenyl sulfamate; 4-(2-(2-(2-fluoropyridin-3-yl)-9-isopropyl-9H-purin-6-ylamino)ethyl) phenol; 4-(2-(9-isopropyl-2-(1-methyl-1H-pyrrol-2-yl)-9H-purin-6-ylamino)ethyl)phenol; 4-(2-(9-isopropyl-2-(thiazol-5-yl)-9H-purin-6-ylamino)ethyl)phenol; 4-(2-(2-(1H-benzo[d]imidazol-1-yl)-9-isopropyl-9H-purin-6-ylamino)ethyl) phenol; 4-(2-(2-(2,4-dimethyl-1H-imidazol-1-yl)-9-isopropyl-9H-purin-6-ylamino)ethyl)phenol; 4-(2-(9-isopropyl-2-(2-methyl-1H-imidazol-1-yl)-9H-purin-6-ylamino)ethyl)phenol; 5-(9-sec-butyl-6-(4-hydroxy-3-methylphenethylamino)-9H-purin-2-yl)nicotinonitrile; N-(2-(1H-pyrrolo[2,3-b]pyridin-5-yl)ethyl)-9-isopropyl-2-(pyridin-3-yl)-9H-purin-6-amine; 9-isopropyl-N-(2-(5-methyl-1H-pyrazol-3-yl)ethyl)-2-(pyridin-3-yl)-9H-purin-6-amine; 4-(2-(2-(5-fluoropyridin-3-yl)-9-(oxetan-3-yl)-9H-purin-6-ylamino)ethyl)phenol; 4-(2-(2-(5-chloropyridin-3-yl)-9-isopropyl-9H-purin-6-ylamino)ethyl)phenol; 4-(2-(9-isopropyl-2-(5-(trifluoromethyl)pyridin-3-yl)-9H-purin-6- ylamino)ethyl)phenol; 5-(6-(2-(1H-indol-3-yl)ethylamino)-9-sec-butyl-9H-purin-2-yl)nicotinonitrile; N-(2-(1H-indol-3-yl)ethyl)-9-sec-butyl-2-(5-methylpyridin-3-yl)-9H-purin-6-amine; (R)—N-(2-(1H-indol-3-yl)ethyl)-9-sec-butyl-2-(5-fluoropyridin-3-yl)-9H-purin-6-amine; (S)—N-(2-(1H-indol-3-yl)ethyl)-9-sec-butyl-2-(5-fluoropyridin-3-yl)-9H-purin-6-amine; N-(2-(1H-indol-3-yl)ethyl)-9-sec-butyl-2-(5-fluoropyridin-3-yl)-9H-purin-6-amine; (R)—N-(2-(1H-indol-3-yl)ethyl)-9-sec-butyl-2-(5-methylpyridin-3-yl)-9H-purin-6-amine; (S)—N-(2-(1H-indol-3-yl)ethyl)-9-sec-butyl-2-(5-methylpyridin-3-yl)-9H-purin-6-amine; 5-(6-(4-hydroxyphenethylamino)-9-(oxetan-3-yl)-9H-purin-2-yl)nicotinonitrile; 4-(2-(6-(5-fluoropyridin-3-yl)-1-isopropyl-1H-pyrazolo[3,4-d]pyrimidin-4-ylamino)ethyl)phenol; 4-(2-(6-(benzo[b]thiophen-3-yl)-1-isopropyl-1H-pyrazolo[3,4-d]pyrimidin-4-ylamino)ethyl)phenol; (R)-4-(2-(2-(5-fluoropyridin-3-yl)-9-(tetrahydrofuran-3-yl)-9H-purin-6-ylamino)ethyl)phenol; 4-(2-(9-isopropyl-2-(pyridin-3-yl)-9H-purin-6-ylamino)ethyl)-3-methylphenol; 5-(6-(4-hydroxyphenethylamino)-9-isopropyl-9H-purin-2-yl)picolinonitrile; 3-(6-(4-hydroxyphenethylamino)-9-isopropyl-9H-purin-2-yl)isonicotinonitrile; 4-(2-(2-(5-fluoropyridin-3-yl)-7-isopropyl-7H-pyrrolo[2,3-d]pyrimidin-4-ylamino)ethyl)phenol; 3-(6-(4-hydroxyphenethylamino)-9-isopropyl-9H-purin-2-yl)picolinonitrile; 4-(2-(9-isopropyl-2-(6-methylpyridin-3-yl)-9H-purin-6-ylamino)ethyl)phenol; 4-(2-(9-isopropyl-2-(isoquinolin-4-yl)-9H-purin-6-ylamino)ethyl)phenol; 2-chloro-4-(2-(9-isopropyl-2-(pyridin-3-yl)-9H-purin-6-ylamino)ethyl)phenol; 3-fluoro-4-(2-(9-isopropyl-2-(pyridin-3-yl)-9H-purin-6-ylamino)ethyl)phenol; N-(2-(5-chloro-1H-indol-3-yl)ethyl)-9-isopropyl-2-(pyridin-3-yl)-9H-purin-6-amine; N-(2-(5-fluoro-1H-indol-3-yl)ethyl)-9-isopropyl-2-(pyridin-3-yl)-9H-purin-6-amine; 4-(2-(9-isopropyl-2-(pyridin-3-yl)-9H-purin-6-ylamino)ethyl)-2-methylphenol; 4-(2-(2-(benzo[b]thiophen-3-yl)-9-(oxetan-3-yl)-9H-purin-6-ylamino)ethyl)phenol; (S)-4-(2-(2-(benzo[b]thiophen-3-yl)-9-(tetrahydrofuran-3-yl)-9H-purin-6-ylamino)ethyl)phenol; (R)-4-(2-(2-(benzo[b]thiophen-3-yl)-9-(tetrahydrofuran-3-yl)-9H-purin-6-ylamino)ethyl)phenol; 2-(6-(2-(1H-indol-3-yl)ethylamino)-2-(5-fluoropyridin-3-yl)-9H-purin-9-yl)propan-1-ol; (R)-2-(6-(2-(1H-indol-3-yl)ethylamino)-2-(5-fluoropyridin-3-yl)-9H-purin-9-yl)propan-1-ol; (S)-2-(6-(2-(1H-indol-3-yl)ethylamino)-2-(5-fluoropyridin-3-yl)-9H-purin-9-yl)propan-1-ol; (R)—N-(2-(1H-indol-3-yl)ethyl)-2-(5-fluoropyridin-3-yl)-9-(tetrahydrofuran-3-yl)-9H-purin-6-amine; 4-(2-(2-(3H-imidazo[4,5-b]pyridin-3-yl)-9-isopropyl-9H-purin-6-ylamino)ethyl)phenol; 4-(2-(2-(1H-imidazo[4,5-b]pyridin-1-yl)-9-isopropyl-9H-purin-6-ylamino)ethyl)phenol; 4-(2-(6-(5-fluoropyridin-3-yl)-1-isopropyl-1H-imidazo[4,5-c]pyridin-4-ylamino)ethyl)phenol; 4-(2-(2-(4,5-dimethyl-1H-imidazol-1-yl)-9-isopropyl-9H-purin-6-ylamino)ethyl)phenol; 2-(5-fluoropyridin-3-yl)-9-isopropyl-N-(2-(pyridin-3-yl)ethyl)-9H-purin-6-amine; 4-(2-(2-(5-fluoropyridin-3-yl)-9-isopropyl-9H-purin-6-ylamino)-1-hydroxyethyl)phenol; 2-(5-fluoropyridin-3-yl)-9-isopropyl-N-(2-(6-methoxy-1H-indol-3-yl)ethyl)-9H-purin-6-amine; N-(2-(1H-indol-3-yl)ethyl)-2-(5-fluoropyridin-3-yl)-9-isopropyl-9H-purin-6-amine; 2-(5-fluoropyridin-3-yl)-9-isopropyl-N-(2-(5-methoxy-1H-indol-3-yl)ethyl)-9H-purin-6-amine; N-(2-(1H-indol-3-yl)ethyl)-2-(5-fluoropyridin-3-yl)-9-(prop-1-en-2-yl)-9H-purin-6-amine; 5-(2-(2-(5-fluoropyridin-3-yl)-9-isopropyl-9H-purin-6-ylamino)ethyl)pyridin-2-ol; N-(2-(1H-pyrrolo[2,3-b]pyridin-3-yl)ethyl)-2-(5-fluoropyridin-3-yl)-9-isopropyl-9H-purin-6-amine; N-(2-(6-(2-(diethylamino)ethoxy)-1H-indol-3-yl)ethyl)-2-(5-fluoropyridin-3-yl)-9-isopropyl-9H-purin-6-amine; 4-(2-(5-(5-fluoropyridin-3-yl)-3-isopropyl-3H-imidazo[4,5-b]pyridin-7-ylamino)ethyl)phenol; N-(2-(1H-indol-3-yl)ethyl)-9-sec-butyl-2-(2-methyl-1H-imidazol-1-yl)-9H-purin-6-amine; 4-(2-(2-(2-ethyl-1H-imidazol-1-yl)-9-isopropyl-9H-purin-6-ylamino)ethyl)phenol; 4-(2-(9-isopropyl-2-(2-propyl-1H-imidazol-1-yl)-9H-purin-6-ylamino)ethyl)phenol; 3-(2-(2-(5-fluoropyridin-3-yl)-9-isopropyl-9H-purin-6-ylamino)ethyl)-1H-indol-6-ol; N-(2-(1H-indol-3-yl)ethyl)-9-isopropyl-2-(5-methylpyridin-3-yl)-9H-purin-6-amine; N-(2-(1H-indol-3-yl)ethyl)-9-isopropyl-2-(2-methyl-1H-imidazol-1-yl)-9H-purin-6-amine; 2-(5-fluoropyridin-3-yl)-9-isopropyl-N-(2-(7-methyl-1H-indol-3-yl)ethyl)-9H-purin-6-amine; N-(2-(1H-indol-3-yl)ethyl)-2-(5-fluoropyridin-3-yl)-9-(oxetan-3-yl)-9H-purin-6-amine; N-(2-(1H-indol-3-yl)ethyl)-2-(5-methylpyridin-3-yl)-9-(oxetan-3-yl)-9H-purin-6-amine; N-(2-(6-fluoro-1H-indol-3-yl)ethyl)-2-(5-fluoropyridin-3-yl)-9-isopropyl-9H-purin-6-amine; 2-(5-fluoropyridin-3-yl)-9-isopropyl-N-(2-(6-methyl-1H-indol-3-yl)ethyl)-9H-purin-6-amine; 2-(5-fluoropyridin-3-yl)-9-isopropyl-N-(2-(2-methyl-1H-indol-3-yl)ethyl)-9H-purin-6-amine; N-(2-(4-fluoro-1H-indol-3-yl)ethyl)-2-(5-fluoropyridin-3-yl)-9-isopropyl-9H-purin-6-amine; N-(2-(7-fluoro-1H-indol-3-yl)ethyl)-2-(5-fluoropyridin-3-yl)-9-isopropyl-9H-purin-6-amine; 2-(5-fluoropyridin-3-yl)-9-isopropyl-N-(2-(4-methyl-1H-indol-3-yl)ethyl)-9H-purin-6-amine; 4-(2-(2-(benzo[b]thiophen-3-yl)-7-isopropyl-7H-pyrrolo[2,3-d]pyrimidin-4-ylamino)ethyl)phenol; 9-isopropyl-2-(pyridin-3-yl)-N-(2-(pyridin-4-yl)ethyl)-9H-purin-6-amine; N-(2-(1H-pyrrolo[2,3-b]pyridin-5-yl)ethyl)-9-isopropyl-2-(pyridin-3-yl)-9H-purin-6-amine; 4-(2-(2-(5-fluoropyridin-3-yl)-9-(1-hydroxypropan-2-yl)-9H-purin-6-ylamino)ethyl)-2-methylphenol; 4-(2-(2-(benzo[b]thiophen-3-yl)-9-cyclohexyl-9H-purin-6-ylamino)ethyl)phenol; 4-(2-(9-isopropyl-2-(thiophen-3-yl)-9H-purin-6-ylamino)ethyl)phenol; and 1-(2-(2-(benzo[b]thiophen-3-yl)-6-(4-hydroxyphenethylamino)-9H-purin-9-yl)ethyl)pyrrolidin-2-one. Compounds of Formula I are detailed in the Examples and Table I, infra.

In another embodiment are compounds of Formula Ia:

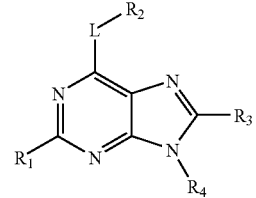

in which:

L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH(CH$_3$)CH$_2$—, —(CH$_2$)$_3$—, —CH$_2$OCH$_2$—, —CH$_2$NR$_{5a}$CH$_2$—, —NR$_{5a}$C(O)CH$_2$— and —NR$_{5a}$Y—; wherein R$_{5a}$ and R$_{5b}$ are independently selected from hydrogen and C$_{1-4}$alkyl; and Y is a 5 member heteroaryl ring containing up to 3 heteroatoms selected from O, N and S;

R$_1$ is selected from hydrogen, phenyl, thiophen-2-yl, thiophen-3-yl, furan-2-yl, furan-3-yl, benzo[b]thiophen-2-yl, benzo[b]thiophen-3-yl, benzofuran-2-yl, benzofuran-3-yl, pyrimidin-4-yl, pyrimidin-5-yl, 1H-pyrazol-4-yl, 1H-pyrazol-3-yl, pyridin-2-yl, pyridazin-3-yl, pyridin-4-yl, 1H-imidazol-1-yl, pyrrolidin-1-yl, pyrazin-2-yl, pyridin-3-yl, 1H-pyrazol-1-yl, pyridazin-4-yl, 1H-indol-2-yl, thiazol-4-yl, 1H-indol-3-yl, 1H-pyrrol-2-yl and thiazol-5-yl; wherein said phenyl, thiophen-2-yl, thiophen-3-yl, furan-2-yl, furan-3-yl, benzo[b]thiophen-2-yl, benzo[b]thiophen-3-yl, benzofuran-2-yl, benzofuran-3-yl, pyrimidin-4-yl, pyrimidin-5-yl, 1H-pyrazol-4-yl, 1H-pyrazol-3-yl, pyridin-2-yl, pyridazin-3-yl, pyridin-4-yl, 1H-imidazol-1-yl, pyrrolidin-1-yl, pyrazin-2-yl, pyridin-3-yl, 1H-pyrazol-1-yl, pyridazin-4-yl, 1H-indol-2-yl, thiazol-4-yl, 1H-indol-3-yl, 1H-pyrrol-2-yl or thiazol-5-yl of $R_1$ can be optionally substituted by 1 to 3 radicals independently selected from cyano, hydroxy, $C_{1-4}$alkyl, $C_{1-4}$alkoxy, halo, halo-substituted-$C_{1-4}$alkyl, halo-substituted-$C_{1-4}$alkoxy, hydroxy, amino, —C(O)$R_{8a}$, —S(O)$_{0-2}R_{8a}$, —C(O)O$R_{8a}$ and —C(O)N$R_{8a}R_{8b}$; wherein $R_{8a}$ and $R_{8b}$ are independently selected from hydrogen and $C_{1-4}$alkyl; with the proviso that $R_1$ and $R_3$ are not both hydrogen;

$R_2$ is selected from —S(O)$_2$N$R_{6a}R_{6b}$, —N$R_{9a}$C(O)$R_{9b}$, —N$R_{6a}$C(O)N$R_{6b}R_{6c}$, phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl; wherein $R_{6a}$, $R_{6b}$ and $R_{6c}$ are independently selected from hydrogen and $C_{1-4}$alkyl; wherein said phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl or furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl or 1H-imidazol-4-yl of $R_2$ is optionally substituted with 1 to 3 radicals independently selected from hydroxy, halo, methyl, methoxy, amino, —S(O)$_2$N$R_{7a}R_{7b}$, —OS(O)$_2$N$R_{7a}R_{7b}$ and —N$R_{7a}$S(O)$_2R_{7b}$; wherein $R_{7a}$ and $R_{7b}$ are independently selected from hydrogen and $C_{1-4}$alkyl; or a single radical selected from 5-((3aS,4S,6aR)-2-oxohexahydro-1H-thieno[3,4-d]imidazol-4-yl)pentanoyloxy, 2-(2-(5-((3aS,4S,6aR)-2-oxohexahydro-1H-thieno[3,4-d]imidazol-4-yl)pentanamido)ethoxy)ethoxy and 2-(4-(4-hex-5-ynamidobenzoyl)phenylamino)-2-oxoethoxy;

$R_3$ is selected from hydrogen, $C_{1-4}$alkyl and biphenyl; and $R_4$ is selected from isopropyl, isobutyl, sec-butyl, 1-hydroxypropan-2-yl, cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl)ethyl can be optionally substituted with 1 to 3 radicals independently selected from $C_{1-4}$alkyl and halo-substituted-$C_{1-4}$alkyl; or the N-oxide derivatives, pro-drug derivatives, protected derivatives, individual isomers and mixture of isomers thereof; or the pharmaceutically acceptable salts and solvates (e.g. hydrates) of such compounds.

In a further embodiment, with reference to compounds of Formula Ia, L is selected from —N$R_{5a}$(CH$_2$)$_{0-3}$—, —N$R_{5a}$CH(C(O)OCH$_3$)CH$_2$—, —N$R_{5a}$(CH$_2$)$_2$N$R_{5b}$—, —N$R_{5a}$(CH$_2$)$_2$S—, —N$R_{5a}$CH$_2$CH(CH$_3$)CH$_2$—, —N$R_{5a}$CH(CH$_3$)CH$_2$—, —(CH$_2$)$_3$—, —CH$_2$OCH$_2$—, —CH$_2$N$R_{5a}$CH$_2$—, —N$R_{5a}$C(O)CH$_2$— and —N$R_{5a}$Y—; wherein $R_{5a}$ and $R_{5b}$ are independently selected from hydrogen and methyl; Y is selected from isoxazole and 1,3,4-oxadiazole.

In another embodiment, when L is —N$R_{5a}$(CH$_2$)$_{0-3}$, it is preferably —N$R_{5a}$(CH$_2$)$_{1-3}$ (where 1-3 herein means 1, 2 or 3).

In another embodiment, $R_1$ is selected from hydrogen, phenyl, thiophen-3-yl, thiophen-2-yl, furan-3-yl, furan-2-yl, benzo[b]thiophen-3-yl, pyrimidin-5-yl, pyridin-4-yl, pyridin-2-yl, pyrrolidin-1-yl, 1H-pyrazol-4-yl, pyrazin-2-yl, pyridazin-3-yl, pyridazin-4-yl, 1H-pyrazol-1-yl, 1H-pyrazol-3-yl, 1H-imidazol-1-yl, thiazol-4-yl, 1H-pyrrol-2-yl, thiazol-5-yl, and pyridin-3-yl; wherein said phenyl, thiophen-3-yl, thiophen-2-yl, furan-3-yl, furan-2-yl, benzo[b]thiophen-3-yl, pyrimidin-5-yl, pyridin-4-yl, pyridin-2-yl, pyrrolidin-1-yl, 1H-pyrazol-4-yl, pyrazin-2-yl, pyridazin-3-yl, pyridazin-4-yl, 1H-pyrazol-1-yl, 1H-pyrazol-3-yl, 1H-imidazol-1-yl, thiazol-4-yl, 1H-pyrrol-2-yl, thiazol-5-yl or pyridin-3-yl of $R_1$ is optionally substituted with 1 to 3 radicals independently selected from cyano, methyl, methyl-sulfonyl, methoxy, halo, hydroxy, carboxyl, ethoxy-carbonyl, methyl-amino-carbonyl and amino; with the proviso that $R_1$ and $R_3$ are not both hydrogen.

In another embodiment, $R_2$ is selected from amino-sulfonyl, methyl-carbonyl-amino, methyl-sulfonyl-amino, amino-sulfonyl-oxy, urea, phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl; wherein said phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl of $R_2$ is optionally substituted with hydroxy, methoxy, methyl, halo, amino, amino-sulfonyl, 5-((3aS,4S,6aR)-2-oxohexahydro-1H-thieno[3,4-d]imidazol-4-yl)
pentanoyloxy, 2-(2-(5-((3aS,4S,6aR)-2-oxohexahydro-1H-thieno[3,4-d]imidazol-4-yl)pentanamido)ethoxy)ethoxy and 2-(4-(4-hex-5-ynamidobenzoyl)phenylamino)-2-oxoethoxy.

In another embodiment, $R_3$ is selected from hydrogen, methyl, and biphenyl; and $R_4$ is selected from isopropyl, isobutyl, sec-butyl, 1-hydroxypropan-2-yl, cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl)ethyl can be optionally substituted with 1 to 3 radicals independently selected from methyl and trifluoromethyl.

In another embodiment are compounds selected from: 4-(2-(2-(benzo[b]thiophen-3-yl)-9-isopropyl-9H-purin-6-ylamino)ethyl)phenol; 4-(2-(2-(benzo[b]thiophen-3-yl)-9-sec-butyl-9H-purin-6-ylamino)ethyl)phenol; 4-(2-(9-benzhydryl-2-(benzo[b]thiophen-3-yl)-9H-purin-6-ylamino) ethyl)phenol; 4-(2-(2-(benzo[b]thiophen-3-yl)-9-(tetrahydro-2H-pyran-3-yl)-9H-purin-6-ylamino)ethyl) phenol; 4-(2-(2-(benzo[b]thiophen-3-yl)-9-(4-(trifluoromethyl)benzyl)-9H-purin-6-ylamino)ethyl)phenol; 4-(2-(2-(benzo[b]thiophen-3-yl)-9-isobutyl-9H-purin-6-ylamino)ethyl)phenol; 4-(2-(2-(benzo[b]thiophen-3-yl)-9-methyl-9H-purin-6-ylamino)ethyl)phenol; 4-(2-(2-(benzo [b]thiophen-3-yl)-9-(4-methylbenzyl)-9H-purin-6-ylamino) ethyl)phenol; N-(2-(1H-indol-3-yl)ethyl)-2-(benzo[b] thiophen-3-yl)-9-isopropyl-9H-purin-6-amine; 2-(benzo[b] thiophen-3-yl)-9-isopropyl-N-(2-(thiophen-3-yl)ethyl)-9H-purin-6-amine; 3-(2-(2-(benzo[b]thiophen-3-yl)-9-isopropyl-9H-purin-6-ylamino)ethyl)phenol; 2-(benzo[b] thiophen-3-yl)-N-(4-fluorophenethyl)-9-isopropyl-9H-purin-6-amine; N-(4-aminophenethyl)-2-(benzo[b] thiophen-3-yl)-9-isopropyl-9H-purin-6-amine; 4-(2-(9-isopropyl-2-(pyrimidin-5-yl)-9H-purin-6-ylamino)ethyl) phenol; 4-(2-(9-isopropyl-2-(pyridin-3-yl)-9H-purin-6-ylamino)ethyl)phenol; 4-(2-(9-isopropyl-2-phenyl-9H-purin-6-ylamino)ethyl)phenol; 4-(2-(9-isopropyl-2-(thiophen-3-yl)-9H-purin-6-ylamino)ethyl)phenol; 4-(2-(2-(furan-3-yl)-9-isopropyl-9H-purin-6-ylamino)ethyl)phenol; 2-(benzo[b]thiophen-3-yl)-N-(4-fluorophenethyl)-9-phenyl-9H-purin-6-amine; N-benzyl-8-(biphenyl-4-yl)-9-isopropyl-9H-purin-6-amine; 4-(2-(2-(benzo[b]thiophen-3-yl)-9-(nonan-2-yl)-9H-purin-6-ylamino)ethyl)phenol; 4-(2-(2-(benzo[b]thiophen-3-yl)-9-((4-pentylphenyl)(phenyl) methyl)-9H-purin-6-ylamino)ethyl)phenol; N-(2-(1H-indol-3-yl)ethyl)-2-(benzo[b]thiophen-3-yl)-9-sec-butyl-9H-purin-6-amine; 4-(2-(2-(benzo[b]thiophen-3-yl)-9-sec-butyl-9H-purin-6-ylamino)ethyl)phenol; 3-(2-(2-(benzo[b] thiophen-3-yl)-9-isopropyl-9H-purin-6-ylamino)ethyl)-1H-indol-5-ol; 3-(2-(2-(benzo[b]thiophen-3-yl)-9-isopropyl-9H-purin-6-ylamino)ethyl)-1H-indol-5-yl, 5-((3aS,4S,6aR)-2-oxohexahydro-1H-thieno[3,4-d]imidazol-4-yl) pentanoate; N-(2-(2-(3-(2-(2-(benzo[b]thiophen-3-yl)-9-isopropyl-9H-purin-6-ylamino)ethyl)-1H-indol-5-yloxy) ethoxy)ethyl)-5-((3aS,4S,6aR)-2-oxohexahydro-1H-thieno [3,4-d]imidazol-4-yl)pentanamide; N-(4-(4-(2-(3-(2-(2-(benzo[b]thiophen-3-yl)-9-isopropyl-9H-purin-6-ylamino) ethyl)-1H-indol-5-yloxy)acetamido)benzoyl)phenyl)hex-5-ynamide; N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide; 4-(2-(9-isopropyl-2-(pyridin-4-yl)-9H-purin-6-ylamino)ethyl) phenol; ethyl 5-(6-(4-hydroxyphenethylamino)-9-isopropyl-9H-purin-2-yl)nicotinate; ethyl 5-(6-(4-hydroxyphenethylamino)-9-isopropyl-9H-purin-2-yl) nicotinate; 4-(2-(2-(6-fluoropyridin-3-yl)-9-isopropyl-9H-purin-6-ylamino)ethyl)phenol; 4-(2-(9-isopropyl-2-(4-methylpyridin-3-yl)-9H-purin-6-ylamino)ethyl)phenol; 4-(2-(9-isopropyl-2-(2-methoxypyridin-3-yl)-9H-purin-6-ylamino) ethyl)phenol; 5-(6-(4-hydroxyphenethylamino)-9-isopropyl-9H-purin-2-yl)nicotinonitrile; 4-(2-(9-isopropyl-2-(pyrrolidin-1-yl)-9H-purin-6-ylamino)ethyl)phenol; 4-(2-(9-isopropyl-2-(1H-pyrazol-1-yl)-9H-purin-6-ylamino) ethyl)phenol; 4-(2-(2-(1H-imidazol-1-yl)-9-isopropyl-9H-purin-6-ylamino)ethyl)phenol; 4-(2-(9-isopropyl-2-(pyridazin-3-yl)-9H-purin-6-ylamino)ethyl)phenol; 4-(2-(9-isopropyl-2-(pyridazin-4-yl)-9H-purin-6-ylamino)ethyl) phenol; 4-(2-(9-isopropyl-2-(pyrazin-2-yl)-9H-purin-6-ylamino)ethyl)phenol; 4-(2-(9-isopropyl-2-(pyridin-2-yl)-9H-purin-6-ylamino)ethyl)phenol; 4-(2-(9-isopropyl-2-(5-(methylsulfonyl)pyridin-3-yl)-9H-purin-6-ylamino)ethyl) phenol; 4-(2-(9-isopropyl-2-(5-methylpyridin-3-yl)-9H-purin-6-ylamino)ethyl)phenol; 4-(2-(2-(2-chloropyridin-3-yl)-6-isopropyl-2,6-dihydroimidazo[4,5-c]pyrazol-3-ylamino)ethyl)phenol; 4-(2-(2-(4-chloropyridin-3-yl)-9-isopropyl-9H-purin-6-ylamino)ethyl)phenol; 4-(2-(9-isopropyl-2-(4-methoxypyridin-3-yl)-9H-purin-6-ylamino) ethyl)phenol; 4-(2-(2-(5-fluoropyridin-3-yl)-9-isopropyl-9H-purin-6-ylamino)ethyl)phenol; 4-(2-(9-isopropyl-2-(thiazol-4-yl)-9H-purin-6-ylamino)ethyl)phenol; 4-(2-(9-isopropyl-2-(1-methyl-1H-pyrazol-4-yl)-9H-purin-6-ylamino)ethyl)phenol; 4-(2-(9-isopropyl-2-(1H-pyrazol-3-yl)-9H-purin-6-ylamino)ethyl)phenol; 4-(2-(9-isopropyl-2-(1H-pyrazol-4-yl)-9H-purin-6-ylamino)ethyl)phenol; 4-(2-(9-isopropyl-2-(thiophen-2-yl)-9H-purin-6-ylamino)ethyl) phenol; 4-(6-(4-hydroxyphenethylamino)-9-isopropyl-9H-purin-2-yl)thiophene-2-carboxylic acid; 4-(2-(2-(furan-2-yl)-9-isopropyl-9H-purin-6-ylamino)ethyl)phenol; 4-(2-(9-isopropyl-2-(4-methylthiophen-3-yl)-9H-purin-6-ylamino) ethyl)phenol; 4-(2-(9-isopropyl-2-(pyridin-3-yl)-9H-purin-6-ylamino)ethyl)-2-methoxyphenol; 4-(2-(9-isopropyl-2-(pyridin-3-yl)-9H-purin-6-ylamino)ethyl)-2-methoxyphenol; N-[2-(6-methoxy-1H-indol-3-yl)ethyl]-9-(propan-2-yl)-2-(pyridin-3-yl)-9H-purin-6-amine; N-[2-(5-methyl-1H-indol-3-yl)ethyl]-9-(propan-2-yl)-2-(pyridin-3-yl)-9H-purin-6-amine; N-[2-(piperidin-4-yl)ethyl]-9-(propan-2-yl)-2-(pyridin-3-yl)-9H-purin-6-amine; 1-(2-{[9-(propan-2-yl)-2-(pyridin-3-yl)-9H-purin-6-yl]amino}ethyl) piperidin-4-ol; methyl (2S)-3-(4-hydroxyphenyl)-2-{[9-(propan-2-yl)-2-(pyridin-3-yl)-9H-purin-6-yl] amino}propanoate; 4-(2-{[9-(propan-2-yl)-2-(pyridin-3-yl)-9H-purin-6-yl]amino}ethyl)benzene-1-sulfonamide; 2-{[2-(1-benzothiophen-3-yl)-9-(propan-2-yl)-9H-purin-6-yl] amino}ethane-1-sulfonamide; 4-(2-{[9-(propan-2-yl)-2-(pyridin-3-yl)-9H-purin-6-yl]amino}ethyl)benzene-1,2-diol; N-[2-(1H-imidazol-4-yl)ethyl]-9-(propan-2-yl)-2-(pyridin-3-yl)-9H-purin-6-amine; 1-(2-{[9-(propan-2-yl)-2-(pyridin-3-yl)-9H-purin-6-yl]amino}ethyl)imidazolidin-2-one; N-[2-(5-amino-1H-1,2,4-triazol-3-yl)ethyl]-9-(propan-2-yl)-2-(pyridin-3-yl)-9H-purin-6-amine; N-(2-{[9-(propan-2-yl)-2-(pyridin-3-yl)-9H-purin-6-yl]amino}ethyl)pyridin-2-amine; 9-(propan-2-yl)-N-[3-(1H-pyrazol-4-yl)propyl]-2-(pyridin-3-yl)-9H-purin-6-amine; N-[2-({[9-(propan-2-yl)-2-(pyridin-3-yl)-9H-purin-6-yl]amino}methyl)propyl] acetamide; 4-(2-{[9-(propan-2-yl)-2-(pyridin-3-yl)-9H-purin-6-yl]amino}ethyl)piperazin-2-one; N-{2-[(3-methyl-1H-1,2,4-triazol-5-yl)sulfanyl]ethyl}-9-(propan-2-yl)-2-(pyridin-3-yl)-9H-purin-6-amine; N-[3-(3,5-dimethyl-1H-pyrazol-4-yl)propyl]-9-(propan-2-yl)-2-(pyridin-3-yl)-9H-purin-6-amine; (2-{[9-(propan-2-yl)-2-(pyridin-3-yl)-9H- purin-6-yl]amino}ethyl)urea; 5-({[9-(propan-2-yl)-2-(pyridin-3-yl)-9H-purin-6-yl]amino}methyl)-2,3-dihydro-1H-1,3-benzodiazol-2-one; 2-(1-benzothiophen-3-yl)-N-[2-(1H-imidazol-4-yl)ethyl]-9-(propan-2-yl)-9H-purin-6-amine; 1-(2-{[2-(1-benzothiophen-3-yl)-9-(propan-2-yl)-9H-purin-6-yl]amino}ethyl)imidazolidin-2-one; N-[2-(5-amino-1H-1,2,4-triazol-3-yl)ethyl]-2-(1-benzothiophen-3-yl)-9-(propan-2-yl)-9H-purin-6-amine; N-(2-{[2-(1-benzothiophen-3-yl)-9-(propan-2-yl)-9H-purin-6-yl]amino}ethyl)pyridin-2-amine; 2-(1-benzothiophen-3-yl)-9-(propan-2-yl)-N-[3-(1H-pyrazol-4-yl)propyl]-9H-purin-6-amine; N-[2-({[2-(1-benzothiophen-3-yl)-9-(propan-2-yl)-9H-purin-6-yl]amino}methyl)propyl]acetamide; 4-(2-{[2-(1-benzothiophen-3-yl)-9-(propan-2-yl)-9H-purin-6-yl]amino}ethyl)piperazin-2-one; 2-(1-benzothiophen-3-yl)-N-{2-[(3-methyl-1H-1,2,4-triazol-5-yl)sulfanyl]ethyl}-9-(propan-2-yl)-9H-purin-6-amine; 2-(1-benzothiophen-3-yl)-N-[3-(3,5-dimethyl-1H-pyrazol-4-yl)propyl]-9-(propan-2-yl)-9H-purin-6-amine; (2-{[2-(1-benzothiophen-3-yl)-9-(propan-2-yl)-9H-purin-6-yl]amino}ethyl)urea; 5-({[2-(1-benzothiophen-3-yl)-9-(propan-2-yl)-9H-purin-6-yl]amino}methyl)-2,3-dihydro-1H-1,3-benzodiazol-2-one; N-[2-(1H-indol-3-yl)ethyl]-9-(propan-2-yl)-2-(pyridin-3-yl)-9H-purin-6-amine; N-(4-(2-(9-isopropyl-2-(pyridin-3-yl)-9H-purin-6-ylamino)ethyl)phenyl)methanesulfonamide; 4-(2-(2-(pyridin-3-yl)-9-(tetrahydrofuran-3-yl)-9H-purin-6-ylamino)ethyl)phenol; 4-(2-(9-isopropyl-2-(pyridin-3-yl)-9H-purin-6-ylamino)propyl)phenol; 4-(2-(9-(oxetan-3-yl)-2-(pyridin-3-yl)-9H-purin-6-ylamino)ethyl)phenol; 5-(6-(4-hydroxyphenethylamino)-9-isopropyl-9H-purin-2-yl)-N-methylnicotinamide; 6-(9-isopropyl-2-(pyridin-3-yl)-9H-purin-6-ylamino)-5,6,7,8-tetrahydronaphthalen-2-ol; N-(2-(1H-indazol-3-yl)ethyl)-9-isopropyl-2-(pyridin-3-yl)-9H-purin-6-amine; 4-(2-((9-isopropyl-2-(pyridin-3-yl)-9H-purin-6-yl)(methyl)amino)ethyl)phenol; 4-(2-(9-isopropyl-8-methyl-2-(pyridin-3-yl)-9H-purin-6-ylamino)ethyl)phenol; 1-(2-(9-isopropyl-2-(pyridin-3-yl)-9H-purin-6-ylamino)ethyl)-1H-benzo[d]imidazol-2(3H)-one; 4-(3-(9-isopropyl-2-(pyridin-3-yl)-9H-purin-6-yl)propyl)phenol; 4-((((9-isopropyl-2-(pyridin-3-yl)-9H-purin-6-yl)methyl)(methyl)amino)methyl)phenol; 4-(((9-isopropyl-2-(pyridin-3-yl)-9H-purin-6-yl)methylamino)methyl)phenol; 4-(((9-isopropyl-2-(pyridin-3-yl)-9H-purin-6-yl)methoxy)methyl)phenol; N-(2-(indolin-5-yl)ethyl)-9-isopropyl-2-(pyridin-3-yl)-9H-purin-6-amine; 4-(2-(9-(1-methylpiperidin-4-yl)-2-(pyridin-3-yl)-9H-purin-6-ylamino)ethyl)phenol; 4-(2-(9-(piperidin-4-yl)-2-(pyridin-3-yl)-9H-purin-6-ylamino)ethyl)phenol; N-(2-(1H-indazol-5-yl)ethyl)-9-isopropyl-2-(pyridin-3-yl)-9H-purin-6-amine; N-(2-(1H-benzo[d]imidazol-5-yl)ethyl)-9-isopropyl-2-(pyridin-3-yl)-9H-purin-6-amine; 5-(2-(9-isopropyl-2-(pyridin-3-yl)-9H-purin-6-ylamino)ethyl)indolin-2-one; 4-(2-(9-cyclopropyl-2-(pyridin-3-yl)-9H-purin-6-ylamino)ethyl)phenol; 4-(2-(9-(1-hydroxypropan-2-yl)-2-(pyridin-3-yl)-9H-purin-6-ylamino)ethyl)phenol; 4-(2-(9-isopropyl-2-(pyridin-3-yl)-9H-purin-6-ylamino)ethyl)phenyl sulfamate; 2-(4-hydroxyphenyl)-N-(9-isopropyl-2-(pyridin-3-yl)-9H-purin-6-yl)acetamide; 4-(5-(9-isopropyl-2-(pyridin-3-yl)-9H-purin-6-ylamino)isoxazol-3-yl)phenol; 4-(5-(9-isopropyl-2-(pyridin-3-yl)-9H-purin-6-ylamino)-1,3,4-oxadiazol-2-yl)phenol; 4-(2-(2-(2-fluoropyridin-3-yl)-9-isopropyl-9H-purin-6-ylamino)ethyl)phenol; 4-(2-(9-isopropyl-2-(1-methyl-1H-pyrrol-2-yl)-9H-purin-6-ylamino)ethyl)phenol; and 4-(2-(9-isopropyl-2-(thiazol-5-yl)-9H-purin-6-ylamino)ethyl)phenol.

In another embodiment is a compound of formula 1f:

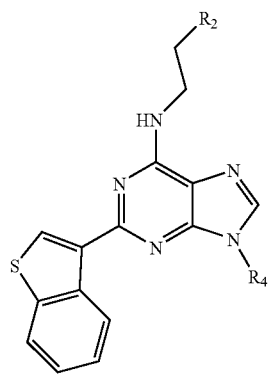

If in which: $R_2$ is selected from 1H-indol-3-yl and phenyl optionally substituted with hydroxy; and $R_4$ is selected from isopropyl, sec-butyl, benzhydryl, nonan-2-yl, oxetan-3-yl and tetrahydrofuran-3-yl.

In a further embodiment are compounds selected from: 4-(2-(2-(benzo[b]thiophen-3-yl)-9-isopropyl-9H-purin-6-ylamino)ethyl)phenol; 4-(2-(2-(benzo[b]thiophen-3-yl)-9-sec-butyl-9H-purin-6-ylamino)ethyl)phenol; 4-(2-(9-benzhydryl-2-(benzo[b]thiophen-3-yl)-9H-purin-6-ylamino)ethyl)phenol; N-(2-(1H-indol-3-yl)ethyl)-2-(benzo[b]thiophen-3-yl)-9-isopropyl-9H-purin-6-amine; 4-(2-(2-(benzo[b]thiophen-3-yl)-9-(nonan-2-yl)-9H-purin-6-ylamino)ethyl)phenol; N-(2-(1H-indol-3-yl)ethyl)-2-(benzo[b]thiophen-3-yl)-9-sec-butyl-9H-purin-6-amine; 4-(2-(2-(benzo[b]thiophen-3-yl)-9-(oxetan-3-yl)-9H-purin-6-ylamino)ethyl)phenol; (S)-4-(2-(2-(benzo[b]thiophen-3-yl)-9-(tetrahydrofuran-3-yl)-9H-purin-6-ylamino)ethyl)phenol; and (R)-4-(2-(2-(benzo[b]thiophen-3-yl)-9-(tetrahydrofuran-3-yl)-9H-purin-6-ylamino)ethyl)phenol.

In another embodiment is a compound of formula Ig:

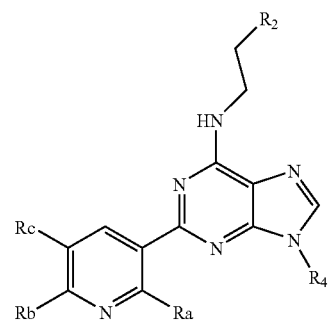

Ig in which: $R_2$ is selected from: 1H-pyrrolo[2,3-b]pyridin-3-yl; 1H-indol-3-yl optionally substituted with 1 to 2 radicals independently selected from halo, methyl and methoxy; and phenyl optionally substituted with 1 to 2 radicals independently selected from methyl, halo and hydroxy; $R_4$ is selected from isopropyl, sec-butyl, 1-hydroxypropan-2-yl, prop-1-en-2-yl, benzhydryl, nonan-2-yl, oxetan-3-yl and tetrahydrofuran-3-yl; and Ra, Rb and Rc are independently selected from hydrogen, cyano, methyl, halo, —$SO_2CH_3$ and trifluoromethyl.

In a further embodiment are compounds selected from: 4-(2-(9-isopropyl-2-(pyridin-3-yl)-9H-purin-6-ylamino) ethyl)phenol; 4-(2-(2-(6-fluoropyridin-3-yl)-9-isopropyl-9H-purin-6-ylamino)ethyl)phenol; 4-(2-(9-isopropyl-2-(4-methylpyridin-3-yl)-9H-purin-6-ylamino)ethyl)phenol; 5-(6-(4-hydroxyphenethylamino)-9-isopropyl-9H-purin-2-yl)nicotinonitrile; 4-(2-(9-isopropyl-2-(5-methylpyridin-3-yl)-9H-purin-6-ylamino)ethyl)phenol; 4-(2-(9-isopropyl-2-(5-(methylsulfonyl)pyridin-3-yl)-9H-purin-6-ylamino) ethyl)phenol; 4-(2-(2-(4-chloropyridin-3-yl)-9-isopropyl-9H-purin-6-ylamino)ethyl)phenol; 4-(2-(2-(5-fluoropyridin-3-yl)-9-isopropyl-9H-purin-6-ylamino)ethyl)phenol; 9-isopropyl-N-(2-(6-methoxy-1H-indol-3-yl)ethyl)-2-(pyridin-3-yl)-9H-purin-6-amine; 9-isopropyl-N-(2-(5-methyl-1H-indol-3-yl)ethyl)-2-(pyridin-3-yl)-9H-purin-6-amine; N-(2-(1H-indol-3-yl)ethyl)-9-isopropyl-2-(pyridin-3-yl)-9H-purin-6-amine; 4-(2-(9-(oxetan-3-yl)-2-(pyridin-3-yl)-9H-purin-6-ylamino)ethyl)phenol; 4-(2-(9-(1-hydroxypropan-2-yl)-2-(pyridin-3-yl)-9H-purin-6-ylamino)ethyl) phenol; 4-(2-(2-(2-fluoropyridin-3-yl)-9-isopropyl-9H-purin-6-ylamino)ethyl)phenol; 5-(9-sec-butyl-6-(4-hydroxy-3-methylphenethylamino)-9H-purin-2-yl)nicotinonitrile; 4-(2-(2-(5-fluoropyridin-3-yl)-9-(oxetan-3-yl)-9H-purin-6-ylamino)ethyl)phenol; 4-(2-(2-(5-chloropyridin-3-yl)-9-isopropyl-9H-purin-6-ylamino)ethyl)phenol; 4-(2-(9-isopropyl-2-(5-(trifluoromethyl)pyridin-3-yl)-9H-purin-6-ylamino)ethyl)phenol; 5-(6-(2-(1H-indol-3-yl)ethylamino)-9-sec-butyl-9H-purin-2-yl)nicotinonitrile; N-(2-(1H-indol-3-yl)ethyl)-9-sec-butyl-2-(5-methylpyridin-3-yl)-9H-purin-6-amine; (R)—N-(2-(1H-indol-3-yl)ethyl)-9-sec-butyl-2-(5-fluoropyridin-3-yl)-9H-purin-6-amine; (S)—N-(2-(1H-indol-3-yl)ethyl)-9-sec-butyl-2-(5-fluoropyridin-3-yl)-9H-purin-6-amine; N-(2-(1H-indol-3-yl)ethyl)-9-sec-butyl-2-(5-fluoropyridin-3-yl)-9H-purin-6-amine; (R)—N-(2-(1H-indol-3-yl)ethyl)-9-sec-butyl-2-(5-methylpyridin-3-yl)-9H-purin-6-amine; (S)—N-(2-(1H-indol-3-yl)ethyl)-9-sec-butyl-2-(5-methylpyridin-3-yl)-9H-purin-6-amine; 5-(6-(4-hydroxyphenethylamino)-9-(oxetan-3-yl)-9H-purin-2-yl) nicotinonitrile; 4-(2-(6-(5-fluoropyridin-3-yl)-1-isopropyl-1H-pyrazolo[3,4-d]pyrimidin-4-ylamino)ethyl)phenol; 3-(6-(4-hydroxyphenethylamino)-9-isopropyl-9H-purin-2-yl) isonicotinonitrile; 4-(2-(2-(5-fluoropyridin-3-yl)-7-isopropyl-7H-pyrrolo[2,3-d]pyrimidin-4-ylamino)ethyl) phenol; 4-(2-(9-isopropyl-2-(6-methylpyridin-3-yl)-9H-purin-6-ylamino)ethyl)phenol; 2-chloro-4-(2-(9-isopropyl-2-(pyridin-3-yl)-9H-purin-6-ylamino)ethyl)phenol; 3-fluoro-4-(2-(9-isopropyl-2-(pyridin-3-yl)-9H-purin-6-ylamino)ethyl)phenol; N-(2-(5-fluoro-1H-indol-3-yl)ethyl)-9-isopropyl-2-(pyridin-3-yl)-9H-purin-6-amine; N-(2-(5-chloro-1H-indol-3-yl)ethyl)-9-isopropyl-2-(pyridin-3-yl)-9H-purin-6-amine; 4-(2-(9-isopropyl-2-(pyridin-3-yl)-9H-purin-6-ylamino)ethyl)-2-methylphenol; 2-(6-(2-(1H-indol-3-yl)ethylamino)-2-(5-fluoropyridin-3-yl)-9H-purin-9-yl) propan-1-ol; (R)-2-(6-(2-(1H-indol-3-yl)ethylamino)-2-(5-fluoropyridin-3-yl)-9H-purin-9-yl)propan-1-ol; (S)-2-(6-(2-(1H-indol-3-yl)ethylamino)-2-(5-fluoropyridin-3-yl)-9H-purin-9-yl)propan-1-ol; (R)—N-(2-(1H-indol-3-yl)ethyl)-2-(5-fluoropyridin-3-yl)-9-(tetrahydrofuran-3-yl)-9H-purin-6-amine; 4-(2-(6-(5-fluoropyridin-3-yl)-1-isopropyl-1H-imidazo[4,5-c]pyridin-4-ylamino)ethyl)phenol; N-(2-(1H-indol-3-yl)ethyl)-2-(5-fluoropyridin-3-yl)-9-isopropyl-9H-purin-6-amine; 2-(5-fluoropyridin-3-yl)-9-isopropyl-N-(2-(6-methoxy-1H-indol-3-yl)ethyl)-9H-purin-6-amine; 2-(5-fluoropyridin-3-yl)-9-isopropyl-N-(2-(5-methoxy-1H-indol-3-yl)ethyl)-9H-purin-6-amine; N-(2-(1H-indol-3-yl) ethyl)-2-(5-fluoropyridin-3-yl)-9-(prop-1-en-2-yl)-9H-purin-6-amine; N-(2-(1H-pyrrolo[2,3-b]pyridin-3-yl)ethyl)-2-(5-fluoropyridin-3-yl)-9-isopropyl-9H-purin-6-amine; 4-(2-(5-(5-fluoropyridin-3-yl)-3-isopropyl-3H-imidazo[4,5-b]pyridin-7-ylamino)ethyl)phenol; N-(2-(1H-indol-3-yl) ethyl)-9-isopropyl-2-(5-methylpyridin-3-yl)-9H-purin-6-amine; 2-(5-fluoropyridin-3-yl)-9-isopropyl-N-(2-(7-methyl-1H-indol-3-yl)ethyl)-9H-purin-6-amine; N-(2-(1H-indol-3-yl)ethyl)-2-(5-fluoropyridin-3-yl)-9-(oxetan-3-yl)-9H-purin-6-amine; N-(2-(1H-indol-3-yl)ethyl)-2-(5-methylpyridin-3-yl)-9-(oxetan-3-yl)-9H-purin-6-amine; N-(2-(6-fluoro-1H-indol-3-yl)ethyl)-2-(5-fluoropyridin-3-yl)-9-isopropyl-9H-purin-6-amine; 2-(5-fluoropyridin-3-yl)-9-isopropyl-N-(2-(2-methyl-1H-indol-3-yl)ethyl)-9H-purin-6-amine; 2-(5-fluoropyridin-3-yl)-9-isopropyl-N-(2-(6-methyl-1H-indol-3-yl)ethyl)-9H-purin-6-amine; N-(2-(4-fluoro-1H-indol-3-yl)ethyl)-2-(5-fluoropyridin-3-yl)-9-isopropyl-9H-purin-6-amine; 2-(5-fluoropyridin-3-yl)-9-isopropyl-N-(2-(4-methyl-1H-indol-3-yl)ethyl)-9H-purin-6-amine; N-(2-(7-fluoro-1H-indol-3-yl)ethyl)-2-(5-fluoropyridin-3-yl)-9-isopropyl-9H-purin-6-amine; and 4-(2-(2-(5-fluoropyridin-3-yl)-9-(1-hydroxypropan-2-yl)-9H-purin-6-ylamino)ethyl)-2-methylphenol.

In another embodiment is a method of using a compound of Formula I to stimulate the expansion of stem cells by increasing the number of divisions; said method comprising contacting the stem cells with a compound of Formula I.

In another embodiment is a method in which the expansion of stem cells is in vivo, in vitro, or ex vivo.

In another embodiment is a method in which the stem cells are human hematopoietic stem cells.

In another embodiment is a cell population with expanded hematopoietic stem cells, as obtained or obtainable by the method of the invention.

In a further embodiment is a composition comprising a cell population with expanded HSCs derived from one or two cord blood units, preferably one cord blood unit, wherein said composition contains a total amount of cells of at least $10^5$ cells, $10^7$ cells, $10^8$ cells or $10^9$ cells, and wherein between 20-100% of total cells are CD34+ cells, for example between 40-80% of total cells are CD34+.

In another embodiment is a method for treating a disease or disorder for which stem cell therapy would result in the prevention, treatment or eradication of said disorder.

It is anticipated that as stem cell use progresses the diseases that can be treated by stem cell transplantation will expand. A non-limiting list of examples follows, infra.

In another embodiment is the use of a compound of Formula I as defined in the Summary of the Invention, or a salt thereof, in the preparation of a composition for the treatment of an inherited immunodeficient disease, an autoimmune disease and/or a hematopoietic disorder.

In a further embodiment, the administration is an autologous transplantation and the hematopoietic disorder is selected from Multiple myeloma, Non-Hodgkin lymphoma, Hodgkin disease, Acute myeloid leukemia, Neuroblastoma, Germ cell tumors, Autoimmune disorders and Amyloidosis.

In a further embodiment, the autoimmune disorders are selected from Systemic lupus erythematosus (SLE) and systemic sclerosis.

In a further embodiment, the administration is an allogeneic transplantation and the hematopoietic disorder is selected from Acute myeloid leukemia, Acute lymphoblastic leukemia, Chronic myeloid leukemia, Chronic lymphocytic leukemia, Myeloproliferative disorders, Myelodysplastic syndromes, Multiple myeloma, Non-Hodgkin lymphoma, Hodgkin disease, Aplastic anemia, Pure red cell aplasia, Paroxysmal nocturnal hemoglobinuria, Fanconi anemi, Thalassemia major, Sickle cell anemia, Severe combined immunodeficiency (SCID), Wiskott-Aldrich syndrome, Hemophagocytic lymphohistiocytosis (HLH) and inborn errors of metabolism.

In a further embodiment, the inborn errors of metabolism are selected from mucopolysaccharidosis, Gaucher disease, metachromatic leukodystrophies and adrenoleukodystrophies.

In another embodiment is a method for treating an inherited immunodeficient disease, an autoimmune disease and/or a hematopoietic disorder comprising administration to a patient in need of such treatment hematopoietic stem cells expanded by a compound as described in the Summary of the Invention.

In a further embodiment, the administration is an autologous transplantation and the hematopoietic disorder is selected from Multiple myeloma, Non-Hodgkin lymphoma, Hodgkin disease, Acute myeloid leukemia, Neuroblastoma, Germ cell tumors, Autoimmune disorders and Amyloidosis.

In a further embodiment, the autoimmune disorders are selected from Systemic lupus erythematosus (SLE) and systemic sclerosis.

In a further embodiment, the administration is an allogeneic transplantation and the hematopoietic disorder is selected from Acute myeloid leukemia, Acute lymphoblastic leukemia, Chronic myeloid leukemia, Chronic lymphocytic leukemia, Myeloproliferative disorders, Myelodysplastic syndromes, Multiple myeloma, Non-Hodgkin lymphoma, Hodgkin disease, Aplastic anemia, Pure red cell aplasia, Paroxysmal nocturnal hemoglobinuria, Fanconi anemi, Thalassemia major, Sickle cell anemia, Severe combined immunodeficiency (SCID), Wiskott-Aldrich syndrome, Hemophagocytic lymphohistiocytosis (HLH) and inborn errors of metabolism.

In a further embodiment, the inborn errors of metabolism are selected from mucopolysaccharidosis, Gaucher disease, metachromatic leukodystrophies and adrenoleukodystrophies.

Utility

HSCs are primitive cells capable of regenerating all blood cells. During development, hematopoiesis translocates from the fetal liver to the bone marrow, which then remains the site of hematopoiesis throughout adulthood. Once hematopoiesis has been established in the bone marrow, the HSCs are not distributed randomly throughout the bone cavity. Instead, they are found in close proximity to the endosteal surfaces. The more mature stem cells increase in number as the distance from the bone surface increases. Finally, as the central longitudinal axis of the bone is approached terminal differentiation of mature cells occurs.

Expanding the number of stem cells, whether from adult, umbilical cord blood, fetal, or embryonic sources, would have a huge impact on transplantation and other therapies for hematology and oncology diseases and disorders, the least of which would be increased safety and reduced costs. As described in the methods herein, HSC numbers are increased ex vivo. A method of increasing stem cell numbers is important as currently, approximately 25% of autologous donor transplants are prohibited for lack of sufficient stem cells. In addition, less than 25% of patients in need of allogeneic transplant can find a histocompatible donor. Umbilical cord blood banks currently exist and cover the broad racial makeup of the general population, but these banks are currently restricted to use in children due to inadequate stem cell numbers in the specimens for adult recipients. A method to increase stem cell numbers permits cord blood to be useful for adult patients, thereby expanding the use of allogeneic transplantation. Compounds of the invention can also be used to expand the progenitor cell numbers which are clinically useful, for example, to speed engraftment and decrease the duration of neutopenia.

Accordingly, a method for increasing the number of HSCs is provided. As used herein, an increase in HSCs means that the subject has at least one more HSC, a 10% increase, a 20% increase, a 30% increase or greater. HSCs may consist of a subset of CD34+ cells, increase of HSCs can be measured indirectly by counting the number of CD34+ cells in a cell population and, optionally, by assessing the differentiation properties of the CD34+ cells by analyzing the colony forming units (CFU) as described in the experimental part below: An increase of the number of CD34+ cells culture of a least 10%, preferably 20% increase or 30% increase or greater as compared with a control without expansion is indicative of HSC expansion. The expanded population of HSCs is harvested, for example, from a bone marrow sample of a subject or from a culture. Harvesting HSCs is defined as the dislodging or separation of cells. This is accomplished using a number of methods, such as enzymatic, non-enzymatic, centrifugal, electrical, or size-based methods, or preferably, by flushing the cells using culture media (e.g., media in which cells are incubated) or buffered solution. The cells are optionally collected, separated, and further expanded generating even larger populations of HSCs and differentiated progeny.

A method for making an expanded population of HSCs comprises contacting an agent capable of down-regulating the activity and/or expression of AHR and/or a downstream effector of AHR, e.g., a compound of the invention, with a starting cell population (i.e., an unexpanded population of cells) comprising a mixture of HSCs and optionally HSC supporting cells. The administration step occurs ex vivo, in vivo and/or in vitro. As described herein, the expanded population of HSCs is optionally administered to a subject. For ex vivo expansion, such agent for HSC expansion, e.g. a compound of the invention, may be formulated in DMSO or some other suitable carrier, "washed" from the cells and the cells may be transferred, for example, into an infusion buffer. A DMSO formulation, for example, can contain 0.3 mg/ml of a compound of the invention in 60% DMSO/40% water solution. Thus, provided are methods of providing an expanded population of HSCs to a subject comprising administering to the subject the expanded population of HSCs described herein or made by the methods described herein. The expanded population of HSCs is optionally used to make blood cells. The blood cells are optionally administered to a subject in need. Optionally, the subject is the same subject from which the unexpanded population of HSCs or mixture of HSCs and HSC supporting cells was derived.

As used herein, the term HSC supporting cell refers to cells naturally found in the vicinity of one or more HSCs such that factors released by HSC supporting cells reach the HSC by diffusion, for example. HSC supporting cells include, but are not limited to, lymphoreticular stromal cells. Lymphoreticular stromal cells as used herein include, but are not limited to, all cell types present in a lymphoid tissue which are not lymphocytes or lymphocyte precursors or progenitors. Thus, lymphoreticular stromal cells include osteoblasts, epithelial cells, endothelial cells, mesothelial cells, dendritic cells, splenocytes and macrophages. Lymphoreticular stromal cells also include cells that would not ordinarily function as lymphoreticular stromal cells, such as fibroblasts, which have been genetically altered to secrete or express on their cell surface the factors necessary for the maintenance, growth or differentiation of HSCs, including their progeny. Lymphoreticular stromal cells are optionally derived from the disaggregation of a piece of lymphoid tissue. Such cells are capable of supporting in vitro or in vivo the maintenance, growth or differentiation of HSCs, including their progeny. By lymphoid tissue it is meant to include bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. Lymphoid soft tissue as used herein includes, but is not limited to, tissues such as thymus, spleen, liver, lymph node, skin, tonsil, adenoids and Peyer's patch, and combinations thereof.

Lymphoreticular stromal cells provide the supporting microenvironment in the intact lymphoid tissue for the maintenance, growth or differentiation of HSCs, including their progeny. The microenvironment includes soluble and cell surface factors expressed by the various cell types which comprise the lymphoreticular stroma. Generally, the support which the lymphoreticular stromal cells provide is characterized as both contact-dependent and non-contact-dependent.

Lymphoreticular stromal cells, for example, are autologous (self) or non-autologous (non-self, e.g., heterologous, allogeneic, syngeneic or xenogeneic) with respect to HSCs. Autologous, as used herein, refers to cells from the same subject. Allogeneic, as used herein, refers to cells of the same species that differ genetically. Syngeneic, as used herein, refers to cells of a different subject that are genetically identical to the cell in comparison. Xenogeneic, as used herein, refers to cells of a different species. Lymphoreticular stroma cells are obtained, for example, from the lymphoid tissue of a human or a non-human subject at any time after the organ/tissue has developed to a stage (i.e., the maturation stage) at which it can support the maintenance, growth or differentiation of HSCs. The lymphoid tissue from which lymphoreticular stromal cells are derived usually determines the lineage-commitment HSCs undertake, resulting in the lineage-specificity of the differentiated progeny.

The co-culture of HSCs (and progeny thereof) with lymphoreticular stromal cells, usually occurs under conditions known in the art (e.g., temperature, $CO_2$ and $O_2$ content, nutritive media, duration, etc.). The time sufficient to increase the number of cells is a time that can be easily determined by a person skilled in the art, and varies depending upon the original number of cells seeded. The amounts of HSCs and lymphoreticular stromal cells initially introduced (and subsequently seeded) varies according to the needs of the experiment. The ideal amounts are easily determined by a person skilled in the art in accordance with needs.

As used throughout, by a subject is meant an individual. Thus, subjects include, for example, domesticated animals, such as cats and dogs, livestock (e.g., cattle, horses, pigs, sheep, and goats), laboratory animals (e.g., mice, rabbits, rats, and guinea pigs), mammals, non-human mammals, primates, non-human primates, rodents, birds, reptiles, amphibians, fish, and any other animal. The subject is optionally a mammal such as a primate or a human.

Methods for Expanding Hematopoietic Stem Cells

The invention therefore relates to a method for expanding hematopoietic stem cells, comprising (a) providing a starting cell population comprising hematopoietic stem cells and (b) culturing said starting cell population ex vivo in presence of an agent capable of down-regulating the activity and/or expression of aryl hydrocarbon receptor and/or a down-stream effector of aryl hydrocarbon receptor pathway, under suitable conditions for expanding hematopoietic stem cells.

The aryl hydrocarbon (dioxin) receptor (AHR) is a cytosolic ligand-activated transcription factor known to mediate a large number of toxic and carcinogenic effects in animals and possible in human (Safe S 2001 Toxicol Lett 120: 1-7). As a consequence of AHR activation by its ligands, many detoxification genes are transcriptionally induced, including those coding for phase I xenobiotic-metabolizing enzymes, such as the cytochromes P450 CYP1A1, CYP1A2, CYP1B1 and CYP2S1, and the phase II enzymes UDP-glucuronosyltransferase UGT1A6, NAD(P)H-dependent quinone oxidoreductase-1 (NQO1), the aldehyde dehydrogenase ALDH3A1, and several glutathione-5-transferase.

In one embodiment, an agent capable of down-regulating the activity and/or expression of aryl hydrocarbon receptor and/or a down-stream effector of aryl hydrocarbon receptor pathway is selected among the group consisting of: (i) an organic compound; (ii) a small interference RNA (siRNA) molecule capable of down-regulating the expression of AHR; and (iii) antisense oligonucleotide capable of down-regulating the expression of AHR.

In one specific embodiment, said method for expanding hematopoietic stem cells, comprises (a) providing a starting cell population comprising hematopoietic stem cells and (b) culturing said starting cell population ex vivo in the presence of an agent capable of down-regulating the activity and/or expression of aryl hydrocarbon receptor and/or a down-stream effector of aryl hydrocarbon receptor pathway, under suitable conditions for expanding hematopoietic stem cells, wherein said agent capable of down-regulating the activity and/or expression of aryl hydrocarbon receptor and/or a down-stream effector of aryl hydrocarbon receptor pathway is not alpha-napthoflavone or 3'-methoxy-4'-nitroflavone.

Organic compound that inhibits AHR activity (also referred herein as AHR antagonist) have been described in the art, for example 2-methyl-2H-pyrazole-3-carboxylic acid (2-methyl-4-o-tolylazophenyl)amide (CH223191), alpha napthoflavone, resveratrol (Nutr. Metab. Cardiovasc. Dis., 2003 April; 13(2):104-13), 3'-methoxy-4'-nitroflavone (Biochem. Pharmacol., 2007 May 15; 73(10):1622-34, Epub 2007 Jan. 30), and 6-methyl-1,3,8-trichlorodibenzofuran (Cancer Res., 2004, Apr. 15; 64(8):2889-97). An inhibitor of AHR activity refers to a compound which decreases AHR activity to at least 10%, 20%, 30%, 50%, 60%, 70%, 80% or at least 90% the transcriptional activity of AHR as observed under activated conditions. An assay to measure AHR inhibitory activity is for example the dioxin-induced AHR dependent luciferase reporter gene assay as described in the Examples. In one embodiment, an inhibitor of AHR activity is a compound that has an EC50 of less than 10 µM, preferably less than 5 µM as measured in the dioxin-induced AHR dependent luciferase reporter gene assay.

AHR is a transcriptional factor regulating the transcription of various genes in human. In one embodiment, a downstream effector of AHR pathway is a gene which is directly regulated at the transcriptional level by AHR. Examples of such genes are selected from Cyp1B1, Cyp1A1, and AHRR. AHR also functions in pathways outside of its well-characterized role in xenobiotic enzyme induction. Xenobiotic ligands of AHR have been shown to regulate beta catenin, STAT5, STAT1, HES-1, c-Myc, C/EBP, PU.1, β-catenin, p21, P27, pRb, deoxynucleotidyl transferase, CXCR4, and its chemokine ligand CXCL12 (SDF-1).

In one specific embodiment, an agent capable of down-regulating the activity and/or expression of aryl hydrocarbon receptor is a compound as defined in the Summary of the Invention.

In another embodiment, an agent capable of down-regulating the activity and/or expression of aryl hydrocarbon receptor is an antisense oligonucleotide or a small interfering RNA molecule (siRNA), capable of down-regulating AHR protein expression or the protein expression of one more down-stream effectors of AHR.

Design of antisense oligonucleotides which can be used to efficiently inhibit the AHR protein expression must be effected in a way that such oligonucleotides specifically binds the designated mRNA within cells in a way which inhibits translation thereof. Sequence suitable for use in design and synthesis of antisense oligonucleotides which specifically bind to AHR mRNA, genomic DNA and/or its promoter or other control sequences are available in published sequence of AHR, in particular human AHR. In addition, algorithms for identifying sequences with the highest predicted binding affinity for their target mRNA based on thermodynamic cycle that accounts for the energetics of structural alterations in both the target mRNA and the oligonucleotides are also available.

Synthesis of RNAi molecules suitable for use with the present invention can be affected as follows: First, the AHR mRNA sequence (or one or more of its down-stream effectors) is scanned downstream of the AUG start codon for AA-dinucleotide sequences. Occurrence of each AA and the 19 3'-adjacent is recorded as a potential siRNA target site. Then, potential target sites are compared to an appropriate genomic database (e.g, human, mouse, rat, etc.) using any sequence alignment software. Putative target site that exhibit significant homology to other coding sequences are filtered out. Preferred sequences are then those including low G/C content, in particular sequences with G/C content lower than 55%. Several target sites are then selected along the length of the target gene. Methods or algorithms to identify putative target site of siRNA are described for example in (Tilesi, et al., Curr. Opin. Mol. Ther. 11:156, 2009). Examples of siRNA molecules which are capable of down-regulating the expression of AHR are: AHR 111S, 5' GCG GCA TAG AGA CCG ACT TAA TTT CAA GAG AAT TAA GTC GGT CTC TAT GCC GCT TTT TTG G 3' (SEQ ID NO: 1); AHR 111AS, 5' CGC GCC AAA AAA GCG GCA TAG AGA CCG ACT TAA TTC TCT TGA AAT TAA GTC GGT CTC TAT GCC GC 3'(SEQ ID NO: 2); AHR 242S, 5' GGC TTC TTT GAT GTT GCA TTA ATT CAA GAG ATT AAT GCA ACA TCA AAG AAG CCT TTT TTG G 3'(SEQ ID NO: 3); AHR 242AS, 5' CGC GCC AAA AAA GGC TTC TTT GAT GTT GCA TTA ATC TCT TGA ATT AAT GCA ACA TCA AAG AAG CC 3'(SEQ ID NO: 4).

The starting cell population comprising hematopoietic stem cells will be selected by the person skilled in the art depending on the envisaged use. Various sources of cells comprising hematopoietic stem cells have been described in the art, including bone marrow, peripheral blood, neonatal umbilical cord blood, placenta or other sources such as liver, particularly fetal liver.

The cell population may first be subjected to enrichment or purification steps, including negative and/or positive selection of cells based on specific cellular markers in order to provide the starting cell population. Methods for isolating said starting cell population based on specific cellular markers may use fluorescent activated cell sorting (FACS) technology also called flow cytometry or solid or insoluble substrate to which is bound antibodies or ligands that interact with specific cell surface markers. For example, cells may be contacted with a solid substrate (e.g., column of beads, flasks, magnetic particles) containing the antibodies and any unbound cells are removed. When a solid substrate comprising magnetic or paramagnetic beads is used, cells bound to the beads can be readily isolated by a magnetic separator.

In one embodiment, said starting cell population is enriched in a desirable cell marker phenotype (e.g., CD34+, CD133+, CD90+) or based on efflux of dyes such as rhodamine, Hoechst or aldehyde dehydrogenase activity. In one specific embodiment, said starting cell population is enriched in CD34+ cells. Methods for enriching blood cell population in CD34+ cells include kits commercialized by Miltenyi Biotec (CD34+ direct isolation kit, Miltenyi Biotec, Bergisch, Gladbach, Germany) or by Baxter (Isolex 3000).

The amount of cord blood from a single birth is often inadequate to treat an adult or an older child. One advantage of the expansion methods using the compounds of the invention, or an agent capable of down-regulating the activity and/or expression of aryl hydrocarbon receptor and/or a downstream effector of aryl hydrocarbon receptor pathway, is that it enables the production of a sufficient amount of hematopoietic stem cells from only one cord blood unit.

Accordingly, in one embodiment, the starting cell population is derived from neonatal umbilical cord blood cells which have been enriched in CD34+ cells. In one related embodiment, said starting cell population is derived from one or two umbilical cord blood units.

In another embodiment, the starting cell population is derived from human mobilized peripheral blood cells which have been enriched in CD34+ cells. In one related embodiment, said starting cell population is derived from human mobilized peripheral blood cells isolated from only one patient.

Said starting cell population may preferably contain at least 50% CD34+ cells, in some embodiments, more than 90% of CD34+ cells, and may comprise between $10^5$ and $10^9$ nucleated cells.

The starting cell population may be used directly for expansion or frozen and stored for use at a later date.

Conditions for culturing the starting cell population for hematopoietic stem cell expansion will vary depending, inter alia, on the starting cell population, the desired final number of cells, and desired final proportion of HSCs.

In one specific embodiment, in particular, using a starting cell population from umbilical cord blood cells enriched in CD34+ cells, the culturing conditions comprises the use of other cytokines and growth factors, generally known in the art for hematopoietic stem cell expansion. Such cytokines and growth factors include without limitation IL-1, IL-3, IL-6, IL-11, G-CSF, GM-CSF, SCF, FIT3-L, thrombopoietin (TPO), erythropoietin, and analogs thereof. As used herein, "analogs" include any structural variants of the cytokines and growth factors having the biological activity as the naturally occurring forms, including without limitation, variants with enhanced or decreased biological activity when compared to the naturally occurring forms or cytokine receptor agonists such as an agonist antibody against the TPO receptor (for example, VB22B sc(Fv)2 as detailed in patent publication WO 2007/145227, and the like). Cytokine and growth factor combinations are chosen to expand HSC and progenitor cells while limiting the production of terminally differentiated cells. In one specific embodiment, one or more cytokines and growth factors are selected from the group consisting of SCF, Flt3-L and TPO. In one specific embodiment, at least TPO is used in a serum-free medium under suitable conditions for HSC expansion. In one related embodiment, a mixture of IL6, SCF, Flt3-L and TPO is used in the method for expanding HSCs in combination with the compound of the invention or an agent capable of down-regulating the activity and/or expression of aryl hydrocarbon receptor and/or a downstream effector of aryl hydrocarbon receptor pathway.

Human IL6 or interleukin-6, also known as B-cell stimulatory factor 2 has been described by (Kishimoto, Ann. review of 1 mm. 23:1 2005) and is commercially available. Human SCF or stem cell factor, also known as c-kit ligand, mast cell growth factor or Steel factor has been described (Smith, M A et al., ACTA Haematologica, 105, 3:143, 2001) and is commercially available. Flt3-L or FLT-3 Ligand, also referred as FL is a factor that binds to flt3-receptor. It has been described (Hannum C, Nature 368 (6472): 643-8) and is commercially available. TPO or thrombopoietin, also known as megakaryocyte growth factor (MGDF) or c-Mpl ligand has been described (Kaushansky K (2006). N. Engl. J. Med. 354 (19): 2034-45) and is commercially available.

The expansion of HSC may be carried out in a basal medium, which is supplemented with the mixtures of cytokines and growth factors described above. A basal medium typically comprises amino acids, carbon sources, vitamins, serum proteins (e.g. albumin), inorganic salts, divalent cations, buffers and any other element suitable for use in expansion of HSC. Examples of such basal medium appropriate for a method of expanding HSC include, without limitation, StemSpan® SFEM—Serum-Free Expansion Medium (StemCell Technologies, Vancouver, Canada), StemSpan® H3000—Defined Medium (StemCell Technologies, Vancouver, Canada), CellGro® SCGM (CellGenix, Freiburg Germany), StemPro®-34 SFM (Invitrogen).

In one embodiment, the compound of the invention or the agent capable of down-regulating the activity and/or expression of aryl hydrocarbon receptor and/or a down-stream effector of aryl hydrocarbon receptor pathway, is administered during the expansion method of said starting cell population under a concentration appropriate for HSC expansion. In one specific embodiment, said compound or AhR modulating agent is administered at a concentration comprised between 1 pM and 100 µM, for example between 10 pM and 10 µM, or between 100 pM and 1 µM.

In one specific embodiment where starting cell population essentially consists of CD34+ enriched cells from one or two cord blood units, the cells are grown under conditions for HSC expansion from about 3 days to about 90 days, for example between 7 and 2 days and/or until the indicated fold expansion and the characteristic cell populations are obtained. In one specific embodiment, the cells are grown under conditions for HSC expansion not more than 21 days, 14 days or 7 days.

In one embodiment, the starting cell population is cultured during a time sufficient to reach an absolute number of CD34+ cells of at least $10^5$, $10^6$, $10^7$, $10^8$ or $10^9$ cells. In another embodiment, said starting cell population is cultured during a time sufficient for a 10 to 50000 fold expansion of CD34+ cells, for example between 100 and 10000 fold expansion.

The cell population obtained after the expansion method may be used without further purification or may be subject to further purification or selection steps.

The cell population may then be washed to remove the compound of invention or any other agent capable of down-regulating the activity and/or expression of aryl hydrocarbon receptor and/or a down-stream effector of aryl hydrocarbon receptor pathway and/or any other components of the cell culture and resuspended in an appropriate cell suspension medium for short term use or in a long-term storage medium, for example a medium suitable for cryopreservation.

Cell Population with Expanded HSCs as Obtained by the Expansion Method and Therapeutic Compositions The invention further provides a cell population with expanded HSCs, obtainable or obtained by the expansion method described above. In one specific embodiment, such cell population is resuspended in a pharmaceutically acceptable medium suitable for administration to a mammalian host, thereby providing a therapeutic composition.

The compound as defined in the Summary of the Invention or an agent capable of down-regulating the activity and/or expression of aryl hydrocarbon receptor and/or a down-stream effector of aryl hydrocarbon receptor pathway enables the expansion of HSCs, for example from only one or two cord blood units, to provide a cell population quantitatively and qualitatively appropriate for efficient short and long term engraftment in human patient in need thereof. In particular, the invention relates to a composition comprising a cell population with expanded HSCs derived from not more than one or two cord blood units, wherein said therapeutic composition contains a total amount of cells of at least $10^5$, $10^6$, $10^7$, $10^8$ or $10^9$ cells, with between 20-100%, for example between 40-80% of total cells being CD34+ cells. In one related embodiment, said composition contains between 0.1-40%, for example between 0.1-10% of total cells being CD34+ Thy1+ and 20-80% of cells being CD34+ CD45RA+. In some specific embodiments, said composition contains between 10-95% of cells being CD38+ and between 5-70% of cells being CD133+.

Use of Therapeutic Compositions

The invention further provides the cell population with expanded HSCs or its composition for use in allogeneic or autologous stem cell transplantation in a mammalian subject.

The subject referred to herein is, for example, a bone marrow donor or an individual with or at risk for depleted or limited blood cell levels. Optionally, the subject is a bone marrow donor prior to bone marrow harvesting or a bone marrow donor after bone marrow harvesting. The subject is optionally a recipient of a bone marrow transplant. The methods described herein are particularly useful in subjects that have limited bone marrow reserve such as elderly subjects or subjects previously exposed to an immune depleting treatment or myeloablative treatment such as chemotherapy, e.g., for treating leukemia or lymphomas. The subject, optionally, has a decreased blood cell level or is at risk for developing a decreased blood cell level as compared to a control blood cell level. As used herein the term control blood cell level refers to an average level of blood cells in a subject prior to or in the substantial absence of an event that changes blood cell levels in the subject. An event that changes blood cell levels in a subject includes, for example, anemia, trauma, chemotherapy, bone marrow transplant and radiation therapy. For example, the subject has anemia or blood loss due to, for example, trauma.

The expanded HSC population or the composition comprising the cell population with expanded HSCs is administered to the subject, for example, before, at the same time, or after chemotherapy, radiation therapy or a bone marrow transplant. The subject optionally has depleted bone marrow related to, for example, congenital, genetic or acquired syndrome characterized by bone marrow loss or depleted bone marrow. Thus, the subject is optionally a subject in need of hematopoiesis. Optionally, the subject is a bone marrow donor or is a subject with or at risk for depleted bone marrow.

Hematopoietic stem cell manipulation is useful as a supplemental treatment to chemotherapy or radiation therapy. For example, HSCs are localized into the peripheral blood and then isolated from a subject that will undergo chemotherapy, and after the therapy the cells are returned. Thus, the subject is a subject undergoing or expected to undergo an immune cell depleting treatment such as chemotherapy, radiation therapy or serving as a donor for a bone marrow transplant. Bone marrow is one of the most prolific tissues in the body and is therefore often the organ that is initially damaged by chemotherapy drugs and radiation. The result is that blood cell production is rapidly destroyed during chemotherapy or radiation treatment, and chemotherapy or radiation must be terminated to allow the hematopoietic system to replenish the blood cell supplies before a patient is re-treated with chemotherapy. Therefore, as described herein, HSCs or blood cells made by the methods described herein are optionally administered to such subjects in need of additional blood cells.

Provided are HSCs expanded by a compound of the invention or an agent capable of down-regulating the activity and/or expression of aryl hydrocarbon receptor and/or a downstream effector of aryl hydrocarbon receptor pathway or the compositions with expanded HSCs as described above in combination with a therapeutic capable of enhancing the proliferation of HSCs in vivo, in vitro, or ex vivo (for example, a small molecule, an antibody, or the like) and optionally at least one pharmaceutically acceptable excipient or carrier. By a therapeutic capable of enhancing HSC proliferation is meant: an agonist antibody against the TPO receptor (for example, VB22B sc(Fv)2 as detailed in patent publication WO 2007/145227, and the like); a cytokine such as SCF, IL-6, Flt-3 ligand, TPO or a TPO mimetic (for example, such as described in WO/2007/022269; WO/2007/009120; WO/2004/054515; WO/2003/103686; WO/2002/085343; WO/2002/049413; WO/2001/089457; WO/2001/039773; WO/2001/034585; WO/2001/021180; WO/2001/021180; WO/2001/017349; WO/2000/066112; WO/2000/035446; WO/2000/028987; WO/2008/028645; and the like); granulocyte colony stimulating factor (G-CSF); granulyte macrophage colony stimulating factor (GM-CSF); a prostaglandin or a prostaglandin receptor agonist (for example, prostaglandin E2 receptor-1 (EP-I) agonist, prostaglandin E2 receptor-2 (EP-2) agonist, prostaglandin E2 receptor-3 (EP-3) agonist and prostaglandin E2 receptor-4 (EP-4) agonists, as detailed in patent publication WO/2008/073748); tetraethylenepentamine (TEPA); Notch-ligands (Delta-1); and/or a WNT agonist. In addition, culturing stem cells with mesenchymal stem cells (MSCs) prevents graft-versus-host disease (GVHD) and may help stem cell expansion. MSCs and stem cells can be transplanted as a whole culture.

By pharmaceutically acceptable is meant a material that is not biologically or otherwise undesirable, i.e., the material may be administered to a subject or cell, without causing undesirable biological effects or interacting in a deleterious manner with the other components of the pharmaceutical composition in which it is contained. The carrier or excipient is selected to minimize degradation of the active ingredient and to minimize adverse side effects in the subject or cell.

The compositions are formulated in any conventional manner for use in the methods described herein. Administration is via any route known to be effective by one of ordinary skill. For example, the compositions is administered orally, parenterally (e.g., intravenously), by intramuscular injection, by intraperitoneal injection, transdermally, extracorporeally, intranasally or topically.

The preferred method of administration is intravenous infusion. The number of cells transfused will take into consideration factors such as sex, age, weight, the types of disease or disorder, stage of the disorder, the percentage of the desired cells in the cell population and the amount of cells needed to produce a therapeutic benefit. In one particular embodiment, the composition is administered by intravenous infusion and comprises at least $10^4$ cells/kg, from $10^5$ to $5.10^7$ cells/kg or more if necessary. In one specific embodiment, the infused cells are all deriving from expanded cord blood cells from a single birth.

A pharmaceutically acceptable carrier for infusion of a composition comprising cells into a patient typically comprise buffered saline with 5% HSA or unsupplemented basal medium or medium as known in the art.

For oral administration, the compositions take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets are coated by methods well known in the art. Liquid preparations for oral administration take the form of, for example, solutions, syrups or suspensions, or they may be presented as a dry product for constitution with water or other suitable vehicle before use. Such liquid preparations are prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations optionally contain buffer salts, flavoring, coloring and sweetening agents as appropriate.

The compositions are formulated for parenteral administration by injection, e.g., by bolus injection or continuous infusion. Formulations for injection are presented in unit dosage form, e.g., in ampules or in multi-dose containers, with or without an added preservative. The compositions take such forms as suspensions, solutions or emulsions in oily or aqueous vehicles, and may contain formulatory agents such as suspending, stabilizing and/or dispersing agents. Alternatively, the active ingredient is in powder form for constitution with a suitable vehicle, e.g., sterile pyrogen-free water, before use. In general, water, suitable oil, saline, aqueous dextrose (glucose), and related sugar solutions and glycols such as propylene glycol or polyethylene glycols are suitable carriers for parenteral solutions. Solutions for parenteral administration contain, for example, a water soluble salt of the active ingredient, suitable stabilizing agents and, if necessary, buffer substances. Antioxidizing agents such as sodium bisulfate, sodium sulfite or ascorbic acid, either alone or combined, are suitable stabilizing agents. Also citric acid and its salts and sodium ethylenediaminetetraacetic acid (EDTA) are optionally used. In addition, parenteral solutions optionally contain preservatives such as benzalkonium chloride, methyl- or propyl-paraben and chlorobutanol. Suitable pharmaceutical carriers are described in Remington: The Science and Practice of Pharmacy, 21st Edition, David B. Troy, ed., Lippicott Williams & Wilkins (2005), which is incorporated by reference in its entirety at least for the material related to pharmaceutical carriers and compositions.

The compositions are optionally formulated as a depot preparation. Such long acting formulations are optionally administered by implantation. Thus, for example, the compositions are formulated with suitable polymeric or hydrophobic materials (for example as an emulsion in an acceptable oil) or ion exchange resins, or as sparingly soluble derivatives, for example, as a sparingly soluble salt. The compositions are applied to or embedded with implants concurrent with or after surgical implant.

Additionally, standard pharmaceutical methods are employed to control the duration of action. These include control release preparations and appropriate macromolecules, for example, polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation are adjusted in order to control release. Optionally, the agent is incorporated into particles of polymeric materials such as polyesters, polyamino acids, hydrogels, poly (lactic acid) or ethylenevinylacetate copolymers. In addition to being incorporated, these agents are optionally used to trap the compound in microcapsules.

A composition for use in the methods described herein is optionally formulated as a sustained and/or timed release formulation. Such sustained and/or timed release formulations are made by sustained release means or delivery devices that are well known to those of ordinary skill in the art. The compositions are used to provide slow or sustained release of one or more of the active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable sustained release formulations are selected for use with the compositions described herein. Thus, single unit dosage forms suitable for oral administration, such as, but not limited to, tablets, capsules, gelcaps, caplets, powders that are adapted for sustained release are used.

The compositions are optionally delivered by a controlled-release system. For example, the composition is administered using intravenous infusion, an implantable osmotic pump, liposomes, or other modes of administration. A controlled release system is placed in proximity to the target.

Optionally, it is desirable to administer the composition locally, i.e., to the area in need of treatment. For example, the composition is administered by injection into the bone marrow of a long bone, for example. Local administration is achieved, for example, by local infusion during surgery, topical application (e.g., in conjunction with a wound dressing after surgery), injection, catheter, suppository, or implant. An implant is of a porous, non-porous, or gelatinous material, including membranes, such as sialastic membranes, or fibers.

The pharmaceutical compositions described herein are administered by any conventional means available for use in conjunction with pharmaceuticals, either as individual therapeutic active ingredients or in a combination of therapeutic active ingredients. They are optionally administered alone, but are generally administered with a pharmaceutical carrier selected on the basis of the chosen route of administration and standard pharmaceutical practice.

The compounds described herein are provided in a pharmaceutically acceptable form including pharmaceutically acceptable salts and derivatives thereof. The term pharmaceutically acceptable form refers to compositions including the compounds described herein that are generally safe, relatively non-toxic and neither biologically nor otherwise undesirable. These compositions optionally include pharmaceutically acceptable carriers or stabilizers that are nontoxic to the cell or subject being exposed thereto at the dosages and concentrations employed. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (Uniqema, United Kingdom), polyethylene glycol (PEG), and PLURONICS™ (BASF, Germany).

The term pharmaceutically acceptable acid salts and derivatives refers to salts and derivatives of the compounds of Formula I described herein that retain the biological effectiveness and properties as described, and that are not biologically or otherwise undesirable. Pharmaceutically acceptable salts are formed, for example, with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The chemical stability of a composition comprising a compound of Formula I or a pharmaceutically acceptable salt or ester thereof is enhanced by methods known to those of skill in the art. For example, an alkanoic acid ester of a polyethoxylated sorbitol (a polysorbate) is added to a composition containing a compound of Formula I in an amount effective to enhance the chemical stability of the compound.

The data obtained from the cell culture assays and animal studies are optionally used in formulating a range of dosage for use in humans. The dosage of such compounds lies preferably within a range of circulating concentrations that include little or no toxicity. The dosage varies within this range depending upon the dosage form employed and the route of administration utilized. For any compound used in the provided methods, the therapeutically effective dose is estimated initially from cell culture assays.

Also provided herein is a pack or kit comprising one or more containers filled with one or more of the ingredients described herein. Such kits optionally comprise solutions and buffers as needed or desired. The kit optionally includes an expanded population of stem cells made by the methods described above or can contain containers or compositions for making an expanded population of HSCs. In particular, the invention provides a kit for expanding ex vivo hematopoietic stem cells, comprising a compound as defined in the Summary of Invention and instructions for use of such compound in a method for HSC expansion and, optionally, one or more cytokines or growth factors, or media for cell growth, in particular media for hematopoietic stem cell growth as described above. The kit may further comprise antibodies for monitoring production of the cells, such as anti-CD34, anti-CD133, anti-CD38, anti-CD45RA and/or anti-Thy 1 antibodies. In one specific embodiment, such kit further include one or more cytokines or growth factors selected from the group consisting of IL6, FLT3-L, SCF and TPO. Optionally associated with such pack(s) or kit(s) are instructions for use.

Also provided is a kit for providing an effective amount of a compound of the invention to increase HSCs in a subject comprising one or more doses of the compound for use over a period of time, wherein the total number of doses of the compound of the invention in the kit equals the effective amount sufficient to increase HSCs in a subject. The period of time is from about one to several days or weeks or months. Thus, the period of time is from at least about 5, 6, 7, 8, 10, 12, 14, 20, 21, 30 or 60 days or more or any number of days between one and 90.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

The following reaction schemes 1-5 detail the preparation of compounds of the invention. It will be appreciated by one skilled in the art that, following introduction by the methods detailed below, any of the groups $R_1$, $R_2$, $R_3$, $R_4$, and $L_1$ may optionally be further elaborated by known transformations to arrive at the desired final compounds of Formula I.

Compounds of Formula I can be prepared according the following Reaction Scheme 1:

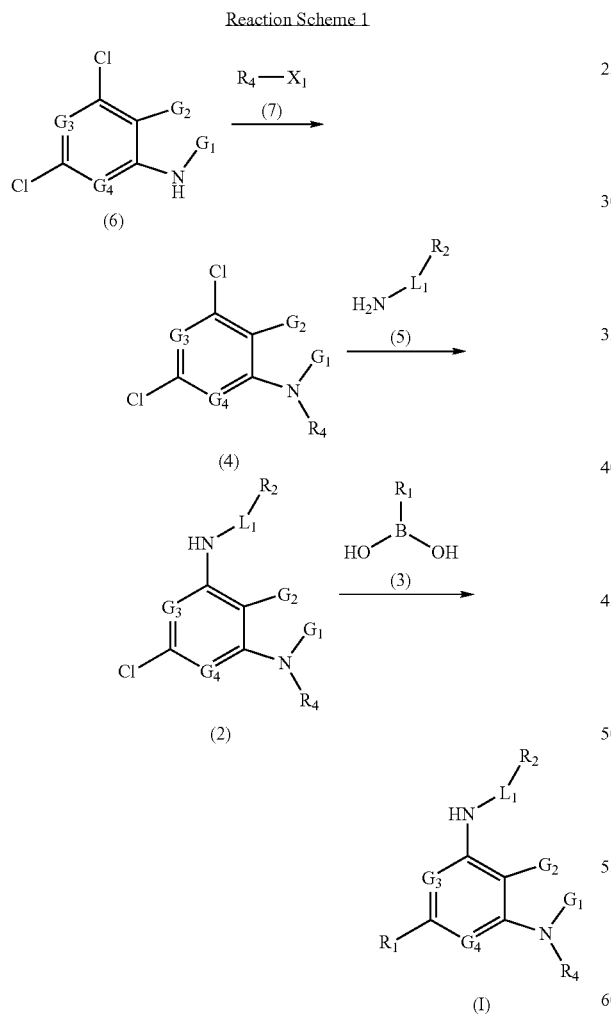

in which $G_1$, $G_2$, $G_3$, $G_4$, $R_1$, $R_2$ and $R_4$ are as defined for Formula I in the Summary of the Invention and L of Formula I is defined in the reaction scheme as —NH-$L_1$- which is equivalent to, for example, —NR$_{5a}$(CH$_2$)$_{0-3}$— where R$_{5a}$ is hydrogen and —(CH$_2$)$_{0-3}$— is $L_1$.

Compounds of Formula I can be prepared by reacting a compound of Formula 2 with a compound of Formula 3 in the presence of a suitable catalyst (e.g., Pd$_2$(dba)$_3$, or the like) in the presence of an appropriate ligand (e.g., 1,3-bis(2,4,6-trimethylphenyl)imidazolium chloride), a suitable base (e.g., Cs$_2$CO$_3$, or the like) and an appropriate solvent (e.g., 1,4-dioxane) at a temperature of about 80 to 100° C. for 2 to about 48 hours. Compounds of Formula 2 in turn can be prepared by reacting a compound of Formula 4 with a slight excess of an amine compound of Formula 5 in an appropriate solvent (e.g. isopropanol) at a temperature of about room temperature to about 80° C. Compounds of Formula 4 can be prepared by alkylation of a compound of Formula 6 with a suitable alkylating agent 7, in which $X_1$ is chlorine, bromine, iodine, or a sulfonate ester, in the presence of a suitable base (e.g. sodium hydride or potassium carbonate), in a suitable solvent (e.g. DMF), at a temperature of about 0° C. to about 80° C. Alternatively, the reaction can be performed under Mitsunobu conditions using a suitable alcohol $R_4$—OH in the presence of a suitable phosphine (e.g. triphenylphosphine) and azodicarboxylate (e.g. diethylazodicarboxylate), in an inert solvent such as THF or toluene, at a temperature from about 0° C. to about room temperature.

Compounds of Formula Ia, in which $G_1$ is $CR_3$ and in which all other G groups are N, can also be prepared by proceeding as in the following Reaction Scheme 2:

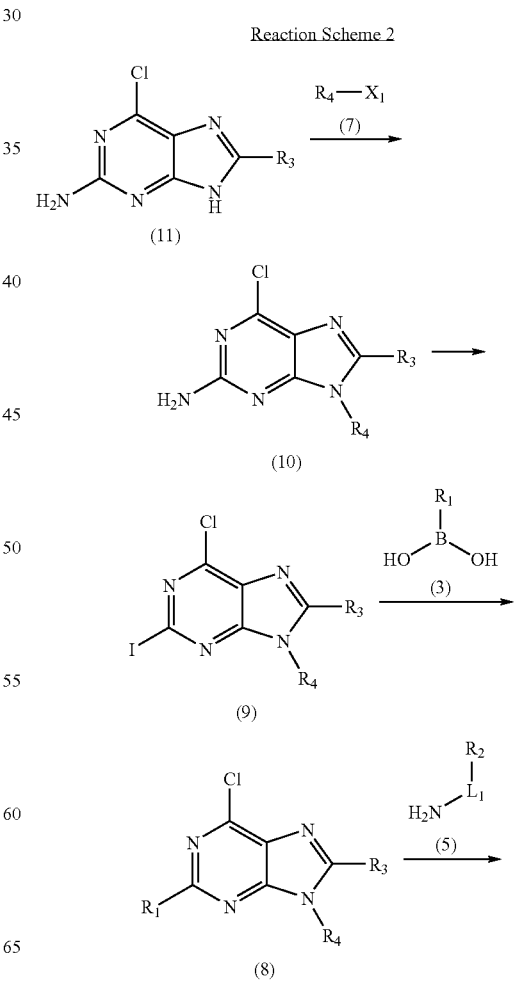

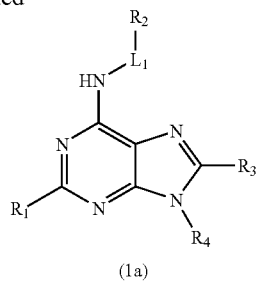

(Ia)

in which R$_1$, R$_2$, R$_3$ and R$_4$ are as defined for Formula I in the Summary of the Invention and L of Formula I is defined in the reaction scheme as —NH-L$_1$- which is equivalent to, for example, —NR$_{5a}$(CH$_2$)$_{0-3}$— where R$_{5a}$ is hydrogen and —(CH$_2$)$_{0-3}$— is L$_1$.

Compounds of Formula I can be prepared by reacting a compound of Formula 8 with an amine compound of Formula 5 in an appropriate solvent (e.g. isopropanol) at a temperature of about room temperature to about 100° C. Compounds of Formula 8 can in turn be prepared by reacting a compound of Formula 9 with a compound of Formula 3 in the presence of a suitable catalyst (e.g., Pd(Ph$_3$P)$_4$, Pd$_2$(dba)$_3$, or the like), optionally in the presence of an appropriate ligand (e.g., 1,3-bis(2,4,6-trimethylphenyl) imidazolium chloride), a suitable base (e.g., Cs$_2$CO$_3$, or the like) and an appropriate solvent (e.g., 1,4-dioxane) at a temperature of about 80 to 100° C. for 2 to about 48 hours. Compounds of Formula 9 in turn can be prepared by reacting a compound of Formula 10 with a mixture of di-iodomethane, copper(I) iodide, and an alkyl nitrite (e.g. isoamylnitrile), optionally in the presence of an inert solvent, at a temperature of about 50 to 100° C. Compounds of Formula 10 can be prepared by alkylation of a compound of Formula 11 with a suitable alkylating agent 7, in which X$_1$ is chlorine, bromine, iodine, or a sulfonate ester, in the presence of a suitable base (e.g. sodium hydride or potassium carbonate), in a suitable solvent (e.g. DMF), at a temperature of about 0° C. to about 80° C. Alternatively, the reaction can be performed under Mitsunobu conditions using a suitable alcohol R$_4$—OH in the presence of a suitable phosphine (e.g. triphenylphosphine) and azodicarboxylate (e.g. diethylazodicarboxylate), in an inert solvent such as THF or toluene, at a temperature from about 0° C. to about room temperature.

Compounds of Formula II, which are a subset of compounds of Formula I in which R$_1$ is N-linked heterocyclyl or N-linked heteroaryl, can be prepared as detailed in the following Reaction Scheme 3:

Reaction Scheme 3

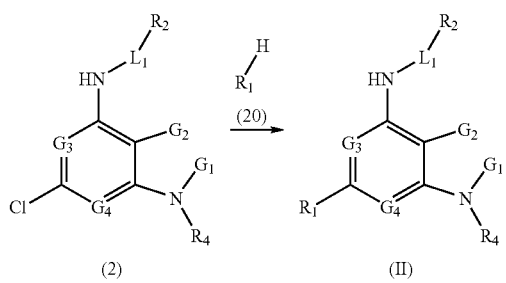

G$_1$, G$_2$, G$_3$, G$_4$, R$_1$, R$_2$ and R$_4$ are as defined for Formula I in the Summary of the Invention and L of Formula I is defined in the reaction scheme as —NH-L$_1$- which is equivalent to, for example, —NR$_{5a}$(CH$_2$)$_{0-3}$— where R$_{5a}$ is hydrogen and —(CH$_2$)$_{0-3}$— is L$_1$. Compounds of Formula II can be prepared by reacting a compound of Formula 2 with a compound of Formula 20 in the presence of an excess of cyclic amine or NH-bearing heterocycle (for example, substituted pyrazole, substituted imidazole, and the like), at a temperature of about 50° C. to about 250° C., for about 1 to about 24 hours, optionally in the presence of a base such as sodium hydride or DBU.

Compounds of Formula 10 in which G$_1$ is CR$_3$, and in which all other G groups are N, can also be prepared by proceeding as in the following Reaction Scheme 4:

Reaction Scheme 4

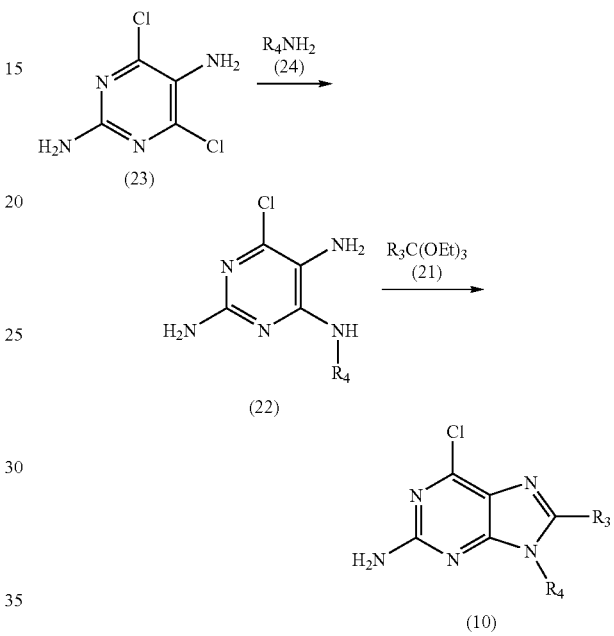

in which R$_3$ and R$_4$ are as defined for Formula I in the Summary of the Invention. Compounds of Formula 10 can be prepared according to procedures described in J. Med. Chem., 1972, 456, and J. Med. Chem., 1992, 4180. An orthoester compound of Formula 21 is reacted with a compound of Formula 22, optionally in the presence of an acid such as acetic acid, at a temperature of about room temperature to about 150° C., for about 1 to about 24 hr. A compound of Formula 22 can in turn be prepared by reacting a compound of Formula 23 with a primary amine compound of Formula 24, optionally in the presence of an acid such as pTSA, or a base such as triethylamine or DBU, at a temperature of about 50 to about 200° C.

Compounds of Formula IV can be prepared as detailed in the following Reaction Scheme 5:

Reaction Scheme 5

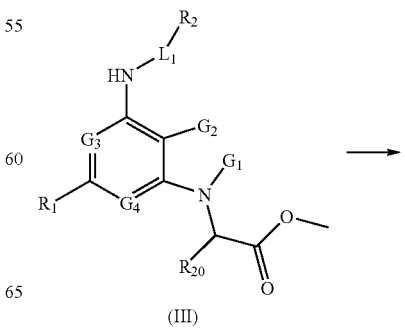

(III)

-continued

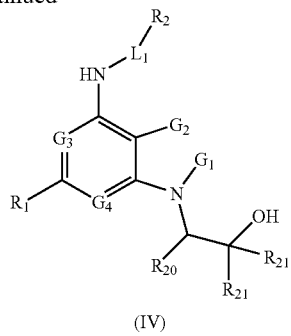

(IV)

in which $G_1$, $G_2$, $G_3$, $G_4$, $R_1$ and $R_2$ are as defined for Formula I in the Summary of the Invention and L of Formula I is defined in the reaction scheme as —NH-$L_1$- which is equivalent to, for example, —$NR_{5a}(CH_2)_{0-3}$— where $R_{5a}$ is hydrogen and —$(CH_2)_{0-3}$— is $L_1$. $R_{20}$ and $R_{21}$ are independently selected from hydrogen and $C_{1-4}$alkyl. A compound of Formula IV, in which $R_{21}$ is hydrogen, can be prepared from a compound of Formula III by treatment with a suitable reducing agent such as lithium aluminum hydride or di-isobutyl aluminum hydride, in a suitable solvent such as THF or toluene, at a temperature of about −78° C. to about 50° C. The reaction takes about 0.5 to about 16 hr to complete. A compound of Formula IV, in which $R_{21}$ is lower alkyl, can be prepared by treatment of a compound of Formula III with an alkyl lithium or Grignard reagent, in a suitable solvent such as ether or tetrahydrofuran, at a temperature of about −78° C. to about 50° C. The reaction takes about 0.5 to about 16 hr to complete.

Detailed examples of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

For example, salt forms of 4-(2-(2-(benzo[b]thiophen-3-yl)-9-isopropyl-9H-purin-6-ylamino)ethyl)phenol (Example 1, infra) were synthesized as follows:

Mesylate salt: 4-(2-(2-(benzo[b]thiophen-3-yl)-9-isopropyl-9H-purin-6-ylamino)ethyl)phenol free base (0.60 g; 1.40 mmoles) are dissolved in 12 ml acetone at 50° C. Methanesulfonic acid (0.137 g; 1.40 mmoles) is added drop wise. The crystallization takes place rapidly. The white suspension is allowed to cool over about 30 minutes with cooling to room temperature. The slurry is stirred for 18 hours at room temperature and filtered. The solid is washed with acetone (6 ml) in three portions and dried first for about 3 hours at 50° C./ca. 10 mbar and then for about 16 hours at 80° C./ca. 10 mbar. The material has a melting point at about 233° C. with a melting enthalpy of 98 g/J. The material produced exhibited a loss on drying of 0.2%. The water uptake was estimated by thermogravimetry after exposure to relative humidity (80% rh) during 24 hours. A water uptake of 0.4% was observed.

In another embodiment, the invention provides a mesylate salt of the compound of Example 1. In a further embodiment, the invention provides the mesylate salt of the compound of Example 1 comprising the following powder X-ray diffraction peaks (Angle 2-Theta °): 6.4, 6.7, 18.3, 18.6, 26.9; and which in an additional embodiment comprises the following powder X-ray diffraction peaks (Angle 2-Theta °): 6.4, 6.7, 10.3, 12.9, 16.4, 18.3, 25.8, 26.5, 26.9.

In a yet further embodiment, the invention provides the mesylate salt of the compound of Example 1 having the powder X-ray diffraction pattern shown in FIG. 3 herein.

Tosylate salt: 4-(2-(2-(benzo[b]thiophen-3-yl)-9-isopropyl-9H-purin-6-ylamino)ethyl)phenol free base (0.60 g; 1.40 mmoles) are dissolved in 12 ml at 50° C. A solution of para-toluenesulfonic acid mono-hydrate (0.271 g; 1.40 mmoles) in acetone (1.2 ml) is added drop wise. The solution is seeded at 50° C. and crystallization takes place quickly. The suspension is allowed to cool over about 30 minutes to room temperature and stirred for about 18 hours. After filtration the solid is washed with acetone (6 ml) in three portions and dried first for about 3 hours at 50° C./ca. 10 mbar and then for about 16 hours at 80° C./ca. 10 mbar. The material has a melting point at about 233° C. with a melting enthalpy of 88 g/J. The material produced exhibited a loss on drying of 0.2%. The water uptake was estimated by Thermogravimetry after exposure to relative humidity (80% rh) during 24 hours. A water uptake of 0.4% was observed.

In another embodiment, the invention provides a tosylate salt of the compound of Example 1. In a further embodiment, the invention provides the tosylate salt of the compound of Example 1 comprising the following powder X-ray diffraction peaks (Angle 2-Theta °): 6.2, 13.3, 16.7, 19.5, 25.4; and which in an additional embodiment comprises the following powder X-ray diffraction peaks: 6.2, 7.6, 12.4, 13.3, 15.1, 16.7, 17.7, 19.5, 20.2, 24.6, 24.9, 25.4, 25.6.

In a yet further embodiment, the invention provides the tosylate salt of the compound of Example 1 having the powder X-ray diffraction pattern shown in FIG. 4 herein.

Sulfate salt: 4-(2-(2-(benzo[b]thiophen-3-yl)-9-isopropyl-9H-purin-6-ylamino)ethyl)phenol free base (0.60 g; 1.40 mmoles) are dissolved in 10 ml acetone and 1 ml water at about 55° C. A solution of sulfuric acid (0.280 g; 2.79 mmoles) in 1 ml water is added drop wise. The crystallization takes place rapidly. The suspension is allowed to cool over about 30 minutes with cooling to room temperature, stirred for about 18 hours and filtered. The filter cake is washed with 6 ml acetone in three portions and dried first for about 3 hours at 50° C./ca. 10 mbar and then for about 16 hours at 80° C./ca. 10 mbar. The material has a melting point at about 224° C. with a melting enthalpy of 91 g/J. The material produced exhibited a loss on drying below 0.05%. The water uptake was estimated by Thermogravimetry after exposure to relative humidity (80% rh) during 24 hours. A water uptake of 0.2% was observed.

In another embodiment, the invention provides a sulfate salt of the compound of Example 1. In a further embodiment, the invention provides the sulfate salt of the compound of Example 1 comprising the following powder X-ray diffraction peaks (Angle 2-Theta °): 6.5, 6.8, 10.7, 13.5, 26.4, 27.6; and which in an additional embodiment comprises the following powder X-ray diffraction peaks (Angle 2-Theta °): 6.5, 6.8, 10.7, 13.1, 13.5, 18.6, 18.8, 20.8, 26.4, 27.1, 27.6.

In a yet further embodiment, the invention provides the sulfate salt of the compound of Example 1 having the powder X-ray diffraction pattern shown in FIG. 6 herein.

Esylate salt: 4-(2-(2-(benzo[b]thiophen-3-yl)-9-isopropyl-9H-purin-6-ylamino)ethyl)phenol free base (0.60 g; 1.40 mmoles) are dissolved in 12 ml acetone at 50° C. Ethanesulfonic acid (0.155 g; 1.40 mmoles) is added drop wise. The crystallization takes place quickly. The resulting white suspension is allowed to cool over about 30 minutes to room temperature. The suspension is stirred for about 18 hours at room temperature and filtered. The solid is washed with 6 ml acetone in three portions and dried first for about 3 hours at 50° C./ca. 10 mbar and then for about 16 hours at 80° C./ca. 10 mbar. The material has a melting point at about 231° C. with a melting enthalpy of 76 g/J. The material produced exhibited a loss on drying of 0.6%. The water uptake was estimated by Thermogravimetry after exposure to relative humidity (80% rh) during 24 hours. A water uptake of 0.05% was observed.

In another embodiment, the invention provides a esylate salt of the compound of Example 1. In a further embodiment, the invention provides the esylate salt of the compound of Example 1 comprising the following powder X-ray diffraction peaks (Angle 2-Theta °): 6.3, 9.9, 18.4, 25.3, 26.1; and which in an additional embodiment comprises the following powder X-ray diffraction peaks (Angle 2-Theta °): 6.3, 9.9, 17.1, 17.9, 18.4, 19.0, 22.0, 25.3, 26.1, 27.1.

In a yet further embodiment, the invention provides the esylate salt of the compound of Example 1 having the powder X-ray diffraction pattern shown in FIG. 8 herein.

Hydrobromide salt: 4-(2-(2-(benzo[b]thiophen-3-yl)-9-isopropyl-9H-purin-6-ylamino)ethyl)phenol free base (0.60 g; 1.40 mmoles) are dissolved in 6 ml DMF at 65° C. Hydrobromic acid 48% (0.235 g; 1.40 mmoles) is added drop wise. The solution is allowed to cool over about 30 minutes to room temperature. Seeds are added at 55° C. and crystallization takes place slowly. The suspension is stirred for about 18 hours at room temperature and filtered. The solid is washed with 4 ml DMF/water 1:1 and 6 ml water. The salt is dried first for about 3 hours at 50° C./ca. 10 mbar and then for about 16 hours at 80° C./ca. 10 mbar. The material has a melting point at about 285° C. with a melting enthalpy of 119 g/J. The material produced exhibited a loss on drying of 1.0%. The water uptake was estimated by Thermogravimetry after exposure to relative humidity (80% rh) during 24 hours. No water uptake was observed.

In another embodiment, the invention provides a hydrobromide salt of the compound of Example 1. In a further embodiment, the invention provides the hydrobromide salt of the compound of Example 1 comprising the following powder X-ray diffraction peaks (Angle 2-Theta °): 7.0, 25.9, 26.8, 27.9; and which in an additional embodiment comprises the following powder X-ray diffraction peaks (Angle 2-Theta °): 7.0, 11.4, 13.3, 21.4, 23.4, 25.9, 26.4, 26.8, 27.9.

In a yet further embodiment, the invention provides the hydrobromide salt of the compound of Example 1 having the powder X-ray diffraction pattern shown in FIG. 9 herein.

Orotate salt: 4-(2-(2-(benzo[b]thiophen-3-yl)-9-isopropyl-9H-purin-6-ylamino)ethyl)phenol free base (0.60 g; 1.40 mmoles) and orotic acid (0.222 g; 1.40 mmoles) are dissolved in 7.8 ml NMP (1-Methyl-2-pyrrolidone) at 85° C. The solution is cooled to 60° C. and 6 ml water is added drop wise over about 5 minutes. The resulting white suspension is allowed to cool over about 30 minutes to room temperature and stirred for 18 hours. After filtration the filter cake is washed with 4 ml NMP/water 1:1 in two portions and 6 ml water in three portions. The solid is dried first for about 3 hours at 50° C./ca. 10 mbar and then for about 16 hours at 80° C./ca. 10 mbar. The material has a melting point at about 240° C. with a melting enthalpy of 130 g/J. The material produced exhibited a loss on drying below 0.05%. The water uptake was estimated by Thermogravimetry after exposure to relative humidity (80% rh) during 24 hours. A water uptake of 1.7% was observed.

In another embodiment, the invention provides an orotate salt of the compound of Example 1. In a further embodiment, the invention provides the orotate salt of the compound of Example 1 comprising the following powder X-ray diffraction peaks (Angle 2-Theta °): 7.1, 16.3, 19.2, 23.5, 25.6, 26.9; and which in an additional embodiment comprises the following powder X-ray diffraction peaks (Angle 2-Theta °): 7.1, 14.4, 16.3, 18.6, 19.2, 21.7, 23.0, 23.5, 25.6, 26.9, 28.7.

In a yet further embodiment, the invention provides the orotate salt of the compound of Example 1 having the powder X-ray diffraction pattern shown in FIG. 10 herein.

Hemi-fumarate salt: 4-(2-(2-(benzo[b]thiophen-3-yl)-9-isopropyl-9H-purin-6-ylamino)ethyl)phenol free base (0.60 g; 1.40 mmoles) are dissolved in 18 ml methanol at 65° C. Fumaric acid (0.164 g; 1.40 mmoles) and 6 ml methanol are added. The solution is allowed to cool over about 30 minutes to room temperature. Some seed crystals are added at 60° C. and crystallization takes place slowly. The suspension is stirred for 18 hours at room temperature and filtered. The solid is washed with 6 ml methanol in three portions and dried first for about 3 hours at 50° C./ca. 10 mbar and then for about 16 hours at 80° C./ca. 10 mbar. The material has a melting point at about 232° C. with a melting enthalpy of 83 g/J. The material produced exhibited a loss on drying below 0.05%. The water uptake was estimated by Thermogravimetry after exposure to relative humidity (80% rh) during 24 hours. A water uptake of 0.3% was observed.

In another embodiment, the invention provides a hemi-fumarate salt of the compound of Example 1. In a further embodiment, the invention provides the hemi-fumarate salt of the compound of Example 1 comprising the following powder X-ray diffraction peaks (Angle 2-Theta °): 7.2, 8.7, 14.4, 15.8, 17.4, 19.0, 23.7; and which in an additional embodiment comprises the following powder X-ray diffraction peaks (Angle 2-Theta °): 7.2, 8.7, 10.8, 14.4, 15.8, 17.4, 17.8, 19.0, 20.1, 23.7, 27.5.

In a yet further embodiment, the invention provides the hemi-fumarate salt of the compound of Example 1 having the powder X-ray diffraction pattern shown in FIG. 11 herein.

Besylate salt: 4-(2-(2-(benzo[b]thiophen-3-yl)-9-isopropyl-9H-purin-6-ylamino)ethyl)phenol free base (0.60 g; 1.40 mmoles) are dissolved in 12 ml acetone at 50° C. A solution of benzenesulfonic acid (0.225 g; 2.79 mmoles) in 1.2 ml acetone is added drop wise. Seed crystals are added at 48° C. and the crystallization takes place slowly. The suspension is allowed to cool over about 30 minutes to room temperature. The slurry is stirred for about 18 hours at room temperature and filtered. The salt is washed with 6 ml acetone in three portions and dried first for about 3 hours at 50° C./ca. 10 mbar and then for about 16 hours at 80° C./ca. 10 mbar. The material has a melting point at about 219° C. with a melting enthalpy of 92 g/J. The material produced exhibited a loss on drying of 0.3%. The water uptake was estimated by Thermogravimetry after exposure to relative humidity (80% rh) during 24 hours. A water uptake of about 0.05% was observed.

In another embodiment, the invention provides a besylate salt of the compound of Example 1. In a further embodiment, the invention provides the besylate salt of the compound of Example 1 comprising the following powder X-ray diffraction peaks (Angle 2-Theta °): 6.2, 7.7, 17.7, 25.5; and which in an additional embodiment comprises the following powder X-ray diffraction peaks (Angle 2-Theta °): 6.2, 7.7, 15.2, 16.7, 17.1, 17.7, 19.8, 20.2, 24.9, 25.2, 25.5.

In a yet further embodiment, the invention provides the besylate salt of the compound of Example 1 having the powder X-ray diffraction pattern shown in FIG. 7 herein.

Napadisylate salt: 4-(2-(2-(benzo[b]thiophen-3-yl)-9-isopropyl-9H-purin-6-ylamino)ethyl)phenol free base (0.60 g; 1.40 mmoles) and 0.259 g 1,5-naphthalenedisulfonic acid (0.70 mmoles) are dissolved in 9 ml DMF at 87° C. The clear solution is allowed to cool over about 30 minutes to room temperature. Seeds are added at 65° C. and crystallization takes place slowly. The suspension is stirred for about 18 hours at room temperature and filtered. The solid is washed with 4 ml DMF/water 1:1 in two portions and 6 ml water in three portions. The salt is dried first for about 3 hours at 50° C./ca. 10 mbar and then for about 16 hours at 80° C./ca. 10 mbar. The material has a melting point at about 304° C. with a melting enthalpy of 83 g/J. A broad endothermic phenomenon is observed at 107° C. that might be attributed to the loss of water. The material produced exhibited a loss on drying of 6.1%. The water uptake was estimated by Thermogravimetry after exposure to relative humidity (80% rh) during 24 hours. A water uptake less than 0.05% was observed.

In another embodiment, the invention provides a napadysilate salt of the compound of Example 1. In a further embodiment, the invention provides the napadysilate salt of the compound of Example 1 comprising the following powder X-ray diffraction peaks (Angle 2-Theta °): 6.4, 9.6, 13.1, 15.7, 16.1, 26.0; and which in an additional embodiment comprises the following powder X-ray diffraction peaks (Angle 2-Theta °): 9.6, 13.1, 15.7, 16.1, 16.4, 20.4, 20.9, 23.7, 26.0, 26.9.

In a yet further embodiment, the invention provides the napadysilate salt of the compound of Example 1 having the powder X-ray diffraction pattern shown in FIG. 12 herein.

Hydrochloride salt: 4-(2-(2-(benzo[b]thiophen-3-yl)-9-isopropyl-9H-purin-6-ylamino)ethyl)phenol free base (0.60 g; 1.40 mmoles) are dissolved in 12 ml acetone at 55° C. Hydrochloric acid 37% (0.138 g; 1.40 mmoles) is added drop wise. The crystallization takes place quickly. The white suspension is allowed to cool over about 30 minutes to room temperature and stirred for 18 hours. After filtration the solid is washed with 6 ml acetone in three portions and dried first for about 3 hours at 50° C./ca. 10 mbar and then for about 16 hours at 80° C./ca. 10 mbar. The material is exhibiting an exothermic event at about 162° C. with an enthalpy of −13.8 J/g. This phenomenon might be attributed to a solid transformation into a more stable modification. An endothermic event is then seen at about 259° C. with an enthalpy of 99.7 J/g. The material produced exhibited a loss on drying of 0.6%. The water uptake was estimated by Thermogravimetry after exposure to relative humidity (80% rh) during 24 hours. A water uptake of 0.3% was observed.

In another embodiment, the invention provides a hydrochloride salt of the compound of Example 1. In a further embodiment, the invention provides the hydrochloride salt of the compound of Example 1 comprising the following powder X-ray diffraction peaks (Angle 2-Theta °): 6.1, 7.0, 19.8, 26.1; and which in an additional embodiment comprises the following powder X-ray diffraction peaks (Angle 2-Theta °): 6.1, 7.0, 18.1, 19.8, 24.7, 26.1, 27.0, 27.7.

In a yet further embodiment, the invention provides the hydrochloride salt of the compound of Example 1 having the powder X-ray diffraction pattern shown in FIG. 5 herein.

The free acid or free base forms of the compounds of the invention can be prepared from the corresponding base addition salt or acid addition salt form, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.). The nitrate salt of the compound of example 1 can be made using methods known to the skilled person. The powder X-ray diffraction pattern is disclosed in FIG. 2 herein.

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981. Compounds of the invention can also be prepared as their individual stereoisomers by using chiral chromatography techniques, in particular, by use of HPLC or SFC chromatography using a chiral stationary phase.

Powder X-ray diffraction spectra as enclosed herein were obtained using the instrument Bruker D8 Vario in transmission geometry, irradiation CuKα (30 kV, 40 mA), scan range 2°-40° (2 theta value), step time 90.3 s. Differential scanning calorimetry (DSC) of Example 1 amorphous material was carried out using the instrument Perkin Elmer DSC7 at a heating rate of 40° C./min.

In summary, the compounds of Formula I can be made by a process, which involves:
 (a) those of reaction schemes 1-5; and
 (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I (Examples) according to the invention.

Example 1

4-(2-(2-(benzo[b]thiophen-3-yl)-9-isopropyl-9H-purin-6-ylamino)ethyl)phenol

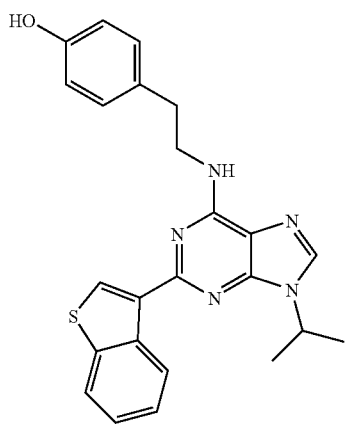 [SMILES: CC(C)n1cnc2c(NCCc3ccc(O)cc3)nc(-c3csc4ccccc34)nc21]

Synthesis of 2,6-dichloro-9-isopropyl-9H-purine (b)

To 2,6-dichloro-9H-purine (a) (6.0 mmol) dissolved in anhydrous DMF (5.0 mL) was slowly added sodium hydride (7.8 mmol) with stirring at rt over 2 hr. 2-iodopropane was added and the mixture was stirred for 16 hr. The mixture was concentrated. The residue was purified by column chromatography on silica gel, eluting with hexane/EtOAc (20:1 to 3:1) to afford the title compound as a white solid. $^1$H NMR (500 MHz, CDCl$_3$): δ 8.15 (s, 1H), 4.91 (m, 1H), 1.63 (d, 6H).

Synthesis of 4-(2-(2-chloro-9-isopropyl-9H-purin-6-ylamino)ethyl)phenol (c)

2,6-dichloro-9-isopropyl-9H-purine (1.1 mmol) was mixed with tyramine (1.16 mmol) dissolved in i-PrOH (6 ml) and the mixture was stirred overnight. The reaction mixture was concentrated, and the residue purified by column chromatography on silica gel, eluting with hexane/EtOAc (5:1 to 1:2) to afford the title compound as a white solid. $^1$H NMR (500 MHz, CDCl$_3$): δ 9.21 (br, 1H), 8.49 (s, 1H), 7.80 (s, 1H), 7.10 (d, 2H), 6.73 (d, 2H), 4.87 (m, 1H), 4.03 (t, 2H), 3.01 (t, 2H), 1.68 (d, 6H); HRMS (EI) calcd for C$_{16}$H$_{18}$ClN$_5$O (M+H$^+$) 332.1273, found 332.1278.

Synthesis of 4-(2-(2-(benzo[b]thiophen-3-yl)-9-isopropyl-9H-purin-6-ylamino)ethyl)phenol (d)

A flame-dried schlenk flask was charged with 4-(2-(2-chloro-9-isopropyl-9H-purin-6-ylamino)ethyl)phenol (0.62 mmol), thianaphthene-3-boronic acid (0.94 mmol), pd$_2$(dba)$_3$ (0.062 mmol), Cs$_2$CO$_3$ (1.25 mmol) and 1,3-bis(2,4,6-trimethylphenyl) imidazolium chloride (0.125 mmol). The flask was evacuated and backfilled with N$_2$ and anhydrous 1,4-dioxane (2 mL) was added. The flask was sealed and the reaction mixture was stirred at 80° C. for 24 hours. The reaction mixture was concentrated and purified directly by column chromatography on silica gel, eluting with hexane/EtOAc (20:1 to 1:4) to afford the title compound as a yellowish solid.

Alternatively, the synthesis of Example 1 can be carried out as follows:

Synthesis of 2-(benzo[b]thiophen-3-yl)-6-chloro-9-isopropyl-9H-purine (b)

A round-bottom flask was charged with 6-chloro-2-iodo-9-isopropyl-9H-purine (prepared in Example 15c, 3.31 g, 0.0103 mol), benzo[b]thiophen-3-ylboronic acid (2.74 g, 0.0154 mol), and tetrakis(triphenylphosphine)palladium(0) (1.19 g, 0.0103 mol). To this mixture was added toluene (80 ml), ethanol (25 ml) and aqueous sodium carbonate solution (2M, 21 ml). The flask was sealed and the reaction mixture was stirred at 90° C. for 1 h. Water was added to the cooled mixture, which was extracted with ethyl acetate. The organic fractions were combined, dried over sodium sulfate, and concentrated. The residue was purified by column chromatography on silica gel, eluting with 20 to 50% EtOAc in hexane to afford the title compound as a solid, which was recrystallized from 1:1 methanol/water. $^1$H NMR (400 MHz, DMSO-d$_6$): δ=9.15 (d, 1H), 8.85 (s, 2H), 8.17 (d, 1H), 7.62 (t, 1H), 7.53 (t, 1H), 5.06 (m, 1H), 1.71 (d, 6H); MS m/z 329.0 (M+1).

Synthesis of 4-(2-(2-(benzo[b]thiophen-3-yl)-9-isopropyl-9H-purin-6-ylamino)ethyl)phenol (c)

2-(benzo[b]thiophen-3-yl)-6-chloro-9-isopropyl-9H-purine (2.2 g, 0.0067 mol) was suspended in anhydrous 2-propanol (70 mL) in a pressure tube. Tyramine (1.01 g, 0.0074 mol) was added. The tube was sealed and heated at 85° C. for 16 hr. Additional tyramine (0.50 g, 0.0037 mol) was added and the mixture was heated at 85° C. for 48 hr. The reaction was concentrated. Aqueous sodium bicarbonate solution was added to the residue, which was extracted with EtOAc. The combined organic extracts were dried over sodium sulfate, filtered, and concentrated. The residue was purified by column chromatography on silica gel, eluting with 50 to 85% EtOAc in hexane to afford a solid. The solid was triturated with methanol to provide the title compound as an off-white solid.

Alternatively, the synthesis of Example 1 can be carried out as follows:

Synthesis of 2,6-dichloro-9-isopropyl-9H-purine (b)

To 2,6-dichloro-9H-purine (a) (998 g, 5.28 mol) dissolved in anhydrous DMF (5.0 L) was added sodium hydride (60% dispersion, 254 g, 6.35 mol) with stirring at 10° C. over 1 hr. 2-iodopropane (1595 g) was added and the mixture was stirred at rt for 24 hr. Water (5.0 L) was added, and the resulting solid precipitate was collected and washed with water (500 ml) and heptane (2×2.5 L). The crude solid was crystallized from isopropyl acetate (2.1 L) to provide the title compound as a solid.

Synthesis of 4-(2-(2-chloro-9-isopropyl-9H-purin-6-ylamino)ethyl)phenol (c)

2,6-dichloro-9-isopropyl-9H-purine (500 g) was added in portions to a stirred mixture of tyramine (593 g), triethylamine (262 g), and i-PrOH (5.0 L) at 50° C. The mixture was stirred at that temperature for 4 hr, then the reaction mixture was concentrated. The residue was taken up in isopropyl acetate (6.0 L) and was washed with 20% citric acid solution (2.0 L) and water (2.0 L). The organic layer was concentrated to dryness, then was taken up in ethanol (2.0 L) and again concentrated to dryness. The crude solid was crystallized from ethanol (3.2 L) to provide the title compound as a solid.

Synthesis of 4-(2-(2-(benzo[b]thiophen-3-yl)-9-isopropyl-9H-purin-6-ylamino)ethyl)phenol (d): A mixture of 4-(2-(2-chloro-9-isopropyl-9H-purin-6-ylamino)ethyl)phenol (950 g), thianaphthene-3-boronic acid (561 g), dichlorobis(triphenylphosphine)palladium(II) (10.1 g), potassium carbonate (791 g), water (3.25 L), and DMA (3.25 L) was stirred under a nitrogen atmosphere for 10 min. The stirred mixture was then heated at 70° C. for 14 h. Ethyl acetate (6.5 L) and water (3.25 L) were added, and the mixture was filtered through Celite (125 g) at 50° C., rinsing with ethyl acetate (1.0 L). The layers were separated, and the aqueous layer was extracted at 50° C. with additional ethyl acetate (7.5 L). The combined organic layers were washed with water (3×2.5 L), then distilled to remove about 2.5 L of solvent. Tetrahydrofuran (2.5 L) and silica bond thio silica gel (200 g) were added. The mixture was stirred at 70° C. for 16 hr, then was filtered, washing the pad with ethyl acetate (1.0 L). The combined filtrates were concentrated at atmospheric pressure to a volume of about 5 L, then the mixture was allowed to cool. The resulting solid was collected and washed with ethyl acetate (2×1.0 L) to provide the title compound.

The compound of Example 1 can be recrystallised using a toluene/ethanol mixture and washed at room temperature with NaHCO$_3$ aqueous solution.

In another embodiment, the invention provides a compound of Example 1 in crystal form modification A, wherein modification A comprises the following powder X-ray diffraction peaks (angle 2-Theta °): 12.1, 16.9, 18.9, 21.3; and which in an additional embodiment comprises the following powder X-ray diffraction peaks (angle 2-Theta °): 12.1, 15.9, 16.9, 17.3, 18.9, 21.3, 22.1, 23.6, 24.4, 27.3.

In a yet further embodiment, the invention provides the compound of Example 1 as solid form modification A comprising the following powder X-ray diffraction peaks (angle 2-Theta °): 9.0, 12.1, 13.0, 13.1, 13.6, 14.4, 14.7, 15.1, 15.9, 16.9, 17.3, 17.7, 18.0, 18.9, 19.0, 20.1, 21.3, 22.1, 22.3, 22.6, 22.8, 23.4, 23.6, 24.4, 25.3, 26.3, 26.5, 27.3, 27.8, 28.2, 29.5, 29.7, 30.4, 30.7, 31.0, 31.4, 32.2, 32.8, 33.3, 34.3, 35.5, 36.4, 37.5, 38.4, 39.0, 39.4.

The powder X-ray diffraction pattern of the compound of Example 1, modification A, is shown in FIG. 1 herein. Amorphous material of the compound of Example 1 was produced in situ in a DSC (differential scanning calorimetry) crucible by heating the compound until melting and annealing/cooling. Upon the cooling cycle the glass transition could be observed but upon the reheating cycle is much more characterized at about 70-75° C. The DSC pattern is shown in FIG. 13 herein.

Example 15

4-(2-(Pyridin-3-yl)-9-isopropyl-9H-purin-6-ylamino)ethyl)phenol

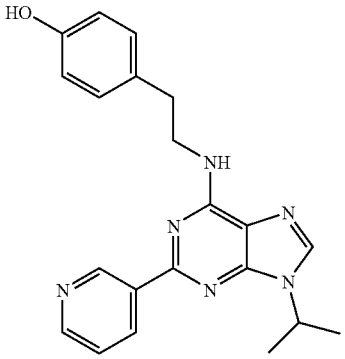 [SMILES: CC(C)n1cnc2c(NCCc3ccc(O)cc3)nc(-c3cccnc3)nc21]

Synthesis of 2-Amino-6-chloro-9-isopropyl-9H-purine (b)

Sodium hydride (1.5 g of 60% dispersion in mineral oil, 38 mmol) was added in portions over 10 min to a stirred suspension of 2-amino-6-chloro-9H-purine (5.34 g, 31.5 mmol) in anhydrous DMF (50 mL) at rt. After 45 min, the mixture was cooled in an ice bath, then 2-iodopropane was added. The cooling bath was removed and the stirred mixture was allowed to warm to rt over 16 h. The mixture was cooled in ice, then water was added. The mixture was concentrated, and the residue was treated with hot ethyl acetate. The cooled mixture was filtered, and the filtrate was concentrated. The residue was purified by column chromatography on silica gel, eluting with 0 to 50% EtOAc in hexane to afford the title compound as a solid. $^1$H NMR (400 MHz, CDCl$_3$) δ 7.83 (s, 1H), 5.17 (s, 2H), 4.71-4.66 (m, 1H), 1.57 (d, 6H). MS m/z 212.1 (M+1).

Synthesis of 6-Chloro-2-iodo-9-isopropyl-9H-purine (c)

6-chloro-9-isopropyl-9H-purin-2-amine (2.68 g, 12.7 mmol) was dissolved in THF (64 mL) at rt. Iodine (1.61 g, 6.25 mmol), CH$_2$I$_2$ (10.6 mL) and CuI (1.27 g, 6.66 mmol) were added. The mixture was stirred for 5 min at room temperature. Isopentyl nitrite (5.33 mL) was added. The reaction mixture was refluxed for 45 min, and was then cooled to room temperature. Saturated aqueous sodium bicarbonate solution was added, and the mixture was extracted with EtOAc three times. The combined organic phase was washed with brine, dried with MgSO₄ and concentrated. The residue was purified by column chromatography on silica gel, eluting with 0 to 30% ethyl acetate in hexane to afford the title compound as a solid. $^1$H NMR (400 MHz, CDCl₃) δ 8.09 (s, 1H), 4.95-4.88 (m, 1H), 1.65 (d, 6H). MS m/z 323.0 (M+1).

Synthesis of 6-Chloro-2-(pyridin-3-yl)-9-isopropyl-9H-purine (d)

A round-bottom flask was charged with 6-chloro-2-iodo-9-isopropyl-9H-purine (1.2 g, 3.7 mmol), pyridine-3-boronic acid 1,3-propanediol cyclic ester (0.91 g, 5.6 mmol), and tetrakis(triphenylphosphine)palladium(0) (430 mg, 0.37 mmol). To this mixture was added toluene (60 ml), ethanol (6 ml) and aqueous sodium carbonate solution (2M, 15 ml). The flask was sealed and the reaction mixture was stirred at 80° C. for 4 h. Water was added to the cooled mixture, which was extracted with ethyl acetate (50 ml×3). The organic fractions were combined, dried over sodium sulfate, and concentrated. The residue was purified by column chromatography on silica gel, eluting with 30 to 70% EtOAc in hexane to afford the title compound as a solid. $^1$H NMR (400 MHz, CD₃OD) δ 9.60 (d, 1H), 8.90-8.87 (m, 1H), 8.68 (s, 1H), 8.67 (d, 1H), 7.63-7.60 (m, 1H), 5.12-5.05 (m, 1H), 1.74 (d, 6H). MS m/z 274.1 (M+1).

Synthesis of 4-(2-(pyridin-3-yl)-9-isopropyl-9H-purin-6-ylamino)ethyl)phenol (e)

6-chloro-9-isopropyl-2-(pyridin-3-yl)-9H-purine (300 mg, 1.1 mmol) was suspended in anhydrous 2-propanol (40 mL) in a pressure tube. Tyramine (300 mg, 2.2 mmol) was added. The tube was sealed and heated to 85° C. for 16 hr. The reaction was concentrated and the residue was purified by column chromatography on silica gel, eluting with 0 to 70% EtOAc in hexane to afford the title compound as a solid.

Example 123

4-(2-(9-Isopropyl-2-(2-methyl-1H-imidazol-1-yl)-9H-purin-6-ylamino)ethyl)phenol

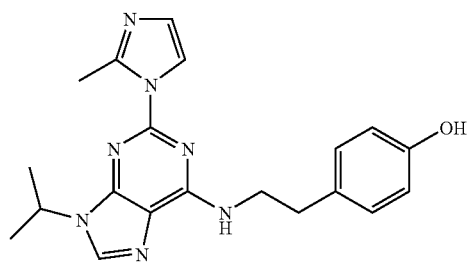 [SMILES: Cc1nccn1-c1nc(NCCc2ccc(O)cc2)c2ncn(C(C)C)c2n1]

A microwave reaction tube was charged with 4-(2-(2-chloro-9-isopropyl-9H-purin-6-ylamino)ethyl)phenol (30 mg, 0.091 mmol), 2-methyl-1H-imidazole (59 mg, 0.73 mmol) and 0.5 ml of NMP. The sealed tube was heated under microwave irradiation at 240° C. for 2 hr. The reaction mixture was purified by reverse-phase HPLC(C₁₈ column, eluting with ACN—H₂O 0.05% TFA) to afford the title compound as an off-white solid.

Example 128

4-(2-(2-(5-Chloropyridin-3-yl)-9-isopropyl-9H-purin-6-ylamino)ethyl)phenol

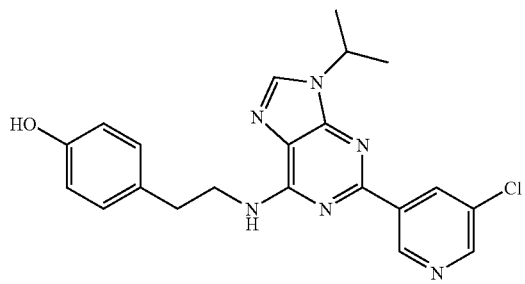 [SMILES: CC(C)n1cnc2c(NCCc3ccc(O)cc3)nc(-c3cncc(Cl)c3)nc21]

Synthesis of 4-(2-(2-iodo-9-isopropyl-9H-purin-6-ylamino)ethyl)phenol (b)

A mixture of 6-chloro-2-iodo-9-isopropyl-9H-purine (a) (1.0 g, 3.1 mmol), tyramine (0.64 g, 4.65 mmol), triethylamine (0.63 g, 6.2 mmol) and 2-propanol (30 mL) was heated at 85° C. for 2 hr. The reaction mixture was concentrated and saturated aqueous sodium bicarbonate solution was added. The mixture was extracted with ethyl acetate (50 ml×3). The combined organic layers were dried over sodium sulfate, filtered, and concentrated. The residue was purified by column chromatography on silica gel (25 to 75% ethyl acetate in hexane eluant) to afford the title compound as a solid. MS m/z 424.1 (M+1).

Synthesis of 4-(2-(2-(5-chloropyridin-3-yl)-9-isopropyl-9H-purin-6-ylamino)ethyl)phenol (c)

Following the procedure of Example 15d, 4-(2-(2-iodo-9-isopropyl-9H-purin-6-ylamino)ethyl)phenol (b) was reacted with 5-chloropyridin-3-ylboronic acid. The crude product was purified by reverse-phase HPLC(C₁₈ column, eluting with ACN—H₂O 0.05% TFA) to afford the title compound as an off-white solid.

Example 134

4-(2-(6-(5-Fluoropyridin-3-yl)-1-isopropyl-1H-pyrazolo[3,4-d]pyrimidin-4-ylamino)ethyl)phenol

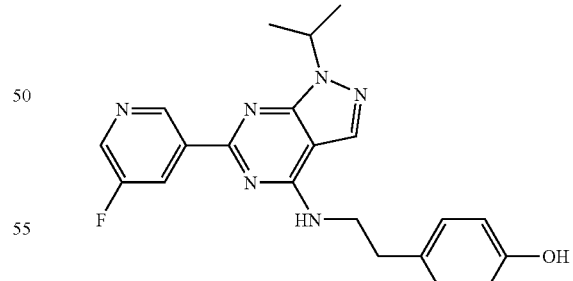

Synthesis of 4-(2-(6-chloro-1-isopropyl-1H-pyrazolo[3,4-d]pyrimidin-4-ylamino)ethyl)phenol (b)

Following the procedure of Example 128b, 4,6-dichloro-1-isopropyl-1H-pyrazolo[3,4-d]pyrimidine (U.S. Pat. No. 3,399,196) (a) (0.184 g, 0.795 mmol) was reacted with tyramine. The crude residue was purified by silica gel chromatography (25 to 75% ethyl acetate in hexane eluant) to afford the title compound as a solid. MS m/z 332.1 (M+1).

Synthesis of 4-(2-(6-(5-fluoropyridin-3-yl)-1-isopropyl-1H-pyrazolo[3,4-d]pyrimidin-4-ylamino)ethyl)phenol (c)

Following the procedure of Example 15d, 4-(2-(6-chloro-1-isopropyl-1H-pyrazolo[3,4-d]pyrimidin-4-ylamino)ethyl)phenol (b) was reacted with 5-fluoropyridin-3-ylboronic acid. The crude residue was purified by reverse-phase HPLC ($C_{18}$ column, eluting with ACN—$H_2O$ 0.05% TFA) to afford the title compound as an off-white solid.

Example 141

4-(2-(2-(5-Fluoropyridin-3-yl)-7-isopropyl-7H-pyrrolo[2,3-d]pyrimidin-4-ylamino)ethyl)phenol

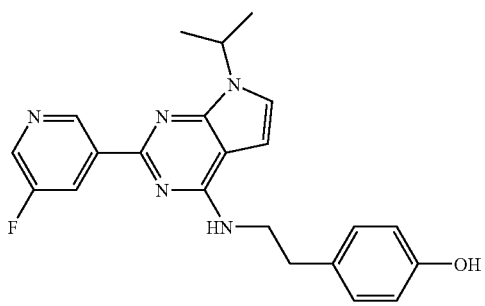 [SMILES: CC(C)n1ccc2c(NCCc3ccc(O)cc3)nc(-c3cncc(F)c3)nc21]

Synthesis of 2,4-dichloro-7-isopropyl-7H-pyrrolo[2,3-d]pyrimidine (b)

Following the procedure of Example 15b, 2,4-dichloro-7H-pyrrolo[2,3-d]pyrimidine (0.5 g, 2.67 mmol) was reacted with 2-iodopropane. The crude residue was purified by silica gel chromatography (15 to 25% ethyl acetate in hexane eluant) to afford the title compound as a solid. MS m/z 230.2 (M+1).

Synthesis of 4-(2-(2-chloro-7-isopropyl-7H-pyrrolo[2,3-d]pyrimidin-4-ylamino)ethyl)phenol (c)

Following the procedure of Example 128b, 2,4-dichloro-7-isopropyl-7H-pyrrolo[2,3-d]pyrimidine (b) (0.278 g, 1.21 mmol) was reacted with tyramine. The crude residue was purified by silica gel chromatography (25 to 75% ethyl acetate in hexane eluant) to afford the title compound as a solid. MS m/z 331.1 (M+1).

Synthesis of 4-(2-(2-(5-fluoropyridin-3-yl)-7-isopropyl-7H-pyrrolo[2,3-d]pyrimidin-4-ylamino)ethyl)phenol (d)

Following the procedure of Example 15d, 4-(2-(2-chloro-7-isopropyl-7H-pyrrolo[2,3-d]pyrimidin-4-ylamino)ethyl)phenol (20 mg, 0.06 mmol) was reacted with 5-fluoropyridin-3-ylboronic acid. The crude residue was purified by reverse-phase HPLC ($C_{18}$ column, eluting with ACN—$H_2O$ 0.05% TFA) to afford the title compound as an off-white solid.

Example 153

(R)-4-(2-(2-(benzo[b]thiophen-3-yl)-9-(tetrahydrofuran-3-yl)-9H-purin-6-ylamino)ethyl)phenol

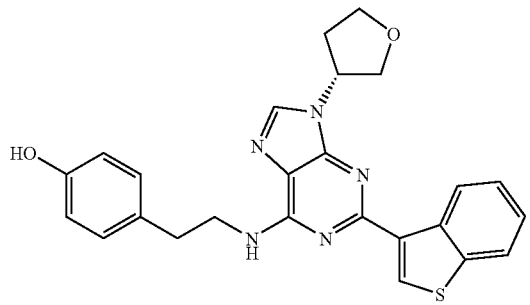 [SMILES: Oc1ccc(CCNc2nc(-c3csc4ccccc34)nc3c2ncn3[C@@H]2CCOC2)cc1]

Synthesis of (R)-2,6-dichloro-9-(tetrahydrofuran-3-yl)-9H-purine (b)

A solution of 5,7-2,6-dichloro-9H-purine (400 mg, 2.12 mmol), (S)-tetrahydrofuran-3-ol (88 mg, 2.5 mmol) and triphenylphosphine (1.0 g, 3.8 mmol) in anhydrous THF (30 mL) was treated at −78° C. with diisopropyl azodicarboxylate (856 mg, 4.23 mmol). The reaction was allowed to warmed to rt and was stirred for 16 hr. Saturated aqueous sodium bicarbonate solution was added and the mixture was extracted with ethyl acetate. The organic layers were combined, dried over sodium sulfate, and concentrated. The residue was purified by silica gel chromatography (10 to 80% ethyl acetate in hexane eluant) to afford a white solid which consisted of the title compound contaminated with triphenylphosphoxide. MS m/z 258.0 (M+1).

Synthesis of (R)-4-(2-(2-chloro-9-(tetrahydrofuran-3-yl)-9H-purin-6-ylamino)ethyl)phenol (c)

Following the procedure of Example 128b, (R)-2,6-dichloro-9-(tetrahydrofuran-3-yl)-9H-purine (b) was reacted with tyramine. The crude reaction mixture was purified by reverse-phase preparative HPLC. MS m/z 360.1 (M+1).

Synthesis of (R)-4-(2-(2-(benzo[b]thiophen-3-yl)-9-(tetrahydrofuran-3-yl)-9H-purin-6-ylamino)ethyl)phenol Following the procedure of Example 15d, (R)-4-(2-(2-chloro-9-(tetrahydrofuran-3-yl)-9H-purin-6-ylamino)ethyl)phenol (c) was reacted with benzo[b]thiophen-3-ylboronic acid (22.3 mg, 0.125 mmol). The crude residue was purified by reverse-phase preparative HPLC to afford the title compound as an off-white solid.

Example 157

2-(6-(2-(1H-indol-3-yl)ethylamino)-2-(5-fluoropyridin-3-yl)-9H-purin-9-yl)propan-1-ol

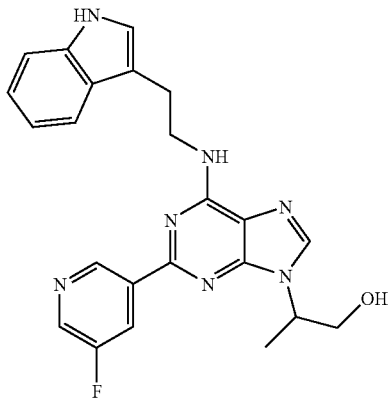 [SMILES: CC(CO)n1cnc2c(NCCc3c[nH]c4ccccc34)nc(-c3cncc(F)c3)nc21]

Synthesis of methyl 2-(2,6-dichloro-9H-purin-9-yl)propanoate (b)

A mixture of 2,6-dichloro-9H-purine (5.0 g, 26.5 mmol), methyl 2-bromopropanoate (5.3 g, 31.7 mmol) and potassium carbonate (11.0 g, 79.4 mmol) in anhydrous DMF (100 mL) was heated at 100° C. for 15 h. Sat. aqueous sodium bicarbonate solution was added and reaction was extracted with ethyl acetate (150 ml×3). The organic layers were combined, washed with brine, dried over sodium sulfate, and concentrated. The residue was purified by silica gel chromatography (10 to 80% ethyl acetate in hexane eluant) to afford the title compound as a white solid. MS m/z 275.0 (M+1).

Synthesis of methyl 2-(6-(2-(1H-indol-3-yl)ethylamino)-2-chloro-9H-purin-9-yl)propanoate (c)

A mixture of methyl 2-(2,6-dichloro-9H-purin-9-yl)propanoate (b) (600 mg, 2.2 mmol), tryptamine (420 mg, 2.6 mmol) and 2-propanol (30 mL) was heated at 85° C. in a sealed tube for 16 h. The reaction mixture was cooled to room temperature and concentrated. The residue was purified by silica gel chromatography (10 to 80% ethyl acetate in hexane eluant) to afford the title compound as a white solid. MS m/z 360.1 (M+1).

Synthesis of methyl 2-(6-(2-(1H-indol-3-yl)ethylamino)-2-(5-fluoropyridin-3-yl)-9H-purin-9-yl)propanoate (d)

A 150 ml pressure tube was charged with methyl 2-(6-(2-(1H-indol-3-yl)ethylamino)-2-chloro-9H-purin-9-yl)propanoate (c) (300 mg, 0.75 mmol), 5-fluoropyridin-3-ylboronic acid (159 mg, 1.1 mmol), tetrakis(triphenylphosphine)palladium(0) (87 mg, 0.075 mmol), $K_3PO_4$ (638 mg, 3.0 mmol), and anhydrous dioxane (15 mL). The pressure tube was sparged with nitrogen and was sealed, then the reaction mixture was heated at 130° C. for 6 h with stirring. Water was added to the cooled mixture, and the mixture was extracted with ethyl acetate (50 ml×3). The combined organic layers were washed with brine, dried over sodium sulfate, and concentrated. The residue was purified by silica gel chromatography (10 to 80% ethyl acetate in hexane eluant) to afford the title compound contaminated with a small amount of triphenylphosphine oxide. MS m/z 460.1 (M+1).

Synthesis of 2-(6-(2-(1H-indol-3-yl)ethylamino)-2-(5-fluoropyridin-3-yl)-9H-purin-9-yl)propan-1-ol Lithium aluminum hydride (230 mg, 6.1 mmol) was added in portions to a 0° C. solution of methyl 2-(6-(2-(1H-indol-3-yl)ethylamino)-2-(5-fluoropyridin-3-yl)-9H-purin-9-yl)propanoate (282 mg, 0.61 mmol) in anhydrous THF (15 mL). The stirred reaction mixture was allowed to warm to rt over 2 h, then water was added carefully. The mixture was extracted with EtOAc (50 ml×3). The organic fractions were combined, washed with brine, dried over sodium sulfate, and concentrated. The residue was purified by silica gel column chromatography (0 to 5% solvent B in dichloromethane; solvent B=2M ammonia in methanol) to afford the partially purified title product. This was further purified by preparative TLC (5% solvent B in dichloromethane) to provide the title compound as a white solid.

Examples 157R & 157S (R)-2-(6-(2-(1H-indol-3-yl)ethylamino)-2-(5-fluoropyridin-3-yl)-9H-purin-9-yl)propan-1-ol & (S)-2-(6-(2-(1H-indol-3-yl)ethylamino)-2-(5-fluoropyridin-3-yl)-9H-purin-9-yl)propan-1-ol

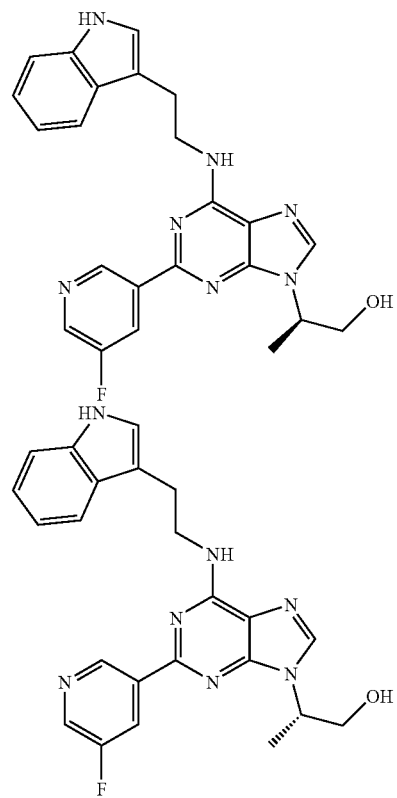

(R/S)-(6-(2-(1H-indol-3-yl)ethylamino)-2-(5-fluoropyridin-3-yl)-9H-purin-9-yl)propan-1-ol was separated into the individual enantiomers using preparative chiral HPLC on a 21×250 mm Lux-Cellulose-2 (Phenomenex) chiral column. A 3 mg/ml solution of the racemate in methanol was prepared and loaded onto the column with 0.5 ml solution per injection. The column was eluted with 85/7.5/7.5 hexane/ethanol/methanol at a flow rate of 20 mL/min for 25 min. Peaks 1 and 2 were eluted at 20 min and 22.5 min, respectively. Analytical chromatography was performed on a 4.6×100 mm Lux_Cellulose-2 (Phenomenex) chiral column, eluting with 90/5/5 hexane/ethanol/methanol at 1 mL/min for 20 min. Peaks 1 and 2 were eluted at 17.45 and 18.14 min, respectively.

Example 157R (R)-2-(6-(2-(1H-indol-3-yl)ethylamino)-2-(5-fluoropyridin-3-yl)-9H-purin-9-yl)propan-1-ol

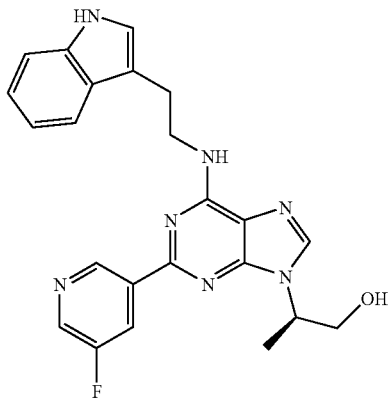 [SMILES: C[C@H](CO)n1cnc2c(NCCc3c[nH]c4ccccc34)nc(-c3cncc(F)c3)nc21]

Synthesis of (R)—N-(2-(1H-indol-3-yl)ethyl)-9-(1-(benzyloxy)propan-2-yl)-2-(5-fluoropyridin-3-yl)-9H-purin-6-amine (b)

Following, in succession, the procedures of Example 153b (using 2,6-dichloro-9H-purine and (S)-1-(benzyloxy)propan-2-ol as reactants), Example 153c (using tryptamine as reactant), and Example 153d (using 5-fluoropyridin-3-ylboronic acid as reactant), the title compound was obtained.

Synthesis of (R)-2-(6-(2-(1H-indol-3-yl)ethylamino)-2-(5-fluoropyridin-3-yl)-9H-purin-9-yl)propan-1-ol (c)

A solution of (R)—N-(2-(1H-indol-3-yl)ethyl)-9-(1-(benzyloxy)propan-2-yl)-2-(5-fluoropyridin-3-yl)-9H-purin-6-amine (b) (0.15 g, 0.29 mmol) in DCM (10 ml) was treated with BCl$_3$ (1M, 2.9 ml, 2.9 mmol) in DCM (10 ml) at −78° C. for 2 hr. 1N aqueous sodium hydroxide solution was added, and the mixture was extracted with DCM. The combined organic extracts were dried over sodium sulfate, filtered, and concentrated and the residue was purified by silica gel column chromatography (5% MeOH in DCM eluant) to provide the title compound. MS m/z 432.2 (M+1).

Example 157S (S)-2-(6-(2-(1H-indol-3-yl)ethylamino)-2-(5-fluoropyridin-3-yl)-9H-purin-9-yl)propan-1-ol

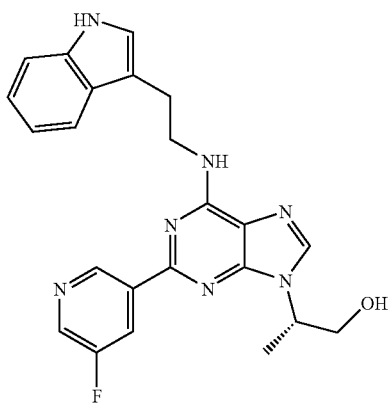 [SMILES: C[C@@H](CO)n1cnc2c(NCCc3c[nH]c4ccccc34)nc(-c3cncc(F)c3)nc21]

Following the procedure of Example 157R, but employing (R)-1-(benzyloxy)propan-2-ol in place of (S)-1-(benzyloxy)propan-2-ol, the title compound was prepared. MS m/z 432.2 (M+1).

Example 161

4-(2-(6-(5-Fluoropyridin-3-yl)-1-isopropyl-1H-imidazo[4,5-c]pyridin-4-ylamino)ethyl)phenol

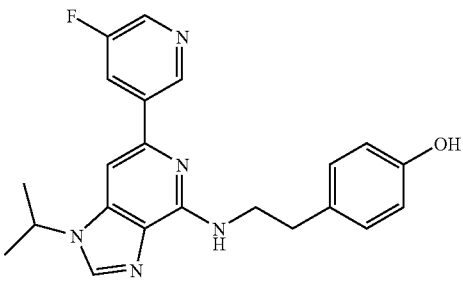 [SMILES: CC(C)n1cnc2c(NCCc3ccc(O)cc3)nc(-c3cncc(F)c3)cc21]

Synthesis of 4,6-dichloro-1-isopropyl-1H-imidazo[4,5-c]pyridine (b)

Following the procedure of Example 15b, 4,6-dichloro-1H-imidazo[4,5-c]pyridine (J. Het. Chem. 1965, 196-201) (0.19 g, 1.0 mmol) was reacted with 2-iodopropane. The residue was purified by silica gel chromatography (25 to 35% ethyl acetate in hexane eluant) to afford the title compound as a solid. MS m/z 230.2 (M+1).

Synthesis of 4-(2-(6-chloro-1-isopropyl-1H-imidazo[4,5-c]pyridin-4-ylamino)ethyl)phenol (c)

A mixture of 4,6-dichloro-1-isopropyl-1H-imidazo[4,5-c]pyridine (b) (40 mg, 0.17 mmol), tyramine (120 mg, 0.86 mmol), and 2-butanol (2 mL) was heated under microwave irradiation at 140° C. for 8 hr. The mixture was concentrated and the residue was purified by reverse-phase HPLC (C$_{18}$ column, eluting with ACN—H$_2$O 0.05% TFA) to afford the title compound as an off-white solid. MS m/z 331.1 (M+1).

Synthesis of 4-(2-(6-(5-fluoropyridin-3-yl)-1-isopropyl-1H-imidazo[4,5-c]pyridin-4-ylamino)ethyl)phenol (d)

A 5 ml microwave reaction vial was charged with 4-(2-(6-chloro-1-isopropyl-1H-imidazo[4,5-c]pyridin-4-ylamino)ethyl)phenol (c): (17 mg, 0.051 mmol), 5-fluoropyridin-3-ylboronic acid (72 mg, 0.51 mmol), and tetrakis(triphenylphosphine)palladium(0) (36 mg, 0.031 mmol). To this mixture was added toluene (1 ml), ethanol (0.5 ml) and aqueous sodium carbonate solution (2M, 0.5 ml). The vial was sealed and the reaction mixture was stirred at 140° C. under microwave irradiation for 2 hours. Water was added to the cooled mixture, which was extracted with ethyl acetate (5 ml×3). The organic fractions were combined, dried over sodium sulfate, and concentrated. The residue was purified by reverse-phase HPLC (C$_{18}$ column, eluting with ACN—H$_2$O 0.05% TFA) to afford the title compound as an off-white solid.

Example 177

4-(2-(5-(5-Fluoropyridin-3-yl)-3-isopropyl-3H-imidazo[4,5-b]pyridin-7-ylamino)ethyl)phenol

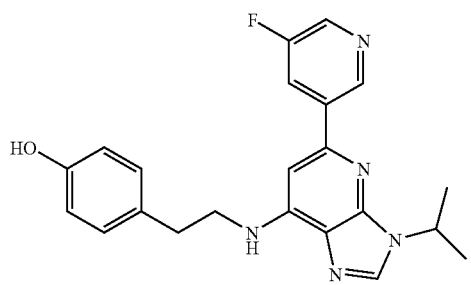 [SMILES: CC(C)n1cnc2c(NCCc3ccc(O)cc3)cc(-c3cncc(F)c3)nc21]

Synthesis of 5,7-dichloro-3-isopropyl-3H-imidazo[4,5-b]pyridine (b)

Following the procedure of Example 15b, 5,7-dichloro-3H-imidazo[4,5-b]pyridine (J. Med. Chem., 2007, 50, 828-834) (0.118 g, 0.624 mmol) was reacted with 2-iodopropane. The crude product mixture was purified by silica gel chromatography (25 to 35% ethyl acetate in hexane eluant) to afford a mixture of the title compound (major) and an isomeric product as a solid. MS m/z 230.2 (M+1).

Synthesis of 4-(2-(5-chloro-3-isopropyl-3H-imidazo[4,5-b]pyridin-7-ylamino)ethyl)phenol (c)

The product mixture containing 5,7-dichloro-3-isopropyl-3H-imidazo[4,5-b]pyridine (b) (40 mg, 0.17 mmol), tyramine (120 mg, 0.87 mmol), and 2-propanol (2 mL) was heated in a sealed vial at 140° C. for 72 hr. The mixture was concentrated, and the residue was purified by preparative TLC (1:2 hexanes/ethyl acetate eluant) to afford the title compound as an off-white solid. MS m/z 331.1 (M+1).

Synthesis of 4-(2-(5-(5-fluoropyridin-3-yl)-3-isopropyl-3H-imidazo[4,5-b]pyridin-7-ylamino)ethyl)phenol (d)

Following the procedure of Example 161d, 4-(2-(5-chloro-3-isopropyl-3H-imidazo[4,5-b]pyridin-7-ylamino)ethyl)phenol (c) (15 mg, 0.047 mmol) was reacted with 5-fluoropyridin-3-ylboronic acid. The crude residue was purified preparative TLC (1:1 hexanes/ethyl acetate eluant) to afford the title compound as an off-white solid.

By repeating the procedures described in the above examples, using appropriate starting materials, the following compounds of Formula I, as identified in Table 1, are obtained.

TABLE 1

| Example Number | Structure | Physicla Data $^1$H NMR and/or MS | $EC_{50}$ (% CD34+) μM |
|---|---|---|---|
| 1 | 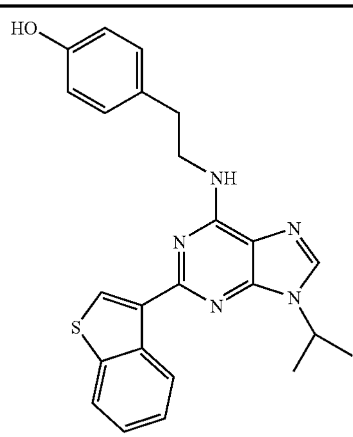 | $^1$H NMR (500 MHz, CDCl$_3$): δ = 9.20 (d, 1H), 8.58 (s, 1H), 8.00-7.80 (m, 2H), 7.55-7.38 (m, 3H), 7.11 (d, 2H), 6.72 (d, 2H), 6.18 (br, 1H), 5.01-4.68 (m, 1H), 4.02 (br, 2H), 3.00 (t, 2H), 1.68 (d, 6H); HRMS (EI) m/z 430.1698 (M + 1) | 0.12 |
| 2 | 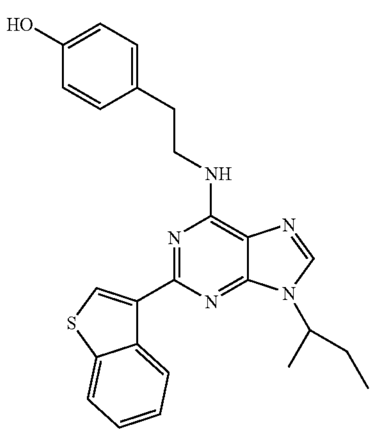 [SMILES: CCC(C)n1cnc2c(NCCc3ccc(O)cc3)nc(-c3csc4ccccc34)nc21] | $^1$H NMR (500 MHz, CDCl$_3$): δ = 9.22 (d, 1H), 8.53 (s, 1H), 7.92 (d, 1H), 7.80 (s, 1H), 7.52-7.33 (m, 3H), 7.13 (d, 2H), 6.74 (d, 2H), 6.08 (br, 1H), 4.80-4.62 (m, 1H), 4.02 (br, 2H), 3.01 (t, 2H), 2.20-1.90 (m, 2H), 1.77 (d, 3H), 0.92 (t, 3H); HRMS (EI) m/z 444.1857 (M + 1) | 0.03 |

TABLE 1-continued

| Example Number | Structure | Physical Data $^1$H NMR and/or MS | EC$_{50}$ (% CD34+) μM |
|---|---|---|---|
| 3 | 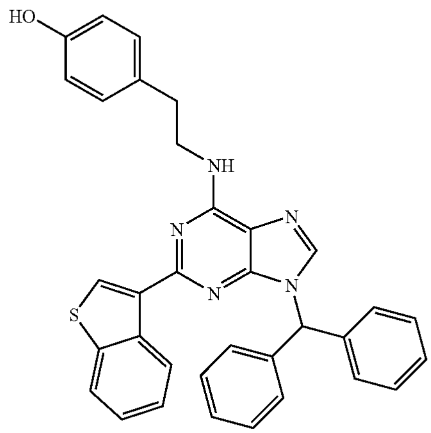 [SMILES: Oc1ccc(CCNc2nc(-c3csc4ccccc34)nc3c2ncn3C(c2ccccc2)c2ccccc2)cc1] | HRMS (EI) m/z 554.2005 (M + 1) | 0.15 |
| 4 | 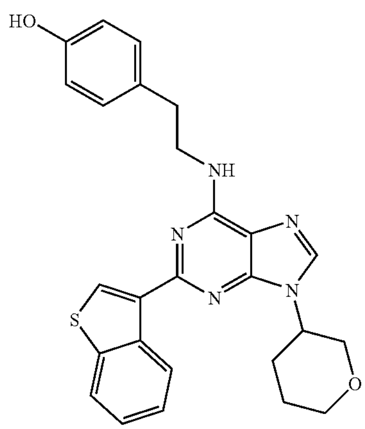 [SMILES: Oc1ccc(CCNc2nc(-c3csc4ccccc34)nc3c2ncn3C2CCCOC2)cc1] | HRMS (EI) m/z 472.1807 (M + 1) | 1.49 |
| 5 | 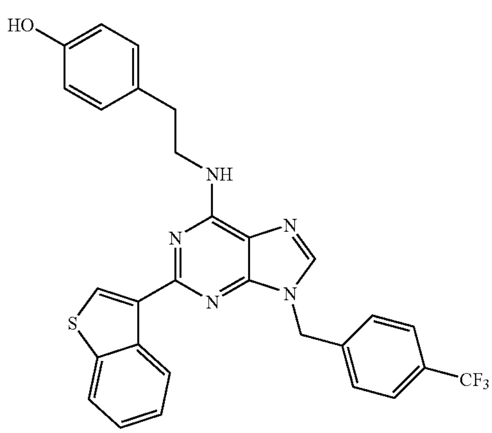 | HRMS (EI) m/z 546.1571 (M + 1) | 2.08 |

TABLE 1-continued

| Example Number | Structure | Physical Data ¹H NMR and/or MS | EC$_{50}$ (% CD34+) μM |
|---|---|---|---|
| 6 | 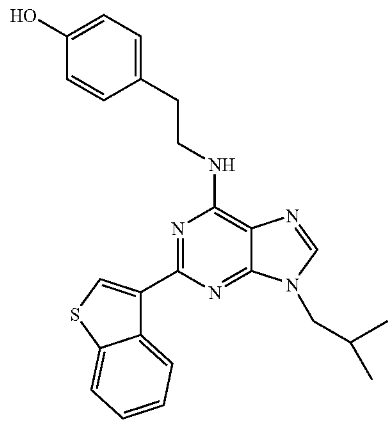 [SMILES: CC(C)Cn1cnc2c(NCCc3ccc(O)cc3)nc(-c3csc4ccccc34)nc21] | HRMS (EI) m/z 444.1857 (M + 1) | 2.53 |
| 7 | 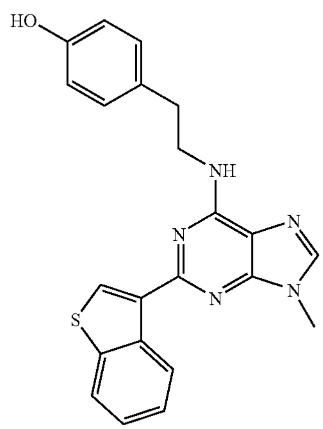 [SMILES: Cn1cnc2c(NCCc3ccc(O)cc3)nc(-c3csc4ccccc34)nc21] | HRMS (EI) m/z 402.1385 (M + 1) | 7.2 |
| 8 | 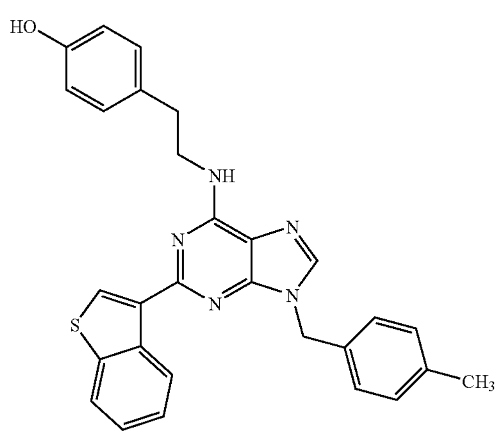 [SMILES: Cc1ccc(Cn2cnc3c(NCCc4ccc(O)cc4)nc(-c4csc5ccccc45)nc32)cc1] | HRMS (EI) m/z 492.1856 (M + 1) | 6.03 |

TABLE 1-continued

| Example Number | Structure | Physical Data $^1$H NMR and/or MS | EC$_{50}$ (% CD34+) μM |
|---|---|---|---|
| 9 | 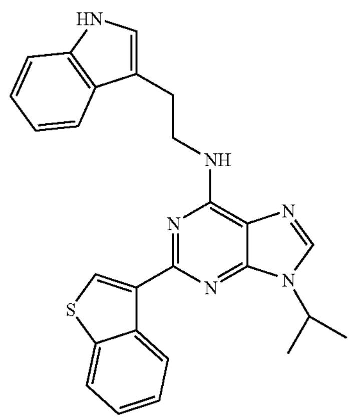 [SMILES: CC(C)n1cnc2c(NCCc3c[nH]c4ccccc34)nc(-c3csc4ccccc34)nc21] | $^1$H NMR (500 MHz, CDCl$_3$): δ = 9.21 (d, 1H), 8.48 (s, 1H), 8.02 (br, 1H), 7.89 (d, 1H), 7.79 (s, 1H), 7.70 (d, 1H), 7.50-7.07 (m, 6H), 5.82 (br, 1H), 5.00-4.88 (m, 1H), 4.13 (br, 2H), 3.22 (t, 2H), 1.69 (d, 6H); HRMS (EI) m/z 453.1857 (M + 1) | 0.02 |
| 10 | 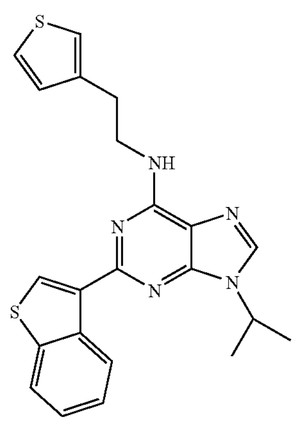 [SMILES: CC(C)n1cnc2c(NCCc3ccsc3)nc(-c3csc4ccccc34)nc21] | HRMS (EI) m/z 420.1315 (M + 1) | 1.38 |
| 11 | 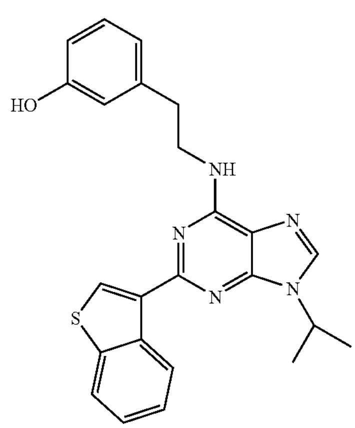 [SMILES: CC(C)n1cnc2c(NCCc3cccc(O)c3)nc(-c3csc4ccccc34)nc21] | HRMS (EI) m/z 430.1697 (M + 1) | 1.45 |

TABLE 1-continued

| Example Number | Structure | Physical Data $^1$H NMR and/or MS | EC$_{50}$ (% CD34+) μM |
|---|---|---|---|
| 12 | 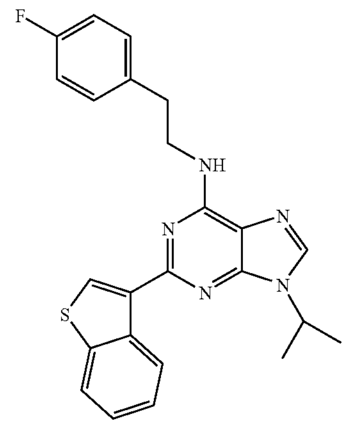 [SMILES: CC(C)n1cnc2c(NCCc3ccc(F)cc3)nc(-c3csc4ccccc34)nc21] | HRMS (EI) m/z 432.1655 (M + 1) | 1.76 |
| 13 | 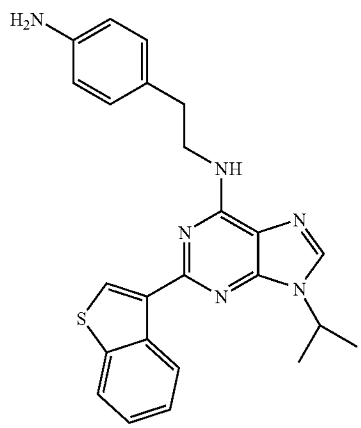 [SMILES: CC(C)n1cnc2c(NCCc3ccc(N)cc3)nc(-c3csc4ccccc34)nc21] | HRMS (EI) m/z 429.1853 (M + 1) | 5.75 |
| 14 | 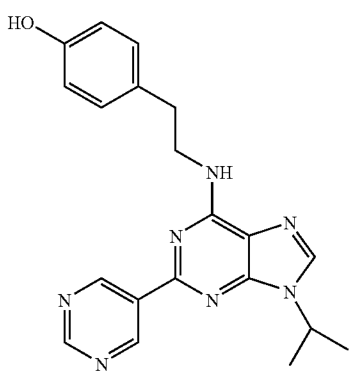 | HRMS (EI) m/z 376.1881 (M + 1) | 0.17 |

TABLE 1-continued

| Example Number | Structure | Physical Data ¹H NMR and/or MS | EC$_{50}$ (% CD34+) μM |
|---|---|---|---|
| 15 | 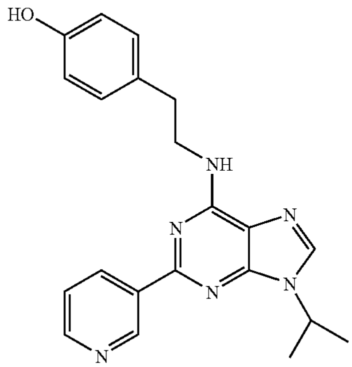 [SMILES: CC(C)n1cnc2c(NCCc3ccc(O)cc3)nc(-c3cncnc3)nc21] | ¹H NMR (400 MHz, CD$_3$OD) δ 9.57 (d, 1H), 8.85-8.83 (m, 1H), 8.59 (q, 1H), 8.16 (s, 1H), 7.57 (q, 1H), 7.13 (d, 2H), 6.72 (d, 2H), 4.98-4.91 (m, 1H), 3.91 (bs, 2H), 2.98 (t, 2H), 1.68 (d, 6H); HRMS (EI) m/z 375.1928 (M + 1) | 0.19 |
| 16 | 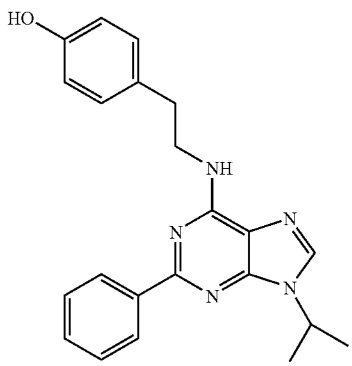 [SMILES: CC(C)n1cnc2c(NCCc3ccc(O)cc3)nc(-c3ccccc3)nc21] | HRMS (EI) m/z 374.1976 (M + 1) | 0.46 |
| 17 | 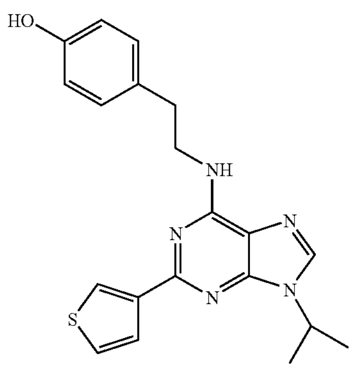 [SMILES: CC(C)n1cnc2c(NCCc3ccc(O)cc3)nc(-c3ccsc3)nc21] | HRMS (EI) m/z 380.1544 (M + 1) | 0.97 |
| 18 | 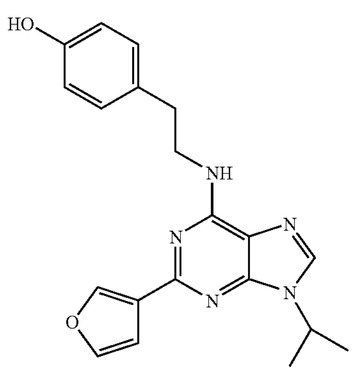 | HRMS (EI) m/z 364.1769 (M + 1) | 3.9 |

TABLE 1-continued

| Example Number | Structure | Physical Data ¹H NMR and/or MS | EC$_{50}$ (% CD34+) μM |
| --- | --- | --- | --- |
| 19 | 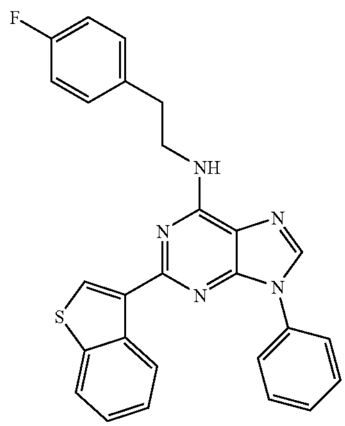 [SMILES: Fc1ccc(CCNc2nc(-c3csc4ccccc34)nc3c2ncn3-c2ccccc2)cc1] | HRMS (EI) m/z 466.1493 (M + 1) | 1.1 |
| 20 | 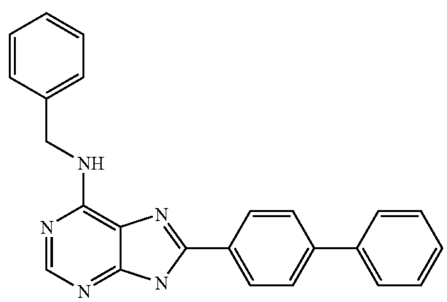 [SMILES: c1ccc(CNc2ncnc3[nH]c(-c4ccc(-c5ccccc5)cc4)nc23)cc1] | HRMS (EI) m/z 420.2184 (M + 1) | 7.8 |
| 21 | 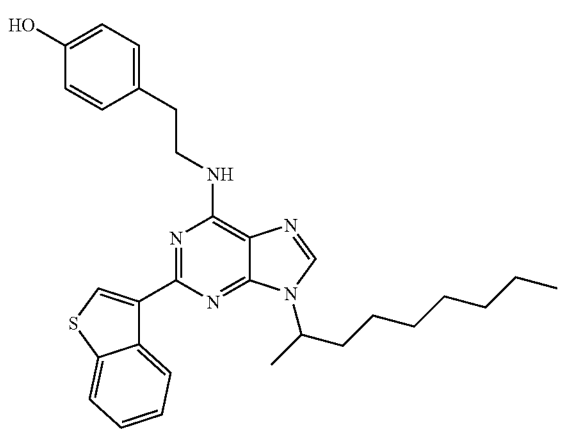 [SMILES: CCCCCCCC(C)n1cnc2c(NCCc3ccc(O)cc3)nc(-c3csc4ccccc34)nc21] | HRMS (EI) m/z 514.2638 (M + 1) | 0.13 |

TABLE 1-continued

| Example Number | Structure | Physical Data $^1$H NMR and/or MS | EC$_{50}$ (% CD34+) μM |
|---|---|---|---|
| 23 | 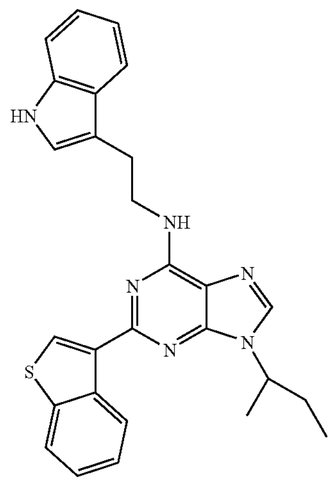 [SMILES: CCC(C)n1cnc2c(NCCc3c[nH]c4ccccc34)nc(-c3csc4ccccc34)nc21] | HRMS (EI) m/z 467.2013 (M + 1) | 0.019 |
| 31 | 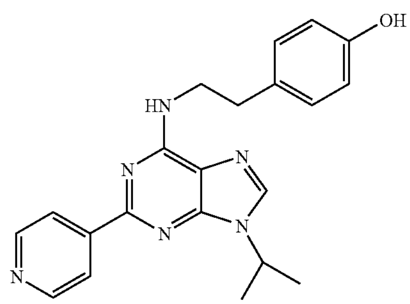 [SMILES: CC(C)n1cnc2c(NCCc3ccc(O)cc3)nc(-c3ccncc3)nc21] | MS m/z 375.2 (M + 1) | 0.66 |
| 32 | 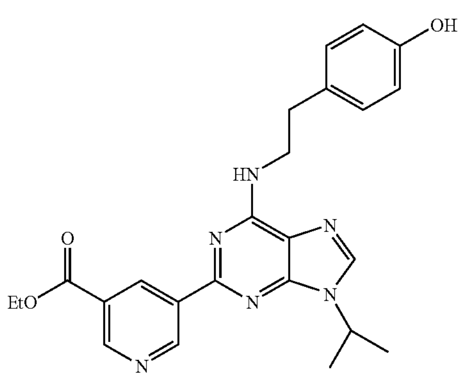 [SMILES: CCOC(=O)c1cncc(-c2nc(NCCc3ccc(O)cc3)c3ncn(C(C)C)c3n2)c1] | MS m/z 447.2 (M + 1) | 5.6 |
| 33 | 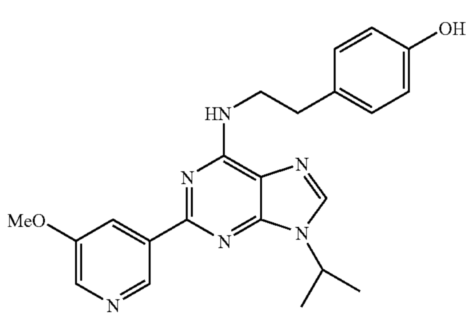 [SMILES: COc1cncc(-c2nc(NCCc3ccc(O)cc3)c3ncn(C(C)C)c3n2)c1] | MS m/z 405.2 (M + 1) | 0.27 |

TABLE 1-continued

| Example Number | Structure | Physical Data $^1$H NMR and/or MS | EC$_{50}$ (% CD34+) μM |
|---|---|---|---|
| 34 | 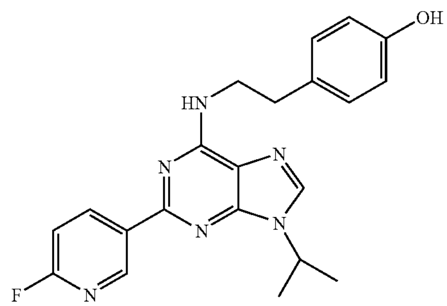 [SMILES: CC(C)n1cnc2c(NCCc3ccc(O)cc3)nc(-c3ccc(F)nc3)nc21] | MS m/z 393.2 (M + 1) | 0.16 |
| 35 | 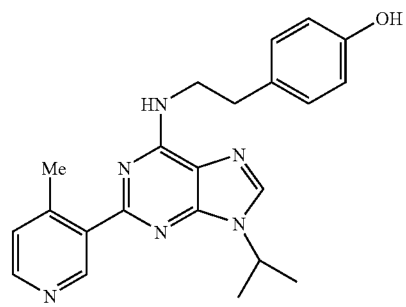 [SMILES: Cc1ccncc1-c1nc(NCCc2ccc(O)cc2)c2ncn(C(C)C)c2n1] | MS m/z 389.2 (M + 1) | 0.34 |
| 37 | 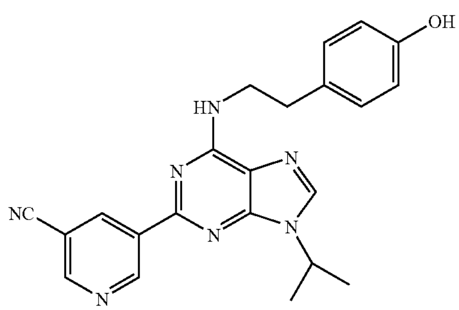 | MS m/z 400.2 (M + 1) | 0.024 |
| 38 | 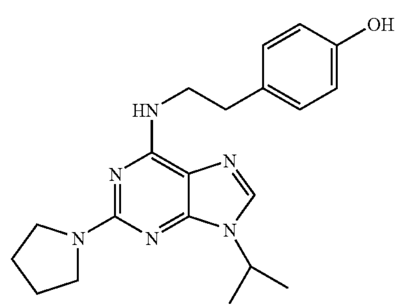 [SMILES: CC(C)n1cnc2c(NCCc3ccc(O)cc3)nc(N3CCCC3)nc21] | MS m/z 367.2 (M + 1) | 1.6 |
| 40 | 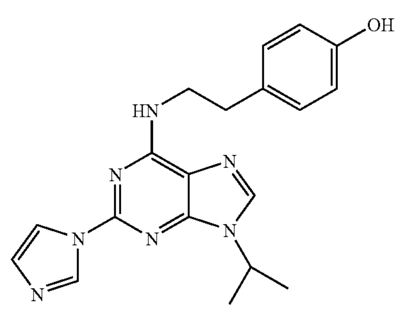 [SMILES: CC(C)n1cnc2c(NCCc3ccc(O)cc3)nc(-n3ccnc3)nc21] | MS m/z 364.2 (M + 1) | 0.26 |

TABLE 1-continued

| Example Number | Structure | Physical Data ¹H NMR and/or MS | $EC_{50}$ (% CD34+) μM |
|---|---|---|---|
| 42 | 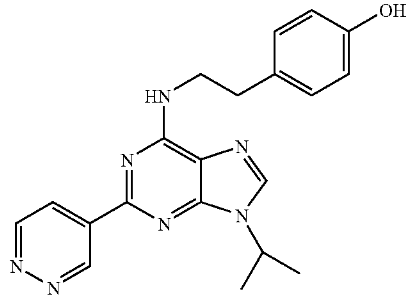 [SMILES: CC(C)n1cnc2c(NCCc3ccc(O)cc3)nc(-c3ccnnc3)nc21] | MS m/z 376.2 (M + 1) | 0.64 |
| 43 | 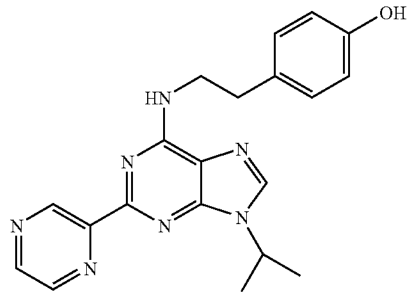 [SMILES: CC(C)n1cnc2c(NCCc3ccc(O)cc3)nc(-c3cnccn3)nc21] | MS m/z 376.2 (M + 1) | 2.4 |
| 44 | 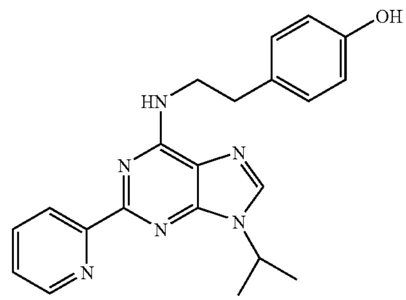 [SMILES: CC(C)n1cnc2c(NCCc3ccc(O)cc3)nc(-c3ccccn3)nc21] | MS m/z 375.2 (M + 1) | 1.7 |
| 45 | 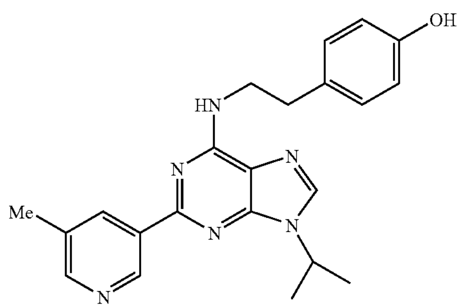 | MS m/z 389.2 (M + 1) | 0.063 |
| 46 | 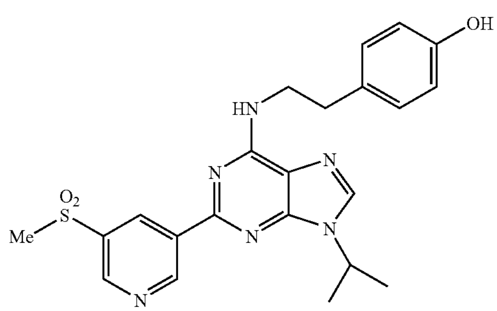 | MS m/z 453.2 (M + 1) | 0.65 |

TABLE 1-continued

| Example Number | Structure | Physicla Data ¹H NMR and/or MS | EC$_{50}$ (% CD34+) μM |
|---|---|---|---|
| 48 | 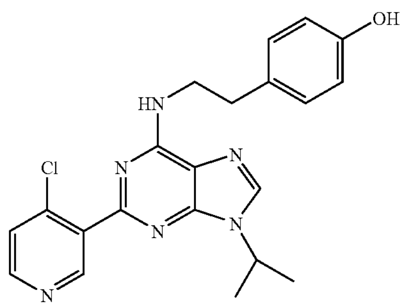 [SMILES: CC(C)n1cnc2c(NCCc3ccc(O)cc3)nc(-c3cnccc3Cl)nc21] | MS m/z 409.2 (M + 1) | 0.51 |
| 50 | 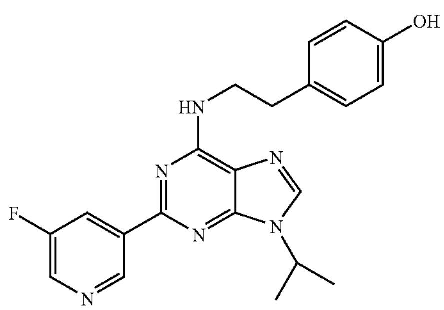 [SMILES: CC(C)n1cnc2c(NCCc3ccc(O)cc3)nc(-c3cncc(F)c3)nc21] | MS m/z 393.2 (M + 1) | 0.034 |
| 52 | 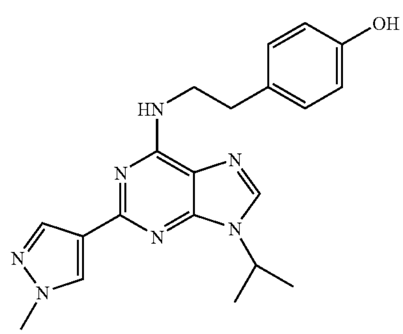 [SMILES: CC(C)n1cnc2c(NCCc3ccc(O)cc3)nc(-c3cnn(C)c3)nc21] | MS m/z 378.2 (M + 1) | |
| 55 | 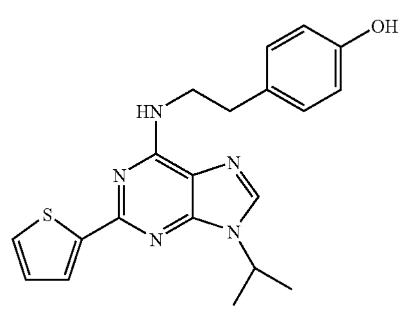 [SMILES: CC(C)n1cnc2c(NCCc3ccc(O)cc3)nc(-c3cccs3)nc21] | MS m/z 380.2 (M + 1) | 1.3 |
| 58 | 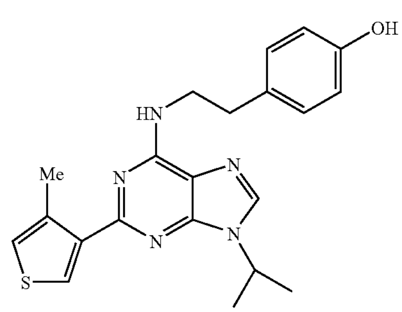 [SMILES: Cc1cscc1-c1nc(NCCc2ccc(O)cc2)c2ncn(C(C)C)c2n1] | MS m/z 394.2 (M + 1) | 0.24 |

TABLE 1-continued

| Example Number | Structure | Physicla Data ¹H NMR and/or MS | EC$_{50}$ (% CD34+) μM |
|---|---|---|---|
| 60 | 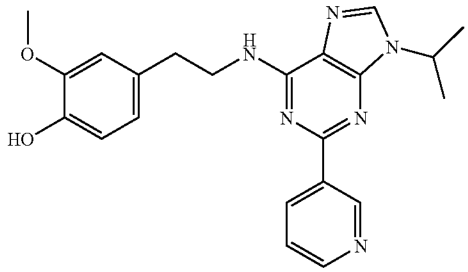 [SMILES: COc1cc(CCNc2nc(-c3cccnc3)nc3c2ncn3C(C)C)ccc1O] | MS m/z 405.1 (M + 1) | 3.2 |
| 61 | 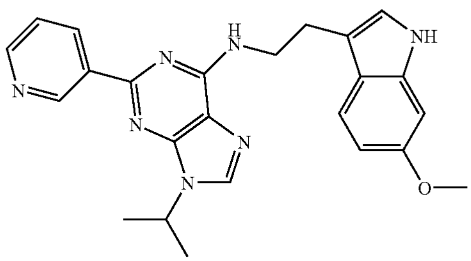 [SMILES: COc1ccc2c(CCNc3nc(-c4cccnc4)nc4c3ncn4C(C)C)c[nH]c2c1] | MS m/z 428.1 (M + 1) | 0.13 |
| 62 | 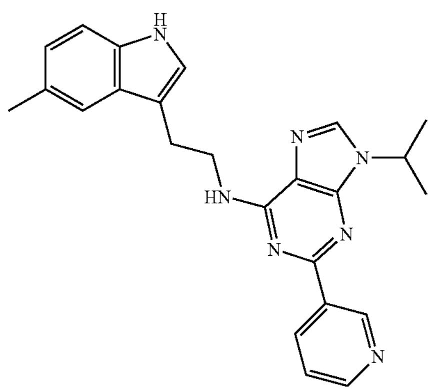 [SMILES: Cc1ccc2[nH]cc(CCNc3nc(-c4cccnc4)nc4c3ncn4C(C)C)c2c1] | MS m/z 412.1 (M + 1) | 0.72 |
| 70 | 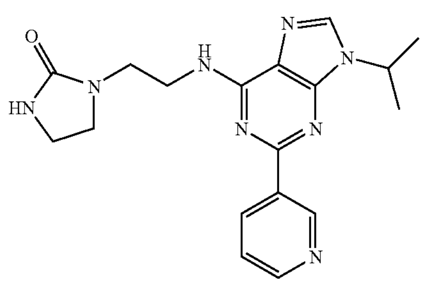 [SMILES: CC(C)n1cnc2c(NCCN3CCNC3=O)nc(-c3cccnc3)nc21] | MS m/z 367.2 (M + 1) | 2.7 |
| 72 | 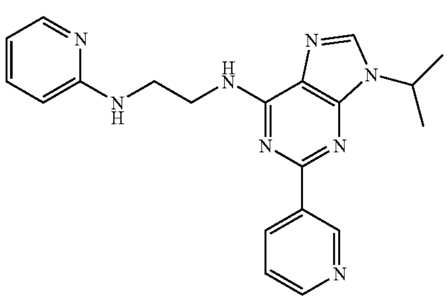 [SMILES: CC(C)n1cnc2c(NCCNc3ccccn3)nc(-c3cccnc3)nc21] | MS m/z 375.2 (M + 1) | 6.3 |

TABLE 1-continued

| Example Number | Structure | Physical Data $^1$H NMR and/or MS | EC$_{50}$ (% CD34+) μM |
|---|---|---|---|
| 73 | 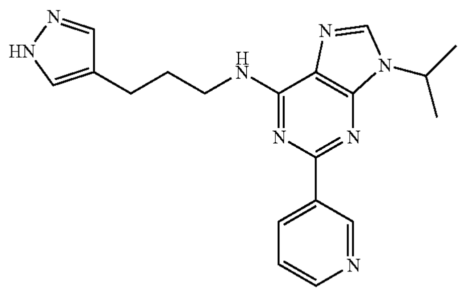 [SMILES: CC(C)n1cnc2c(NCCCc3cn[nH]c3)nc(-c3cccnc3)nc21] | MS m/z 363.2 (M + 1) | 8.2 |
| 76 | 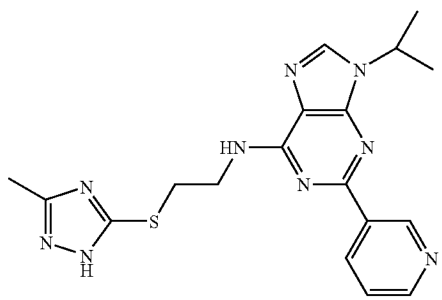 [SMILES: Cc1n[nH]c(SCCNc2nc(-c3cccnc3)nc3c2ncn3C(C)C)n1] | MS m/z 396.2 (M + 1) | 6.0 |
| 81 | 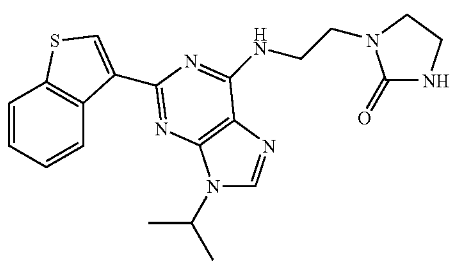 [SMILES: CC(C)n1cnc2c(NCCN3CCNC3=O)nc(-c3csc4ccccc34)nc21] | MS m/z 422.1 (M + 1) | 2.7 |
| 82 | 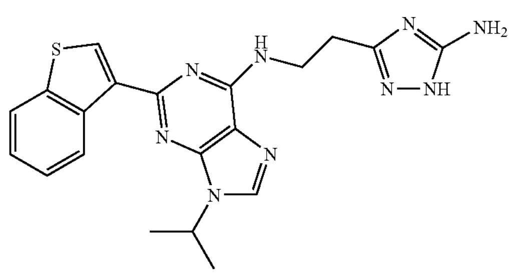 [SMILES: CC(C)n1cnc2c(NCCc3n[nH]c(N)n3)nc(-c3csc4ccccc34)nc21] | MS m/z 420.1 (M + 1) | 7.9 |
| 83 | 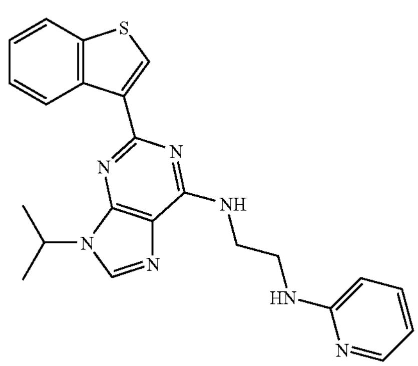 [SMILES: CC(C)n1cnc2c(NCCNc3ccccn3)nc(-c3csc4ccccc34)nc21] | MS m/z 430.1 (M + 1) | 7.1 |

TABLE 1-continued

| Example Number | Structure | Physical Data $^1$H NMR and/or MS | EC$_{50}$ (% CD34+) μM |
|---|---|---|---|
| 84 | 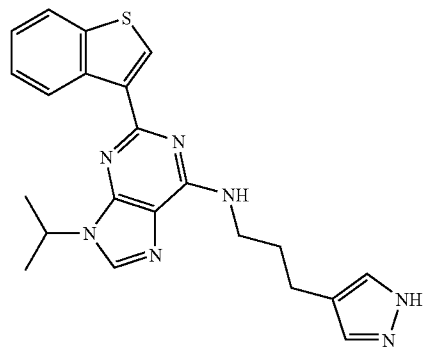 [SMILES: CC(C)n1cnc2c(NCCCc3cn[nH]c3)nc(-c3csc4ccccc34)nc21] | MS m/z 418.1 (M + 1) | 5.4 |
| 88 | 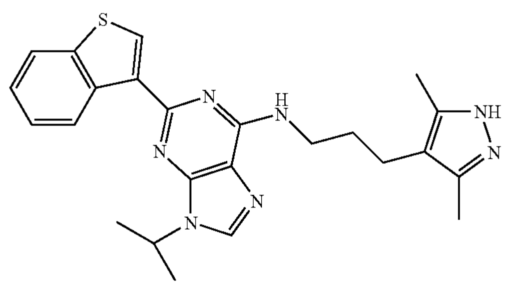 [SMILES: Cc1n[nH]c(C)c1CCCNc1nc(-c2csc3ccccc23)nc2c1ncn2C(C)C] | MS m/z 446.10 (M + 1) | 2.6 |
| 89 | 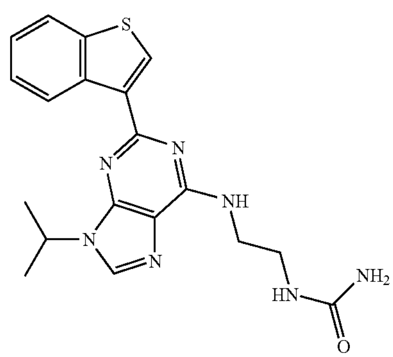 [SMILES: CC(C)n1cnc2c(NCCNC(N)=O)nc(-c3csc4ccccc34)nc21] | MS m/z 396.10 (M + 1) | 1.4 |
| 90 | 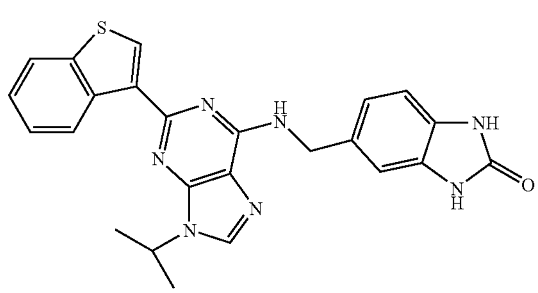 [SMILES: CC(C)n1cnc2c(NCc3ccc4[nH]c(=O)[nH]c4c3)nc(-c3csc4ccccc34)nc21] | MS m/z 456.2 (M + 1) | 3.3 |

TABLE 1-continued

| Example Number | Structure | Physical Data $^1$H NMR and/or MS | EC$_{50}$ (% CD34+) μM |
|---|---|---|---|
| 91 | 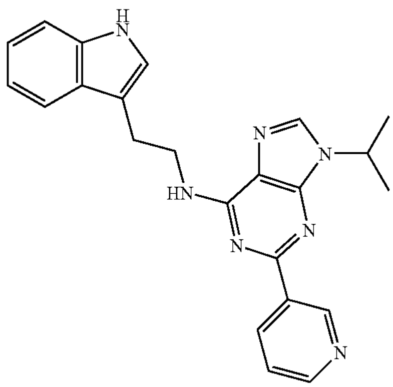 [SMILES: CC(C)n1cnc2c(NCCc3c[nH]c4ccccc34)nc(-c3cccnc3)nc21] | MS m/z 398.1 (M + 1) | 0.029 |
| 92 | 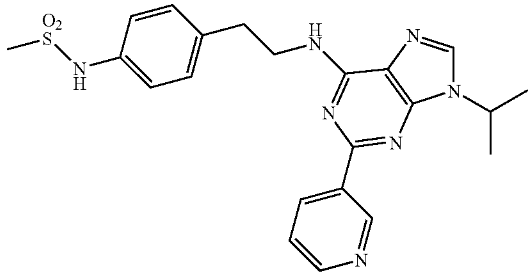 [SMILES: CC(C)n1cnc2c(NCCc3ccc(NS(C)(=O)=O)cc3)nc(-c3cccnc3)nc21] | MS m/z 452.2 (M + 1) | 7.1 |
| 93S | 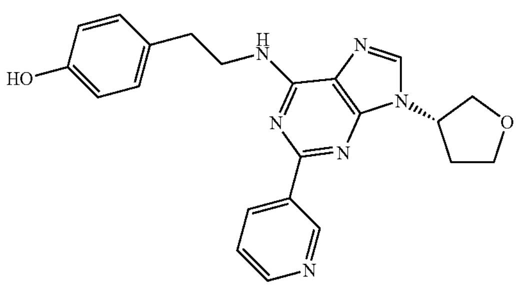 [SMILES: Oc1ccc(CCNc2nc(-c3cccnc3)nc3c2ncn3[C@H]2CCOC2)cc1] | MS m/z 403.1 (M + 1) | 1.1 |
| 93R | 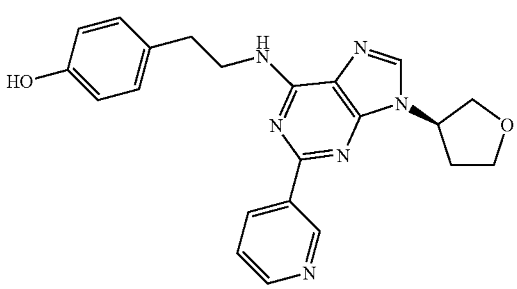 [SMILES: Oc1ccc(CCNc2nc(-c3cccnc3)nc3c2ncn3[C@@H]2CCOC2)cc1] | MS m/z 403.1 (M + 1) | 0.52 |
| 94 | 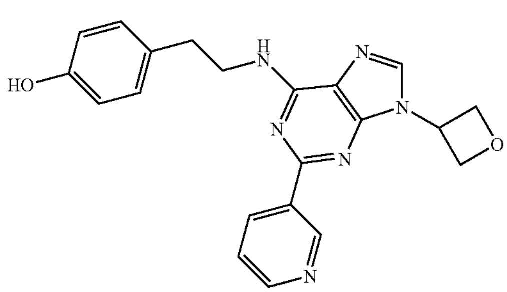 [SMILES: Oc1ccc(CCNc2nc(-c3cccnc3)nc3c2ncn3C2COC2)cc1] | MS m/z 389.1 (M + 1) | 0.97 |

TABLE 1-continued

| Example Number | Structure | Physical Data ¹H NMR and/or MS | EC$_{50}$ (% CD34+) μM |
|---|---|---|---|
| 95 | 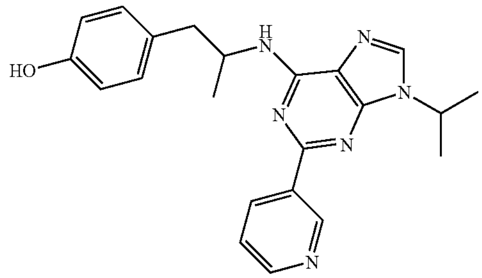 [SMILES: CC(Cc1ccc(O)cc1)Nc1nc(-c2cccnc2)nc2c1ncn2C(C)C] | MS m/z 389.1 (M + 1) | 2.3 |
| 98 | 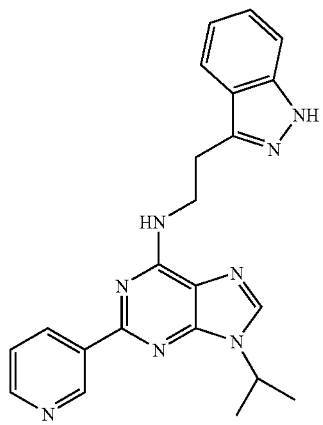 [SMILES: CC(C)n1cnc2c(NCCc3n[nH]c4ccccc34)nc(-c3cccnc3)nc21] | MS m/z 399.2 (M + 1) | 8.2 |
| 99 | 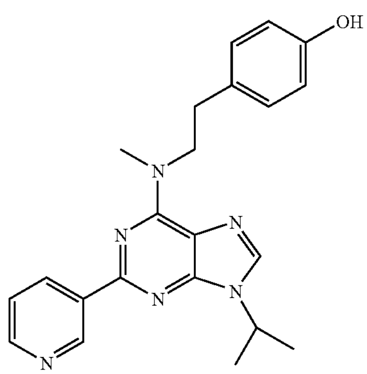 [SMILES: CC(C)n1cnc2c(N(C)CCc3ccc(O)cc3)nc(-c3cccnc3)nc21] | MS m/z 389.2 (M + 1) | 7.5 |
| 113 | 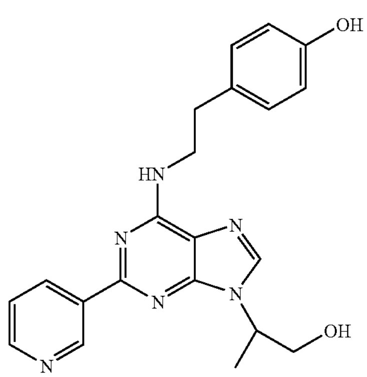 [SMILES: CC(CO)n1cnc2c(NCCc3ccc(O)cc3)nc(-c3cccnc3)nc21] | MS m/z 391.2 (M + 1) | 0.54 |

TABLE 1-continued

| Example Number | Structure | Physicla Data $^1$H NMR and/or MS | EC$_{50}$ (% CD34+) μM |
|---|---|---|---|
| 114 | 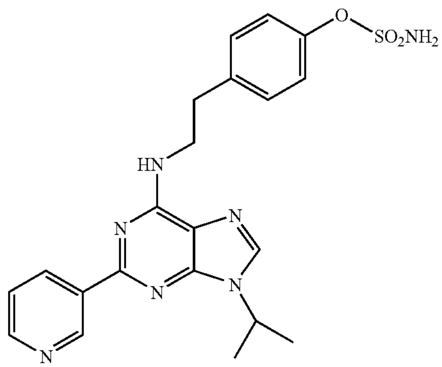 [SMILES: CC(C)n1cnc2c(NCCc3ccc(OS(N)(=O)=O)cc3)nc(-c3cccnc3)nc21] | MS m/z 454.1 (M + 1) | 1.1 |
| 118 | 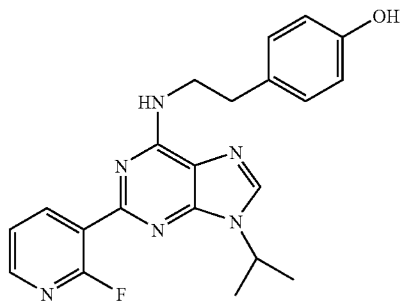 [SMILES: CC(C)n1cnc2c(NCCc3ccc(O)cc3)nc(-c3cccnc3F)nc21] | MS m/z 393.2 (M + 1) | 0.45 |
| 119 | 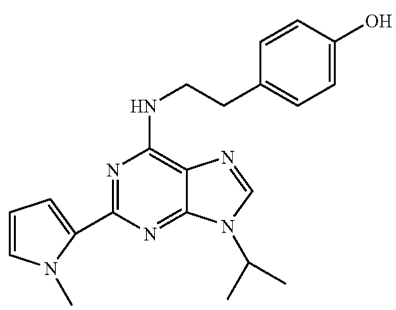 [SMILES: CC(C)n1cnc2c(NCCc3ccc(O)cc3)nc(-c3cccn3C)nc21] | MS m/z 377.2 (M + 1) | 1.4 |
| 120 | 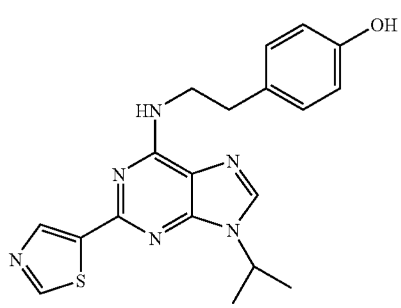 [SMILES: CC(C)n1cnc2c(NCCc3ccc(O)cc3)nc(-c3cncs3)nc21] | MS m/z 381.2 (M + 1) | 1.4 |

TABLE 1-continued

| Example Number | Structure | Physicla Data ¹H NMR and/or MS | EC$_{50}$ (% CD34+) μM |
|---|---|---|---|
| 121 | 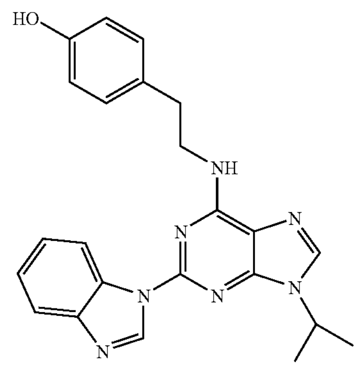 [SMILES: CC(C)n1cnc2c(NCCc3ccc(O)cc3)nc(-n3cnc4ccccc43)nc21] | MS m/z 414.2 (M + 1) | 0.086 |
| 122 | 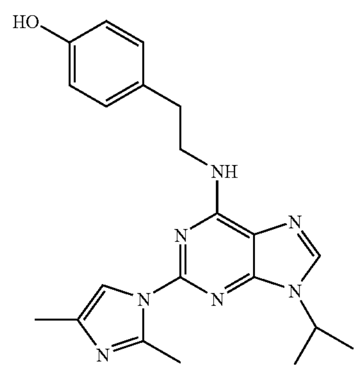 [SMILES: Cc1cn(-c2nc(NCCc3ccc(O)cc3)c3ncn(C(C)C)c3n2)c(C)n1] | MS m/z 414.2 (M + 1) | 0.42 |
| 123 | 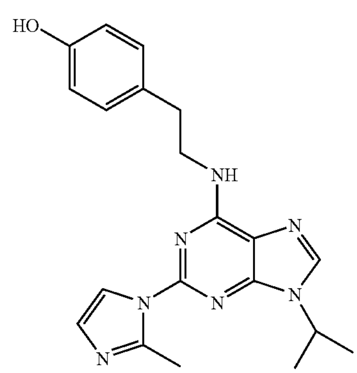 [SMILES: Cc1nccn1-c1nc(NCCc2ccc(O)cc2)c2ncn(C(C)C)c2n1] | ¹H NMR (400 MHz, DMSO): δ = 9.21 (br, 1H), 8.57 (t, 1H), 8.36 (s, 1H), 8.23 (d, 1H), 7.70 (d, 1H), 7.04 (d, 2H), 6.66 (d, 2H), 4.84-4.72 (m, 1H), 3.67 (q, 2H), 2.99 (s, 3H), 2.83 (t, 2H), 1.56 (d, 6H); MS m/z 378.2 (M + 1) | 0.066 |
| 124 | 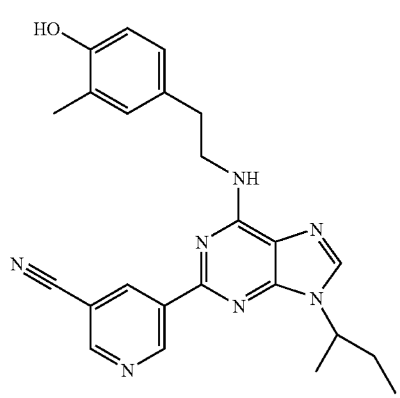 [SMILES: CCC(C)n1cnc2c(NCCc3ccc(O)c(C)c3)nc(-c3cncc(C#N)c3)nc21] | MS m/z 428.2 (M + 1) | 0.003 |

TABLE 1-continued

| Example Number | Structure | Physical Data ¹H NMR and/or MS | EC$_{50}$ (% CD34+) μM |
|---|---|---|---|
| 125 | 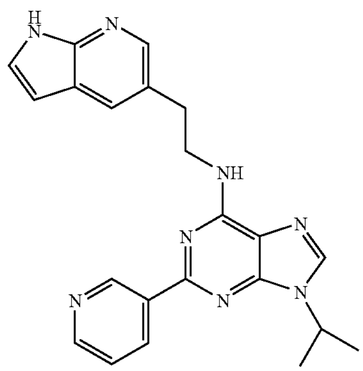 [SMILES: CC(C)n1cnc2c(NCCc3cnc4[nH]ccc4c3)nc(-c3cccnc3)nc21] | MS m/z 399.2 (M + 1) | |
| 126 | 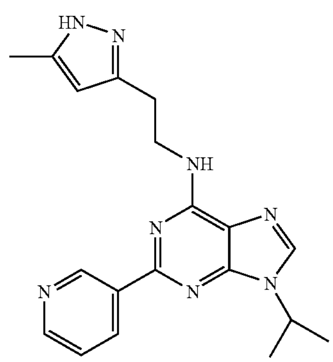 [SMILES: Cc1cc(CCNc2nc(-c3cccnc3)nc3c2ncn3C(C)C)n[nH]1] | MS m/z 363.2 (M + 1) | 5.0 |
| 127 | 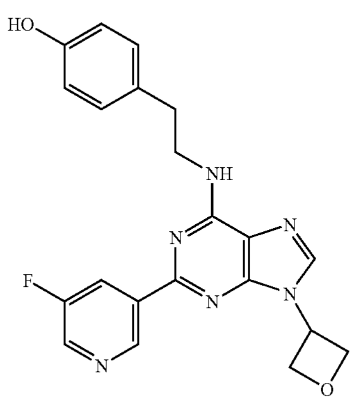 [SMILES: Oc1ccc(CCNc2nc(-c3cncc(F)c3)nc3c2ncn3C2COC2)cc1] | MS m/z 407.3 (M + 1) | 0.47 |
| 128 | 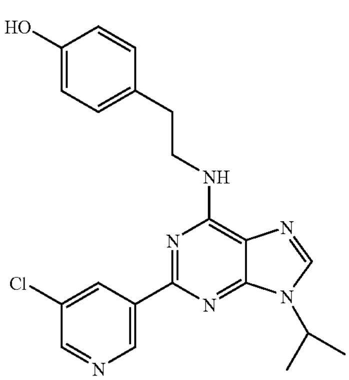 [SMILES: CC(C)n1cnc2c(NCCc3ccc(O)cc3)nc(-c3cncc(Cl)c3)nc21] | ¹H NMR (400 MHz, DMSO): δ = 9.47 (s, 1H), 8.71 (s, 1H), 8.67 (s, 1H), 8.32 (s, 1H), 8.04 (t, 1H), 7.10 (d, 2H), 6.69 (d, 2H), 4.91-4.81 (m, 1H), 3.80-3.70 (m, 2H), 2.86 (t, 2H), 1.58 (d, 6H); MS m/z 409.2 (M + 1) | 0.019 |

| Example Number | Structure | Physicla Data ¹H NMR and/or MS | EC₅₀ (% CD34+) μM |
|---|---|---|---|
| 129 | 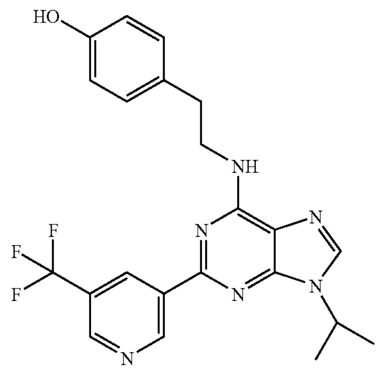 [SMILES: CC(C)n1cnc2c(NCCc3ccc(O)cc3)nc(-c3cncc(C(F)(F)F)c3)nc21] | MS m/z 443.2 (M + 1) | 0.12 |
| 130 | 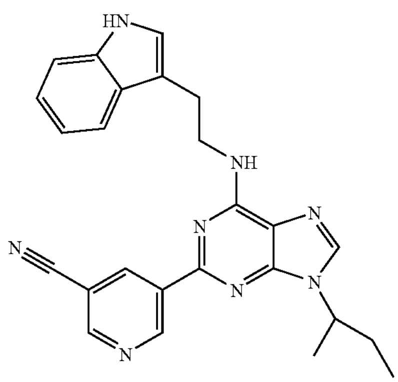 [SMILES: CCC(C)n1cnc2c(NCCc3c[nH]c4ccccc34)nc(-c3cncc(C#N)c3)nc21] | ¹H NMR (400 MHz, DMSO): δ = 10.82 (s, 1H), 9.74 (s, 1H), 9.10 (s, 1H), 8.99 (s, 1H), 8.32 (s, 1H), 8.13 (t, 1H), 7.65 (d, 1H), 7.32 (d, 1H), 7.22 (s, 1H), 7.06 (t, 1H), 6.99 (t, 1H), 4.72-4.60 (m, 1H), 3.96-3.85 (m, 2H), 3.08 (t, 2H), 2.08-1.88 (m, 2H), 1.58 (d, 3H), 0.77 (t, 3H); MS m/z 437.2 (M + 1) | 0.001 |
| 131 | 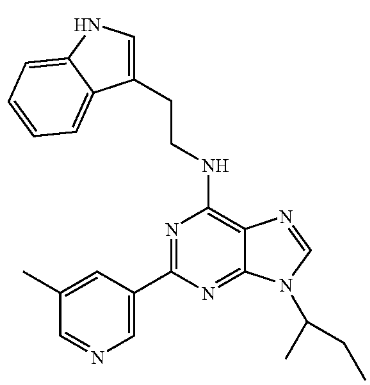 [SMILES: CCC(C)n1cnc2c(NCCc3c[nH]c4ccccc34)nc(-c3cncc(C)c3)nc21] | ¹H NMR (400 MHz, DMSO): δ = 10.83 (s, 1H), 9.40 (s, 1H), 8.97 (s, 1H), 8.76 (s, 1H), 8.35 (s, 1H), 8.18 (t, 1H), 7.62 (d, 1H), 7.33 (d, 1H), 7.23 (s, 1H), 7.06 (t, 1H), 6.97 (t, 1H), 4.72-4.60 (m, 1H), 3.96-3.82 (m, 2H), 3.10 (t, 2H), 2.53 (s, 3H), 2.09-1.89 (m, 2H), 1.58 (d, 3H), 0.77 (t, 3H); MS m/z 426.2 (M + 1) | 0.004 |
| 132R | 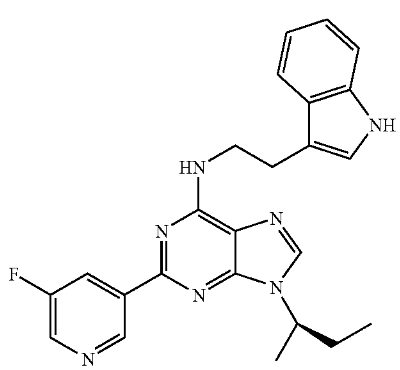 [SMILES: CC[C@@H](C)n1cnc2c(NCCc3c[nH]c4ccccc34)nc(-c3cncc(F)c3)nc21] | MS m/z 430.2 (M + 1) | 0.001 |

TABLE 1-continued

| Example Number | Structure | Physical Data ¹H NMR and/or MS | EC$_{50}$ (% CD34+) μM |
|---|---|---|---|
| 132S | 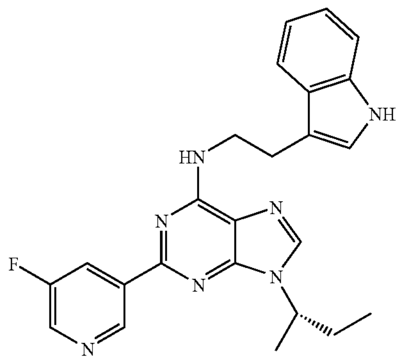 [SMILES: CC[C@H](C)n1cnc2c(NCCc3c[nH]c4ccccc34)nc(-c3cncc(F)c3)nc21] | MS m/z 430.2 (M + 1) | 0.002 |
| 132 | 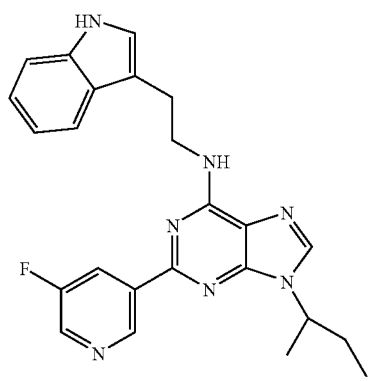 [SMILES: CCC(C)n1cnc2c(NCCc3c[nH]c4ccccc34)nc(-c3cncc(F)c3)nc21] | ¹H NMR (400 MHz, DMSO): δ = 10.83 (s, 1H), 9.42 (s, 1H), 8.66 (s, 1H), 8.41 (d, 1H), 8.31 (s, 1H), 8.09 (t, 1H), 7.64 (d, 1H), 7.34 (d, 1H), 7.22 (s, 1H), 7.07 (t, 1H), 6.97 (t, 1H), 4.68-4.60 (m, 1H), 3.92-3.84 (m, 2H), 3.08 (t, 2H), 2.08-1.90 (m, 2H), 1.58 (d, 3H), 0.77 (t, 3H); MS m/z 430.2 (M + 1) | 0.003 |
| 132R | 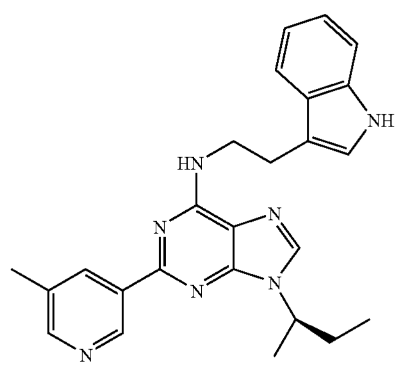 [SMILES: CC[C@@H](C)n1cnc2c(NCCc3c[nH]c4ccccc34)nc(-c3cncc(C)c3)nc21] | MS m/z 426.2 (M + 1) | 0.003 |
| 131R | 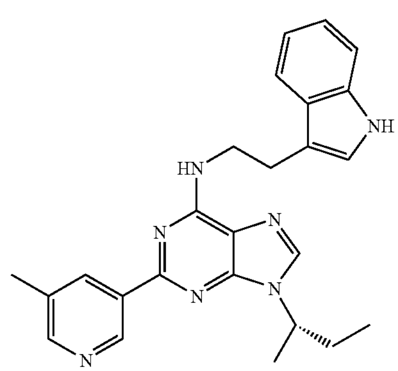 [SMILES: CC[C@H](C)n1cnc2c(NCCc3c[nH]c4ccccc34)nc(-c3cncc(C)c3)nc21] | MS m/z 426.2 (M + 1) | 0.003 |

TABLE 1-continued

| Example Number | Structure | Physical Data $^1$H NMR and/or MS | EC$_{50}$ (% CD34+) µM |
|---|---|---|---|
| 131S | 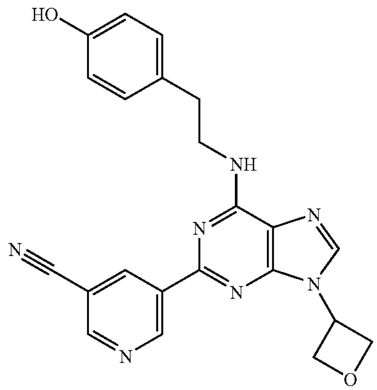 [SMILES: N#Cc1cncc(-c2nc(NCCc3ccc(O)cc3)c3ncn(C4COC4)c3n2)c1] | MS m/z 414.2 (M + 1) | 0.18 |
| 134 | 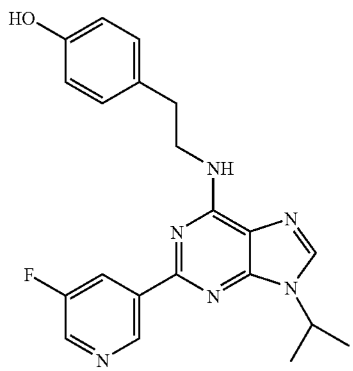 [SMILES: CC(C)n1cnc2c(NCCc3ccc(O)cc3)nc(-c3cncc(F)c3)nc21] | $^1$H NMR (400 MHz, DMSO): δ = 9.44 (s, 1H), 9.21 (s, 1H), 8.69 (d, 1H), 8.56 (t, 1H), 8.47 (d, 1H), 8.14 (s, 1H), 7.09 (d, 2H), 6.69 (d, 2H), 5.17-5.09 (m, 1H), 3.80-3.75 (m, 2H), 2.87 (t, 2H), 1.48 (d, 6H); MS m/z 393.2 (M + 1) | 0.20 |
| 135 | 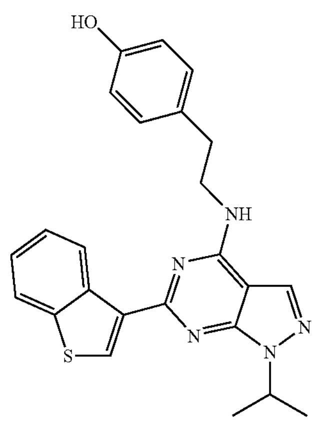 [SMILES: CC(C)n1ncc2c(NCCc3ccc(O)cc3)nc(-c3csc4ccccc34)nc21] | MS m/z 430.2 (M + 1) | 0.38 |
| 137 | 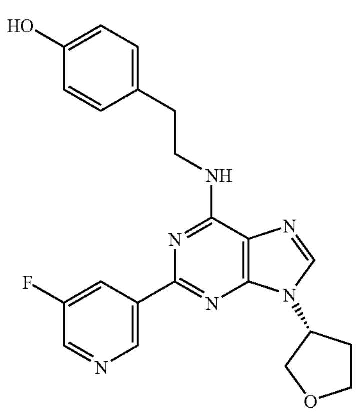 [SMILES: Oc1ccc(CCNc2nc(-c3cncc(F)c3)nc3c2ncn3[C@@H]2CCOC2)cc1] | MS m/z 421.1 (M + 1) | |

TABLE 1-continued

| Example Number | Structure | Physical Data ¹H NMR and/or MS | EC₅₀ (% CD34+) μM |
|---|---|---|---|
| 138 | (structure) | MS m/z 389.2 (M + 1) | 0.40 |
| 139 | (structure) | MS m/z 400.2 (M + 1) | 1.3 |
| 140 | (structure) | MS m/z 400.2 (M + 1) | 0.091 |
| 141 | (structure) | ¹H NMR (400 MHz, DMSO): δ = 9.42 (s, 1H), 8.63 (d, 1H), 8.42 (d, 1H), 7.79 (t, 1H), 7.35 (d, 1H), 7.09 (d, 2H), 6.70 (d, 2H), 6.61 (d, 1H), 5.08-5.00 (m, 1H), 3.76-3.70 (m, 2H), 2.87 (t, 2H), 1.47 (d, 6H); MS m/z 392.2 (M + 1) | 0.16 |

TABLE 1-continued

| Example Number | Structure | Physical Data ¹H NMR and/or MS | EC$_{50}$ (% CD34+) μM |
|---|---|---|---|
| 143 | 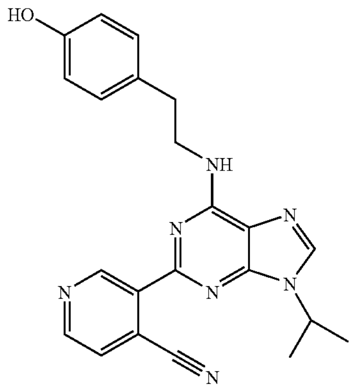 [SMILES: CC(C)n1cnc2c(NCCc3ccc(O)cc3)nc(-c3cnccc3C#N)nc21] | MS m/z 400.2 (M + 1) | 4.3 |
| 144 | 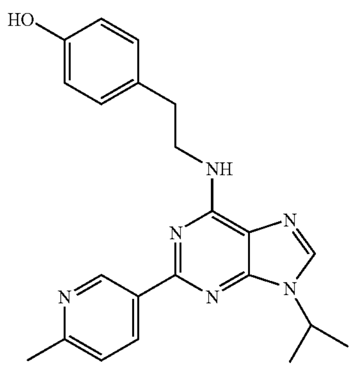 [SMILES: Cc1ccc(-c2nc(NCCc3ccc(O)cc3)c3ncn(C(C)C)c3n2)cn1] | MS m/z 389.2 (M + 1) | 0.16 |
| 145 | 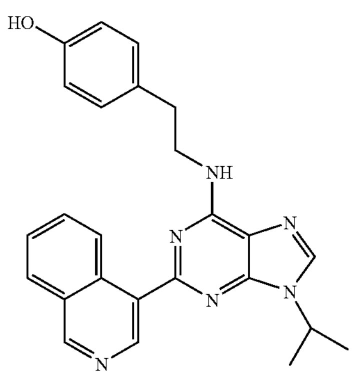 [SMILES: CC(C)n1cnc2c(NCCc3ccc(O)cc3)nc(-c3cncc4ccccc34)nc21] | MS m/z 425.2 (M + 1) | 5.4 |
| 146 | 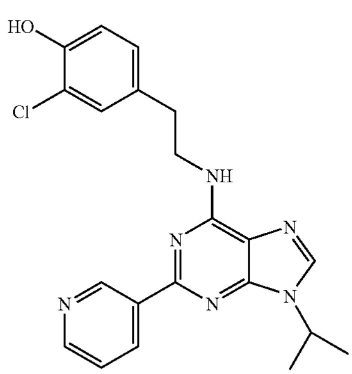 [SMILES: CC(C)n1cnc2c(NCCc3ccc(O)c(Cl)c3)nc(-c3cccnc3)nc21] | MS m/z 409.1 (M + 1) | 0.24 |

TABLE 1-continued

| Example Number | Structure | Physicla Data ¹H NMR and/or MS | EC$_{50}$ (% CD34+) μM |
|---|---|---|---|
| 147 | 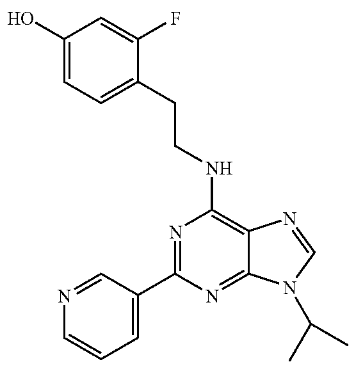 [SMILES: CC(C)n1cnc2c(NCCc3ccc(O)cc3F)nc(-c3cccnc3)nc21] | MS m/z 393.2 (M + 1) | 0.092 |
| 148 | 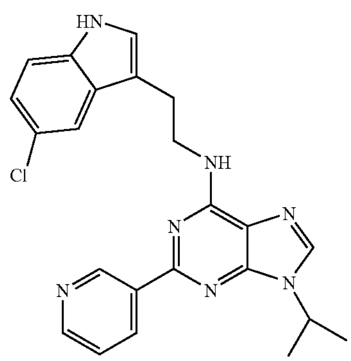 | MS m/z 432.2 (M + 1) | 0.75 |
| 149 | 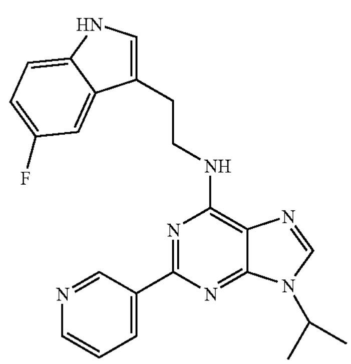 | MS m/z 416.2 (M + 1) | 0.52 |
| 150 | 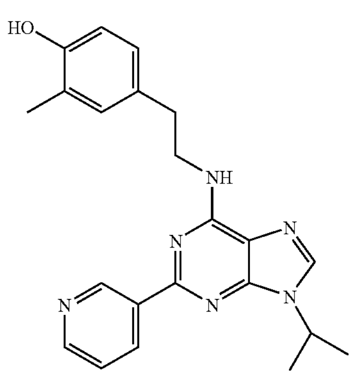 [SMILES: Cc1cc(CCNc2nc(-c3cccnc3)nc3c2ncn3C(C)C)ccc1O] | MS m/z 389.2 (M + 1) | 0.057 |

TABLE 1-continued
| Example Number | Structure | Physical Data $^1$H NMR and/or MS | $EC_{50}$ (% CD34+) μM |
|---|---|---|---|
| 151 | 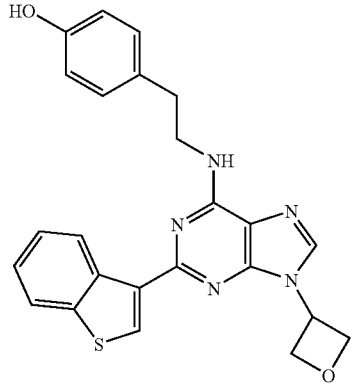 [SMILES: Oc1ccc(CCNc2nc(-c3csc4ccccc34)nc3c2ncn3C2COC2)cc1] | MS m/z 444.1 (M + 1) | 0.17 |
| 152 | 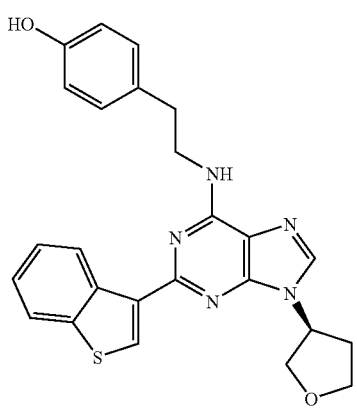 [SMILES: Oc1ccc(CCNc2nc(-c3csc4ccccc34)nc3c2ncn3[C@H]2CCOC2)cc1] | MS m/z 458.2 (M + 1) | 0.35 |
| 153 | 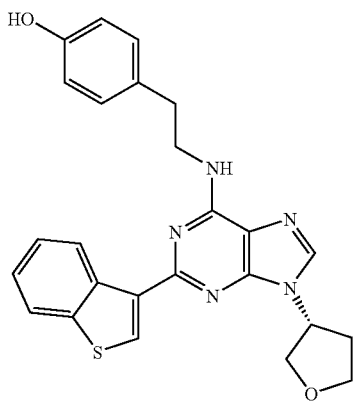 [SMILES: Oc1ccc(CCNc2nc(-c3csc4ccccc34)nc3c2ncn3[C@@H]2CCOC2)cc1] | 1H NMR (400 MHz, CD3OD): δ = 9.14 (s, 1H), 8.55 (s, 1H), 8.33 (s, 1H), 7.96 (d, 1H), 7.14 (t, 1H), 7.15 (d, 2H), 6.73 (d, 2H), 5.46-5.43 (m, 1H), 4.27-3.94 (m, 6H), 2.98 (t, 2H), 2.73-2.64 (m, 1H), 2.46-2.39 (m, 1H); MS m/z 458.2 (M + 1) | 0.22 |
| 157 | 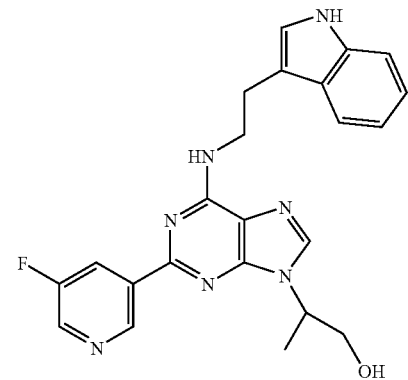 [SMILES: CC(CO)n1cnc2c(NCCc3c[nH]c4ccccc34)nc(-c3cncc(F)c3)nc21] | $^1$H NMR (400 MHz, CD$_3$OD): δ = 9.40 (s, 1H), 8.53-8.48 (m, 2H), 8.23 (s, 1H), 7.65 (d, 1H), 7.31 (d, 1H), 7.11 (s, 1H), 7.08-7.04 (m, 1H), 7.01-6.97 (m, 1H), 4.08-4.03 (m, 3H), 3.94 (dd, 1H), 3.35-3.30 (m, 1H), 3.19 (t, 2H), 1.68 (d, 3H); MS m/z 432.2 (M + 1) | 0.005 |

TABLE 1-continued

| Example Number | Structure | Physicla Data ¹H NMR and/or MS | EC$_{50}$ (% CD34+) µM |
|---|---|---|---|
| 157R | 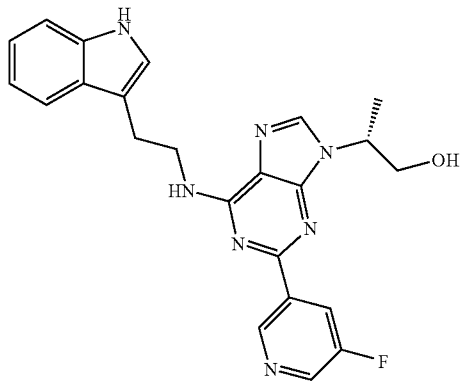 [SMILES: C[C@H](CO)n1cnc2c(NCCc3c[nH]c4ccccc34)nc(-c3cncc(F)c3)nc21] | MS m/z 432.2 (M + 1). | 0.008 |
| 157S | 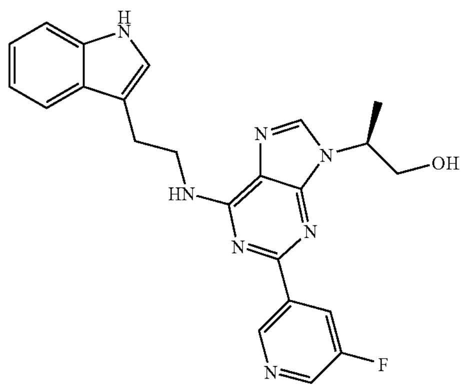 [SMILES: C[C@@H](CO)n1cnc2c(NCCc3c[nH]c4ccccc34)nc(-c3cncc(F)c3)nc21] | MS m/z 432.2 (M + 1) | 0.003 |
| 158 | 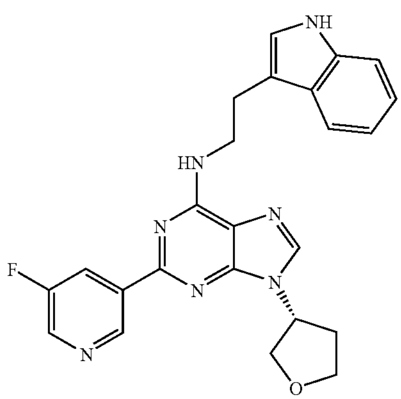 [SMILES: Fc1cncc(-c2nc(NCCc3c[nH]c4ccccc34)c3ncn([C@@H]4CCOC4)c3n2)c1] | MS m/z 444.2 (M + 1) | 0.012 |
| 159 | 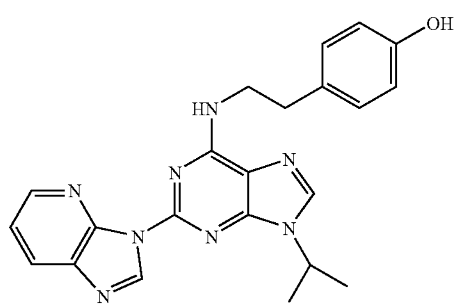 [SMILES: CC(C)n1cnc2c(NCCc3ccc(O)cc3)nc(-n3cnc4cccnc43)nc21] | MS m/z 415.2 (M + 1) | 0.59 |

TABLE 1-continued

| Example Number | Structure | Physicla Data ¹H NMR and/or MS | EC$_{50}$ (% CD34+) μM |
|---|---|---|---|
| 160 | 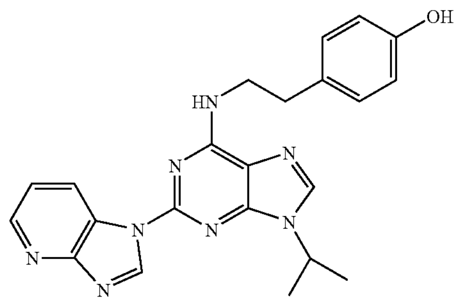 [SMILES: CC(C)n1cnc2c(NCCc3ccc(O)cc3)nc(-n3cnc4ncccc43)nc21] | MS m/z 415.2 (M + 1) | 1.9 |
| 161 | 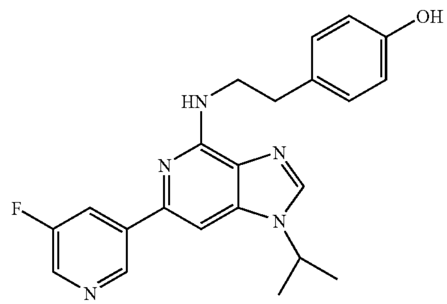 [SMILES: CC(C)n1cnc2c(NCCc3ccc(O)cc3)nc(-c3cncc(F)c3)cc21] | ¹H NMR (400 MHz, DMSO): δ = 9.11 (s, 1H), 8.64 (s, 1H), 8.51 (s, 1H), 8.30 (d, 1H), 7.74 (s, 1H), 7.09 (d, 2H), 6.69 (d, 2H), 4.88-4.76 (m, 1H), 3.88-3.78 (m, 2H), 2.88 (t, 2H), 1.56 (d, 6H); MS m/z 392.2 (M + 1) | 0.17 |
| 162 | 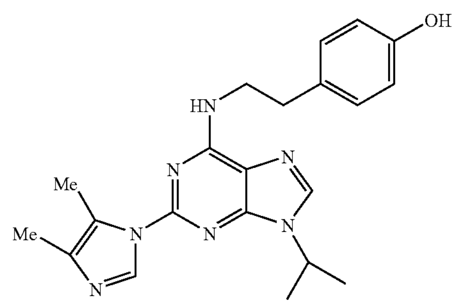 [SMILES: Cc1ncn(-c2nc(NCCc3ccc(O)cc3)c3ncn(C(C)C)c3n2)c1C] | MS m/z 392.2 (M + 1) | 0.14 |
| 166 | 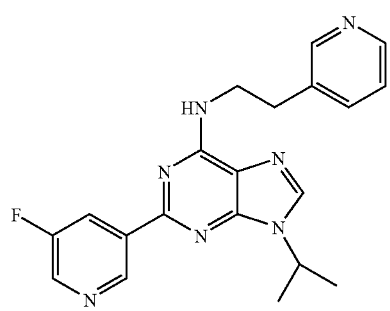 [SMILES: CC(C)n1cnc2c(NCCc3cccnc3)nc(-c3cncc(F)c3)nc21] | MS m/z 378.1 (M + 1) | 7.5 |
| 167 | 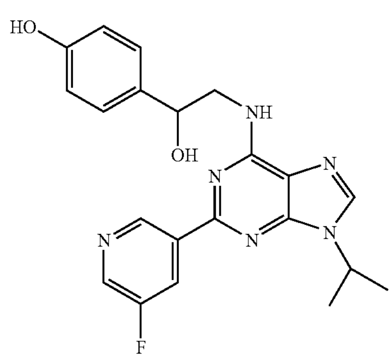 [SMILES: CC(C)n1cnc2c(NCC(O)c3ccc(O)cc3)nc(-c3cncc(F)c3)nc21] | MS m/z 409.2 (M + 1) | 0.29 |

TABLE 1-continued

| Example Number | Structure | Physicla Data ¹H NMR and/or MS | EC$_{50}$ (% CD34+) μM |
|---|---|---|---|
| 169 | 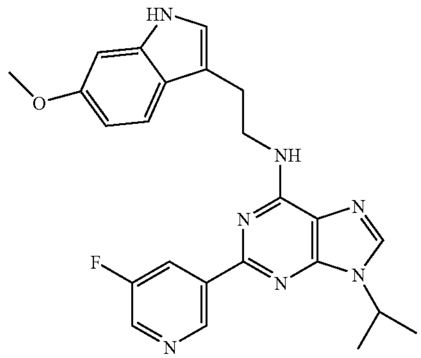 [SMILES: COc1ccc2c(CCNc3nc(-c4cncc(F)c4)nc4c3ncn4C(C)C)c[nH]c2c1] | MS m/z 446.2 (M + 1) | 0.044 |
| 170 | 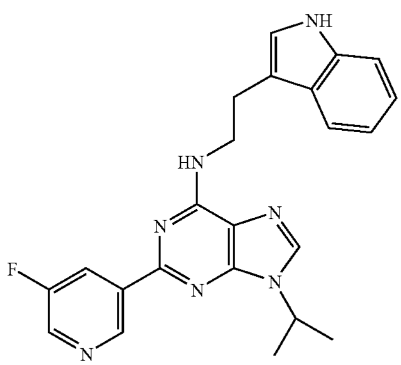 [SMILES: CC(C)n1cnc2c(NCCc3c[nH]c4ccccc34)nc(-c3cncc(F)c3)nc21] | MS m/z 416.2 (M + 1) | 0.006 |
| 172 | 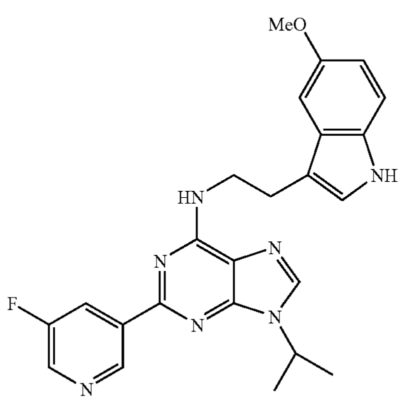 [SMILES: COc1ccc2[nH]cc(CCNc3nc(-c4cncc(F)c4)nc4c3ncn4C(C)C)c2c1] | MS m/z 446.2 (M + 1) | 0.42 |
| 173 | 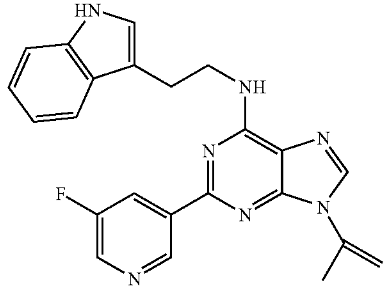 [SMILES: C=C(C)n1cnc2c(NCCc3c[nH]c4ccccc34)nc(-c3cncc(F)c3)nc21] | MS m/z 414.1 (M + 1) | 0.012 |

TABLE 1-continued

| Example Number | Structure | Physicla Data ¹H NMR and/or MS | EC$_{50}$ (% CD34+) μM |
|---|---|---|---|
| 174 | 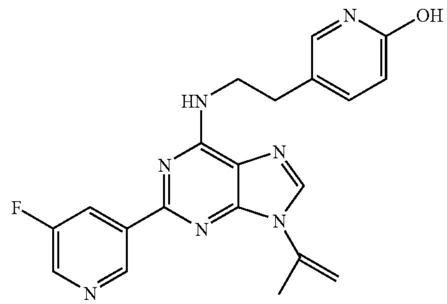 [SMILES: C=C(C)n1cnc2c(NCCc3ccc(O)nc3)nc(-c3cncc(F)c3)nc21] | MS m/z 394.2 (M + 1) | 2.2 |
| 175 | 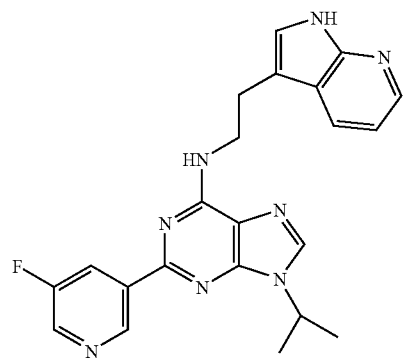 [SMILES: CC(C)n1cnc2c(NCCc3c[nH]c4ncccc34)nc(-c3cncc(F)c3)nc21] | MS m/z 417.2 (M + 1) | 0.42 |
| 176 | 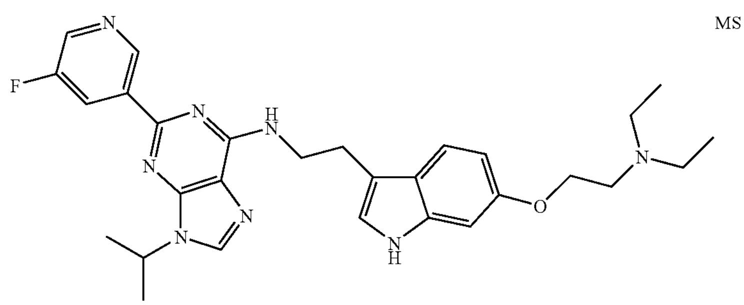 | MS m/z 513.3 (M + 1) | 1.1 |
| 177 | 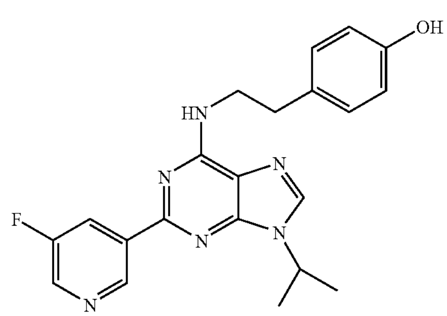 [SMILES: CC(C)n1cnc2c(NCCc3ccc(O)cc3)nc(-c3cncc(F)c3)nc21] | ¹H NMR (400 MHz, DMSO): δ = 9.18 (s, 1H), 9.15 (s, 1H), 8.57 (d, 1H), 8.29 (d, 1H), 8.26 (s, 1H), 7.11 (d, 2H), 7.01 (s, 1H), 6.79 (t, 1H), 6.95 (d, 2H), 4.92-4.84 (m, 1H), 3.72-3.62 (m, 2H), 2.83 (t, 2H), 1.56 (d, 6H); MS m/z 392.2 (M + 1) | 0.14 |
| 178 | 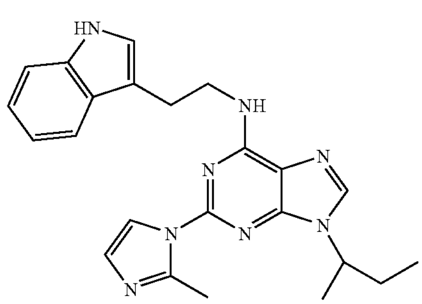 [SMILES: CCC(C)n1cnc2c(NCCc3c[nH]c4ccccc34)nc(-n3ccnc3C)nc21] | ¹H NMR (400 MHz, DMSO): δ = 10.83 (s, 1H), 8.67 (t, 1H), 8.37 (s, 1H), 8.15 (d, 1H), 7.71 (d, 1H), 7.57 (d, 1H), 7.33 (d, 1H), 7.20 (s, 1H), 7.06 (t, 1H), 6.96 (t, 1H), 4.60-4.48 (m, 1H), 3.86-3.76 (m, 2H), 3.06 (t, 2H), 2.96 (s, 3H), 2.05-1.85 (m, 2H), 1.56 (d, 3H), 0.76 (t, 3H); MS m/z 415.2 (M + 1) | 0.003 |

TABLE 1-continued

| Example Number | Structure | Physicla Data ¹H NMR and/or MS | EC$_{50}$ (% CD34+) μM |
|---|---|---|---|
| 180 | 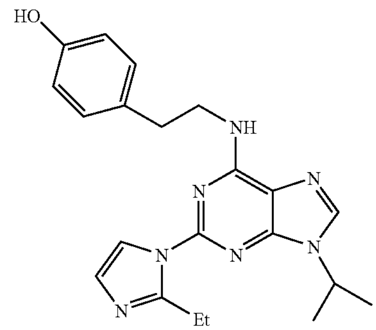 | MS m/z 392.2 (M + 1) | 0.13 |
| 181 | 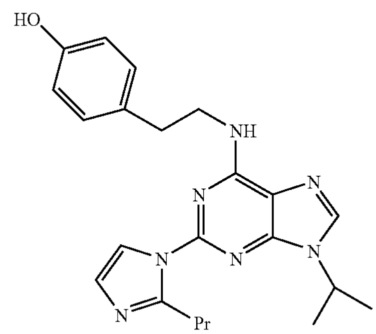 | MS m/z 406.2 (M + 1) | 2.5 |
| 182 | 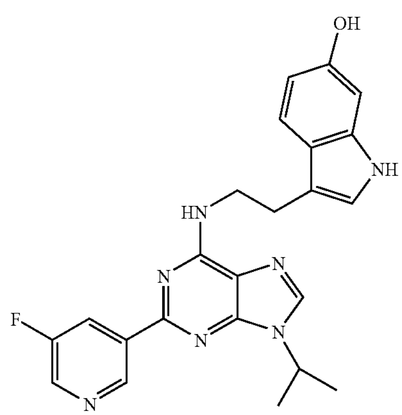 [SMILES: CC(C)n1cnc2c(NCCc3c[nH]c4cc(O)ccc34)nc(-c3cncc(F)c3)nc21] | MS m/z 432.2 (M + 1) | 5.1 |
| 183 | 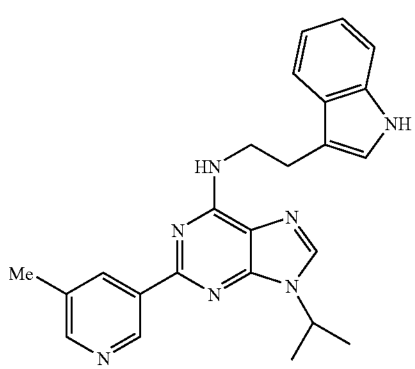 [SMILES: Cc1cncc(-c2nc(NCCc3c[nH]c4ccccc34)c3ncn(C(C)C)c3n2)c1] | ¹H NMR (400 MHz, DMSO): δ = 10.84 (s, 1H), 9.37 (s, 1H), 8.52 (s, 1H), 8.50 (s, 1H), 8.29 (s, 1H), 8.01 (t, 1H), 7.66 (d, 1H), 7.34 (d, 1H), 7.23 (m, 1H), 7.07 (t, 1H), 6.98 (t, 1H), 4.89-4.83 (m, 1H), 3.95-3.85 (m, 2H), 3.09 (t, 2H), 2.41 (s, 3H), 1.58 (d, 6H); MS m/z 412.2 (M + 1) | 0.01 |

TABLE 1-continued

| Example Number | Structure | Physicla Data ¹H NMR and/or MS | EC$_{50}$ (% CD34+) μM |
|---|---|---|---|
| 184 | 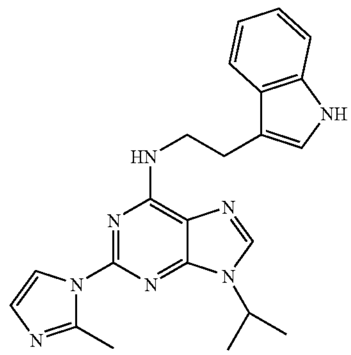 [SMILES: Cc1nccn1-c1nc(NCCc2c[nH]c3ccccc23)c2ncn(C(C)C)c2n1] | MS m/z 401.2 (M + 1) | 0.008 |
| 185 | 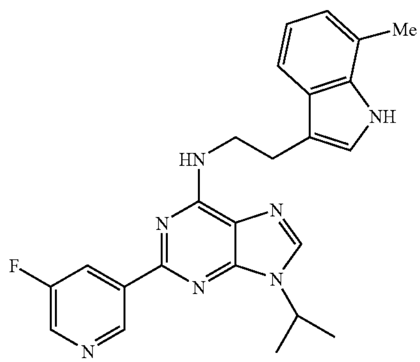 [SMILES: Cc1cccc2c(CCNc3nc(-c4cncc(F)c4)nc4c3ncn4C(C)C)c[nH]c12] | MS m/z 430.2 (M + 1) | 0.024 |
| 186 | 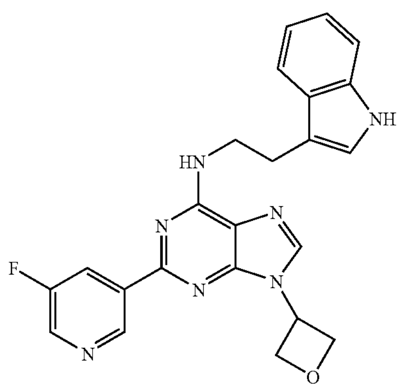 [SMILES: Fc1cncc(-c2nc(NCCc3c[nH]c4ccccc34)c3ncn(C4COC4)c3n2)c1] | MS m/z 430.2 (M + 1) | 0.007 |
| 187 | 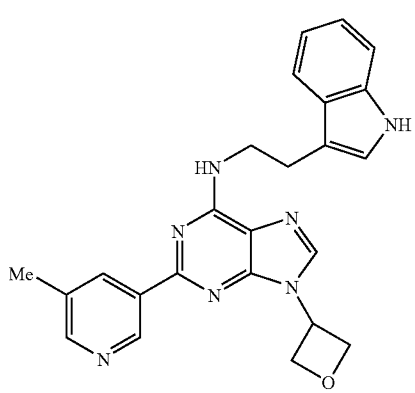 [SMILES: Cc1cncc(-c2nc(NCCc3c[nH]c4ccccc34)c3ncn(C4COC4)c3n2)c1] | ¹H NMR (400 MHz, DMSO): δ = 10.84 (s, 1H), 9.38 (s, 1H), 8.49 (m, 1H), 8.47 (s, 1H), 8.10 (t, 1H), 7.67 (d, 1H), 7.35 (d, 1H), 7.22 (m, 1H), 7.07 (t, 1H), 6.98 (t, 1H), 5.85-5.78 (m, 1H), 5.17 (t, 2H), 5.03 (t, 2H), 3.84-3.84 (m, 2H), 3.09 (t, 2H), 2.40 (s, 3H); MS m/z 426.2 (M + 1) | 0.034 |

TABLE 1-continued

| Example Number | Structure | Physicla Data $^1$H NMR and/or MS | EC$_{50}$ (% CD34+) µM |
|---|---|---|---|
| 188 | 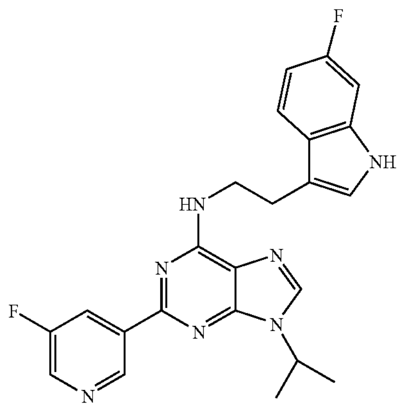 [SMILES: CC(C)n1cnc2c(NCCc3c[nH]c4cc(F)ccc34)nc(-c3cncc(F)c3)nc21] | MS m/z 434.2 (M + 1) | 0.005 |
| 189 | 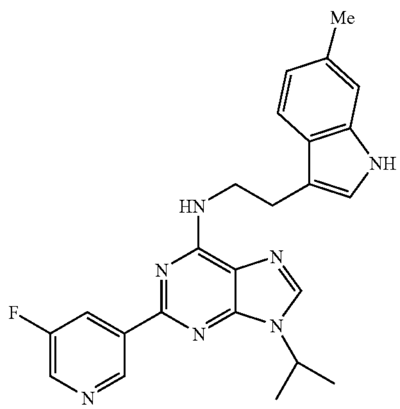 [SMILES: Cc1ccc2c(CCNc3nc(-c4cncc(F)c4)nc4c3ncn4C(C)C)c[nH]c2c1] | $^1$H NMR (400 MHz, DMSO): δ = 10.65 (s, 1H), 9.42 (s, 1H), 8.68 (m, 1H), 8.41 (d, 1H), 8.34 (s, 1H), 8.08 (t, 1H), 7.53 (d, 1H), 7.12 (m, 2H), 6.81 (d, 1H), 4.90-4.81 (m, 1H), 3.93-3.80 (m, 2H), 3.05 (t, 2H), 2.38 (s, 3H), 1.58 (d, 6H); MS m/z 432.0 (M + 1) | 0.026 |
| 190 | 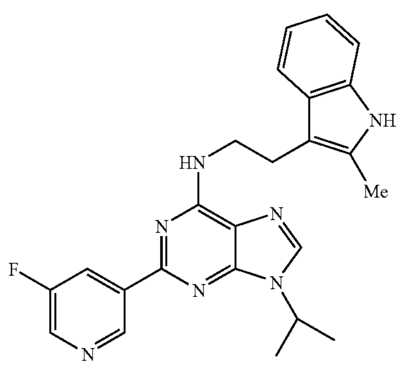 [SMILES: Cc1[nH]c2ccccc2c1CCNc1nc(-c2cncc(F)c2)nc2c1ncn2C(C)C] | $^1$H NMR (400 MHz, DMSO): δ = 10.71 (s, 1H), 9.42 (s, 1H), 8.67 (d, 1H), 8.38 (dd, 1H), 8.32 (s, 1H), 8.05 (t, 1H), 7.55 (d, 1H), 7.21 (d, 1H), 6.98 (t, 1H), 6.93 (t, 1H), 4.92-4.83 (m, 1H), 3.78-3.71 (m, 2H), 2.99 (t, 2H), 2.33 (s, 3H), 1.59 (d, 6H); MS m/z 430.2 (M +1) | 0.005 |
| 195 | 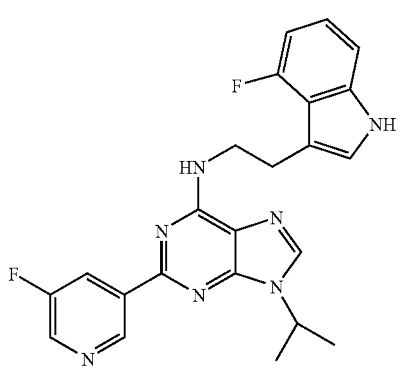 [SMILES: CC(C)n1cnc2c(NCCc3c[nH]c4cccc(F)c34)nc(-c3cncc(F)c3)nc21] | HPLC-MS calculated MS m/z 434.2 (M + 1) | 0.003 |

TABLE 1-continued

| Example Number | Structure | Physicla Data ¹H NMR and/or MS | EC$_{50}$ (% CD34+) µM |
|---|---|---|---|
| 196 | 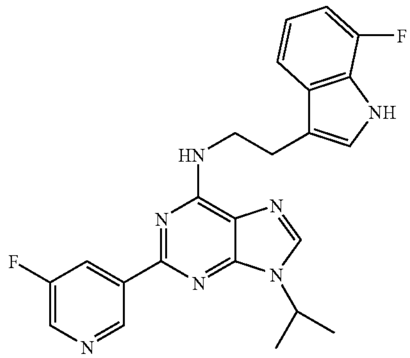 [SMILES: CC(C)n1cnc2c(NCCc3c[nH]c4c(F)cccc34)nc(-c3cncc(F)c3)nc21] | MS m/z 434.2 (M + 1) | 0.002 |
| 197 | 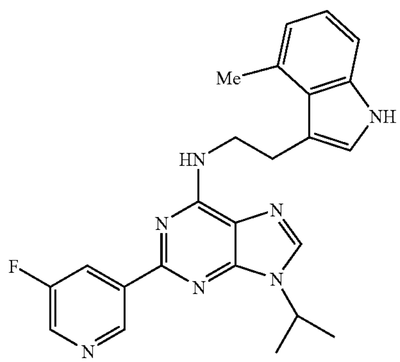 [SMILES: Cc1cccc2[nH]cc(CCNc3nc(-c4cncc(F)c4)nc4c3ncn4C(C)C)c12] | ¹H NMR (400 MHz, DMSO): δ = 10.79 (s, 1H), 9.37 (s, 1H), 8.64 (d, 1H), 8.39 (d, 1H), 8.31 (s, 1H), 8.06 (t, 1H), 7.15 (s, 1H), 7.13 (d, 1H), 6.90 (t, 1H), 6.69 (d, 1H), 4.90-4.83 (m, 1H), 3.83-3.87 (m, 2H), 3.24 (t, 2H), 2.65 (s, 3H), 1.57 (d, 6H); MS m/z 430.2 (M + 1) | 0.011 |
| 198 | 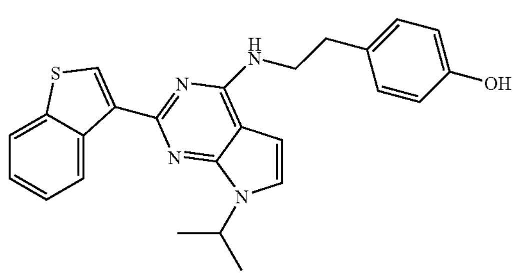 [SMILES: CC(C)n1ccc2c(NCCc3ccc(O)cc3)nc(-c3csc4ccccc34)nc21] | MS m/z 429.1 (M + 1) | 1.1 |
| 199 | 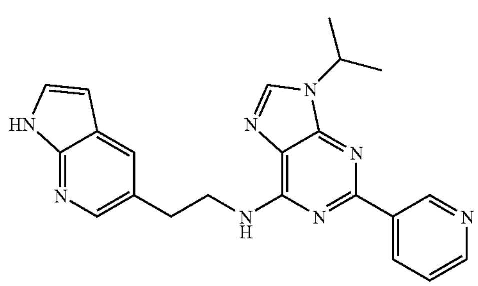 [SMILES: CC(C)n1cnc2c(NCCc3cnc4[nH]ccc4c3)nc(-c3cccnc3)nc21] | MS m/z 399.2 (M + 1) | 1.6 |
| 200 | 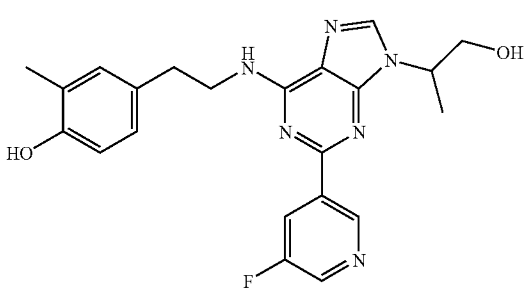 [SMILES: Cc1cc(CCNc2nc(-c3cncc(F)c3)nc3c2ncn3C(C)CO)ccc1O] | MS m/z 423.2 (M + 1) | 0.001 |

TABLE 1-continued

| Example Number | Structure | Physical Data ¹H NMR and/or MS | EC$_{50}$ (% CD34+) μM |
|---|---|---|---|
| 201 | 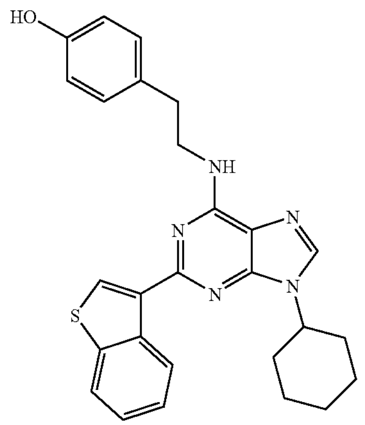 [SMILES: Oc1ccc(CCNc2nc(-c3csc4ccccc34)nc3c2ncn3C2CCCCC2)cc1] | | |
| 202 | 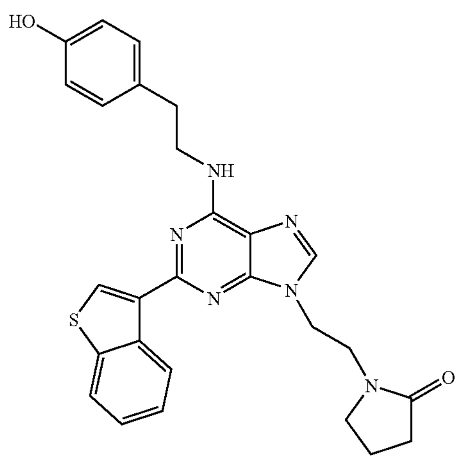 [SMILES: O=C1CCCN1CCn1cnc2c(NCCc3ccc(O)cc3)nc(-c3csc4ccccc34)nc21] | | |
| 203 | 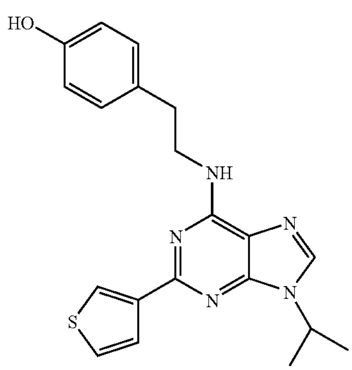 [SMILES: CC(C)n1cnc2c(NCCc3ccc(O)cc3)nc(-c3ccsc3)nc21] | | |

Affinity probe compounds related to the compounds of the invention can also be prepared, as described in the following examples.

Example 210

3-(2-(2-(benzo[b]thiophen-3-yl)-9-isopropyl-9H-purin-6-ylamino)ethyl)-1H-indol-5-yl 6-(5-((3aS,4S,6aR)-2-oxohexahydro-1H-thieno[3,4-d]imidazol-4-yl)pentanamido)hexanoate

Synthesis of 3-(2-(2-(benzo[b]thiophen-3-yl)-9-isopropyl-9H-purin-6-ylamino)ethyl)-1H-indol-5-yl 6-aminohexanoate (e)

To a solution of 3-(2-(2-(benzo[b]thiophen-3-yl)-9-isopropyl-9H-purin-6-ylamino)ethyl)-1H-indol-5-yl 6-(tert-butoxycarbonylamino)hexanoate (a) (80 mg, 0.117 mmol) in DCM (20 ml) was added TFA (5 ml). The reaction was stirred at rt for 3 hr. It was concentrated. Aqueous sodium carbonate solution was added and the mixture was extracted with DCM.

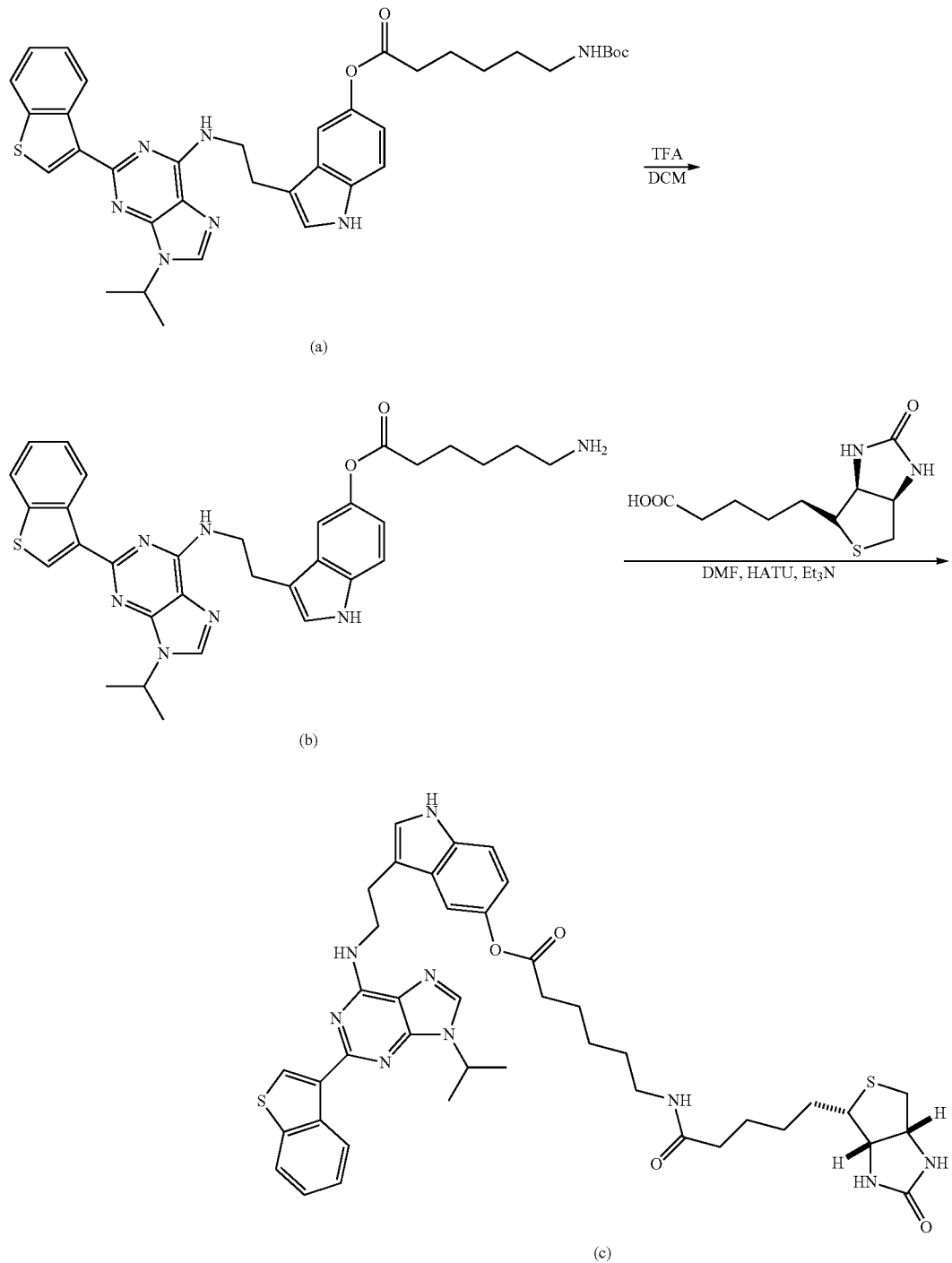

The organic fractions were combined, dried over sodium sulfate, and concentrated to afford the product as an oil. MS m/z 582.2 (M+1).

Synthesis of 3-(2-(2-(benzo[b]thiophen-3-yl)-9-isopropyl-9H-purin-6-ylamino)ethyl)-1H-indol-5-yl 6-(5-((3aS,4S,6aR)-2-oxohexahydro-1H-thieno[3,4-d]imidazol-4-yl)pentanamido)hexanoate To a solution of (+)-biotin (35 mg, 0.14 mmol) and Et₃N (36 mg, 0.35 mmol) in DMF (1 ml) was added HATU (90 mg, 0.24 mmol). The mixture was stirred for 10 min, and then was added to a solution of (3-(2-(2-(benzo[b]thiophen-3-yl)-9-isopropyl-9H-purin-6-ylamino)ethyl)-1H-indol-5-yl 6-aminohexanoate (b) (68 mg, 0.12 mmol) in DMF (1 ml). The reaction mixture was stirred for 16 hr at rt and then was concentrated. The residue was purified by reverse-phase HPLC (C₁₈ column, eluting with MeOH—H₂O 0.05% TFA) to afford the title compound as an off-white solid. Example 210 showed an EC₅₀ value in the % CD34+ assay of 2.1 μM.

Example 211

3-(2-(2-(benzo[b]thiophen-3-yl)-9-isopropyl-9H-purin-6-ylamino)ethyl)-1H-indol-5-yl 6-(tert-butoxycarbonylamino)hexanoate

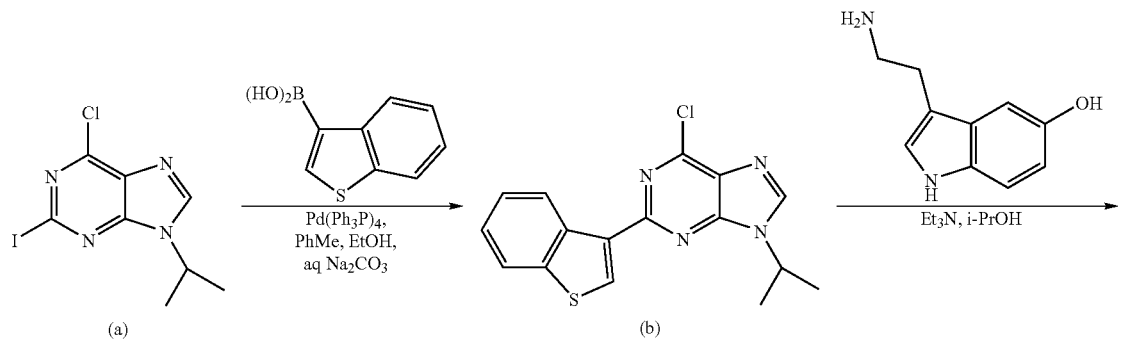

(a)　(b)

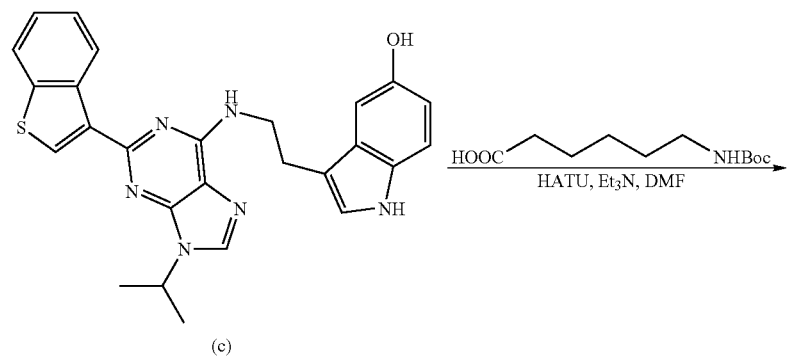

(c)

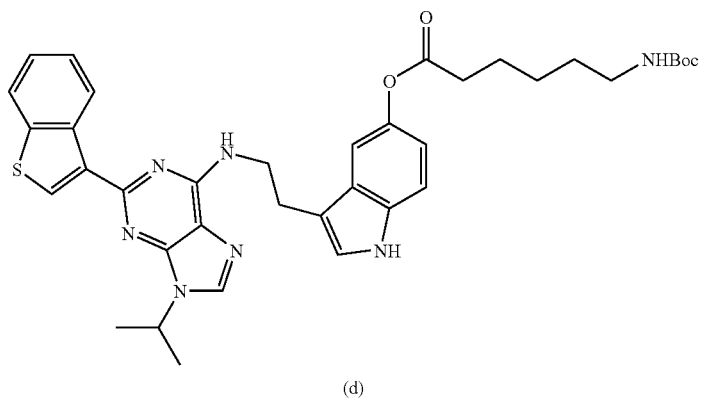

(d)

Synthesis of 2-(benzo[b]thiophen-3-yl)-6-chloro-9-isopropyl-9H-purine (b)

Following the procedure of Example 15d, 6-chloro-2-iodo-9-isopropyl-9H-purine (3.31 g, 0.0103 mol) was reacted with benzo[b]thiophen-3-ylboronic acid. The crude product was purified by silica gel chromatography (20 to 50% ethyl acetate in hexane) to afford the title compound as a solid. MS m/z 329.0 (M+1). $^1$H NMR (400 MHz, DMSO-$d_6$): δ=9.15 (d, 1H), 8.85 (s, 2H), 8.17 (d, 1H), 7.62 (t, 1H), 7.53 (t, 1H), 5.06 (m, 1H), 1.71 (d, 6H).

Synthesis of 3-(2-(2-(benzo[b]thiophen-3-yl)-9-isopropyl-9H-purin-6-ylamino)ethyl)-1H-indol-5-ol (c)

Following the procedure of Example 15e, 2-(benzo[b]thiophen-3-yl)-6-chloro-9-isopropyl-9H-purine (b) (80 mg, 0.243 mmol) was reacted with serotonin. The reaction mixture was concentrated, then aqueous sodium bicarbonate solution was added. The mixture was extracted with ethyl acetate. The organic fractions were combined, dried over sodium sulfate, and concentrated. The residue was purified by silica gel chromatography (0 to 5% MeOH in DCM eluant) to afford the title compound as an off-white solid. MS m/z 469.2 (M+1).

Synthesis of 3-(2-(2-(benzo[b]thiophen-3-yl)-9-isopropyl-9H-purin-6-ylamino)ethyl)-1H-indol-5-yl 6-(tert-butoxycarbonylamino)hexanoate (d)

To a solution of 3-(2-(2-(benzo[b]thiophen-3-yl)-9-isopropyl-9H-purin-6-ylamino)ethyl)-1H-indol-5-ol (55.5 mg, 0.119 mmol) and 6-(tert-butoxycarbonylamino)hexanoic acid (30 mg, 0.113 mmol) in DMF (3 ml) was added Et$_3$N (24 mg, 0.237 mmol) and HATU (90 mg, 0.237 mmol). The mixture was stirred at rt for 16 hr, and then was concentrated. Water was added and the reaction mixture was extracted with ethyl acetate. The organic fractions were combined, dried over sodium sulfate, and concentrated. The residue was purified by silica gel chromatography (0 to 5% MeOH in DCM eluant) to afford the title compound as an off-white solid.

By repeating the procedures described in the above examples, using appropriate starting materials, the following affinity probes, as identified in Table 2, are obtained:

TABLE 2

| Example Number | Structure | Physical Data $^1$H NMR and/or MS |
|---|---|---|
| 26 | 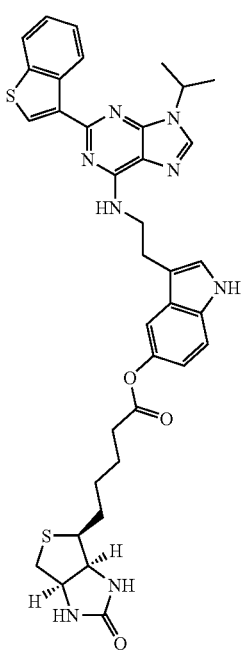 [SMILES: CC(C)n1cnc2c(NCCc3c[nH]c4ccc(OC(=O)CCCC[C@@H]5SC[C@@H]6NC(=O)N[C@@H]65)cc34)nc(-c3csc4ccccc34)nc21] | HRMS (EI) m/z 695.2585 (M + 1) |

TABLE 2-continued
| Example Number | Structure | Physical Data ¹H NMR and/or MS |
|---|---|---|
| 29 | 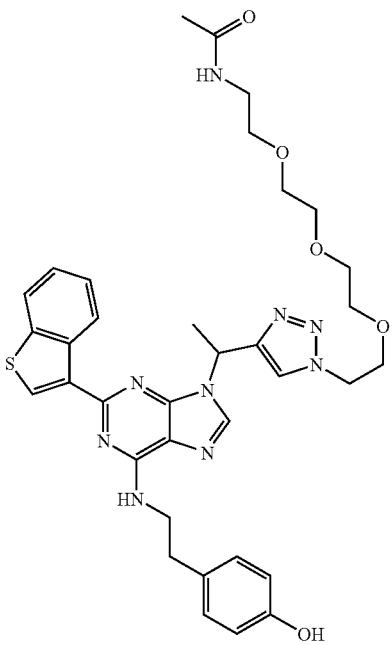 [SMILES: CC(=O)NCCOCCOCCOCCn1cc(C(C)n2cnc3c(NCCc4ccc(O)cc4)nc(-c4csc5ccccc45)nc32)nn1] | HRMS (EI) m/z 700.3027 (M + 1) |
| 209 | 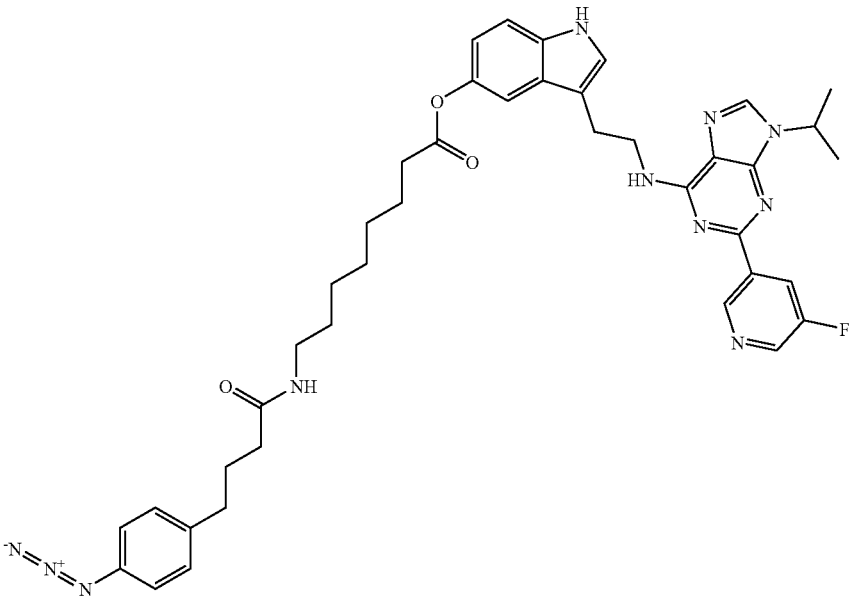 | MS m/z 760.4 (M +1) |
| 210 | 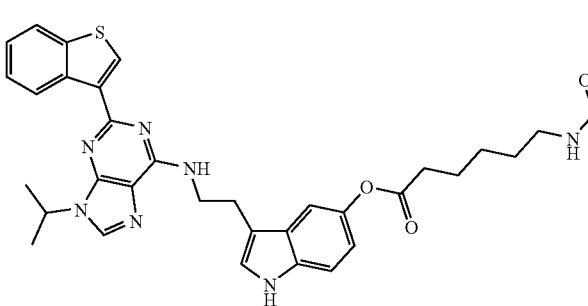 | 1H NMR (400 MHz, DMSO): δ = 10.95 (s, 1H), 9.17 (d, 1H), 8.54 (s, 1H), 8.34 (s, 1H), 8.06 (d, 1H), 7.94 (bs, 1H), 7.77 (t, 1H), 7.39-7.48 (m, 2H), 7.28-7.34 (m, 3H), 6.79 (dd, 1H), 6.42 (bs, 1H), 4.85-4.93 (m, 1H), 4.24-4.28 (m, 1H), 4.07-4.10 (m, 1H), 3.88-3.92 (m, 2H), 3.01-3.11 (m, 5H), 2.77 (dd, 1H), 2.53-2.57 (m, 1H), 2.00 (t, 2H), 1.63 (d, 6H), 1.23-1.60 (m, 12H); MS m/z 808.3 (M + 1) |

TABLE 2-continued
| Example Number | Structure | Physical Data $^1$H NMR and/or MS |
|---|---|---|
| 211 | 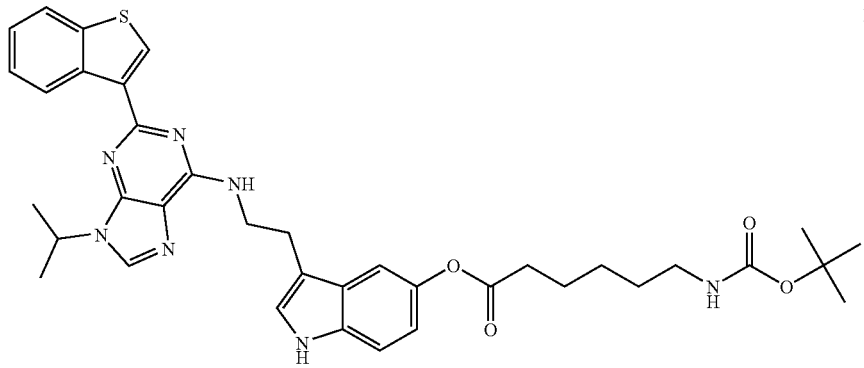 [SMILES: CC(C)n1cnc2c(NCCc3c[nH]c4ccc(OC(=O)CCCCCNC(=O)OC(C)(C)C)cc34)nc(-c3csc4ccccc34)nc21] | MS m/z 682.2 (M + 1). |
| 212 | 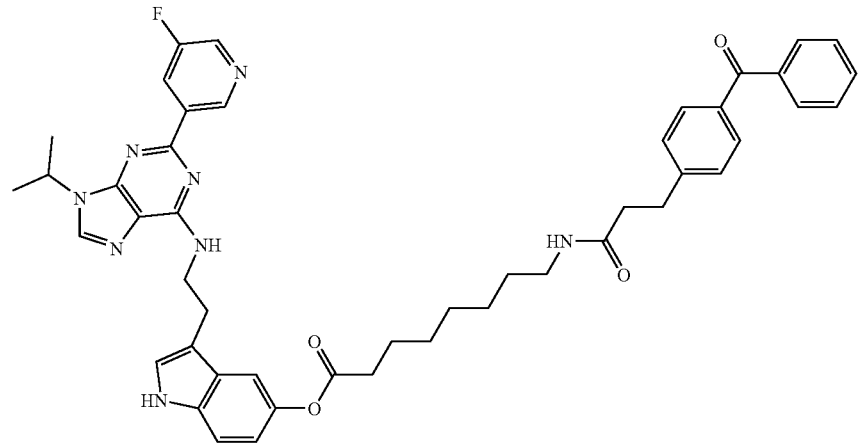 [SMILES: CC(C)n1cnc2c(NCCc3c[nH]c4ccc(OC(=O)CCCCCCCNC(=O)CCc5ccc(C(=O)c6ccccc6)cc5)cc34)nc(-c3cncc(F)c3)nc21] | MS m/z 809.4 (M + 1) |
| 213 | 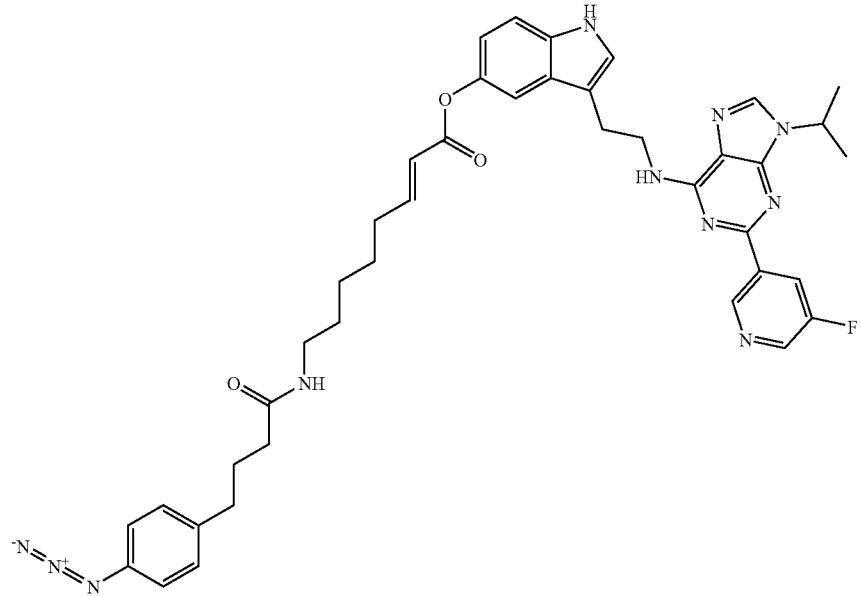 | MS m/z 758.4 (M + 1) |

TABLE 2-continued

| Example Number | Structure | Physical Data $^1$H NMR and/or MS |
|---|---|---|
| 214 | 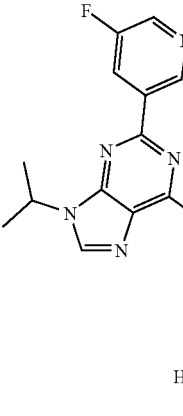 | MS m/z 807.4 (M + 1) |

Assays

The following assays are used to assess the activity of the compounds of the invention to facilitate hematopoietic stem cell (HSC) expansion.

Primary adult CD34+ human hematopoietic stem cells (HSCs) are cultured and screened to identify compounds of the invention that facilitate HSC expansion. The cells are analyzed for the presence of the desired phenotype (CD34 expression). Compounds of the invention promote HSC expansion in a dose dependent manner.

Culture Medium: StemSpan SFEM medium is serum-free medium (StemCell Technologies, Vancouver, BC) supplemented with the following human recombinant cytokines: thrombopoietin, interleukin-6, Flt-3 ligand, and stem cell factor (all from R&D Systems, Minneapolis, Minn.), each at a final concentration of 50 ng/mL, with vehicle (DMSO) or a compound of the invention.

Human Cell Culture: Fresh human leukophoresed G-CSF mobilized peripheral blood from normal donors, CD34+ cells from adult bone marrow and cryopreserved human cord blood CD34+ cells are purchased from AllCells (Berkeley, Calif.). Human CD34+ cells are enriched from leukophoresed G-CSF mobilized peripheral blood using magnetic cell sorting (MACS, Direct CD34 Progenitor Cell Isolation Kit, Miltenyi Biotec, Bergisch Gladbach, Germany) and cryopreserved. CD34+ cell purity, checked by flow Cytometry, is higher than 90%. After thawing, the cell viability tested by trypan blue exclusion is higher than 70%. The thawed cells are centrifuged and resuspended with StemSpan medium before being aliquoted for immediate culture. Cells are plated at $10^4$ cells/mL in a 384 well plate (Greiner Bio-One, Monroe, N.C.) with 50 µL of medium per well for 7 days. Every 7 days the cells are transferred to larger well plates and fresh medium is added to keep the cell density between $10^4$ and $5 \times 10^5$ cells/mL. Cells were cultured at 37° C. in 5% $CO_2$. For transplantation, cells were cultured in 75 cm² flasks before the cells were transplanted into mice. At a concentration of 1 micromolar, 4-(2-(2-(benzo[b]thiophen-3-yl)-9-isopropyl-9H-purin-6-ylamino)ethyl)phenol (compound 1, table 1; example 1), 4-(2-(2-(benzo[b]thiophen-3-yl)-9-sec-butyl-9H-purin-6-ylamino)ethyl)phenol (compound 2, table 1), and N-(2-(1H-indol-3-yl)ethyl)-2-(benzo[b]thiophen-3-yl)-9-isopropyl-9H-purin-6-amine (compound 9, table 1) each gives rise to a greater than 10-fold increase in the number of CD34+CD45RA− cells derived from 1000 mPB CD34+ HSCs after 21 days compared to vehicle. Compounds of the invention were assayed in a dose response format (1 nM to 1004) to determine the effective concentration that produced the desired effect in 50% of the cells ($EC_{50}$). Compounds of the invention increased the total number and/or percent of CD34+ cells with an EC50 of less than 10 µM. The results are shown in Table 1 and examples, supra.

Colony-Forming Units in Culture (CFU-C) Assay: Mononuclear cells at 1000 per mL for cord blood 5 week and mPB 3 week culture and 100 cells per mL for C δ 3 week and mPB 1 week culture were added to MethoCult SF H4436, serum-free methylcellulose medium containing methylcellulose in Iscove's MDM, bovine serum albumin, 2-mercaptoethanol, L-glutamine, human transferring (iron saturated), recombinant human insulin, and recombinant human cytokines: stem cell factor, GM-CSF, IL-3, IL-6, G-CSF, and erythropoietin (StemCell Technologies). The MethoCult is supplemented with the following human recombinant cytokines: thrombopoietin, and Flt-3 ligand (R&D Systems), each at a final concentration of 50 ng/mL. After stirring, the mixture is divided into three 35-mm dishes. The dishes are incubated for 14 days at 37° C. in a humidified atmosphere of 5% $CO_2$ in air. At the end of the incubation period, myeloid and erythroid colonies are counted under an inverted microscope at 40× magnification. CFU-C content of the expansion culture is calculated as follows: number of scored colonies per three dishes×total mononuclear cell number/input cell number. Up to one week, total mononuclear cells are determined by multiplying the number of cells per milliliter by the culture volume. From week 1 and on, the number of passages is also taken into account. Cultures treated with 4-(2-(2-(benzo[b]thiophen-3-yl)-9-isopropyl-9H-purin-6-ylamino)ethyl)phenol (compound 1, table 1; example 1) at a concentration of 1 micromolar, generated a greater than 10-fold increase in the number of colony forming cells after 21 days of culture of mPB CD34+ cells compared to vehicle. Using $1 \times 10^3$ CB CD34+ cells treated with 4-(2-(2-(benzo[b]thiophen-3-yl)-9-isopropyl-9H-purin-6-ylamino)ethyl)phenol (compound 1, table 1; example 1) at a concentration of 1 micromolar taken from the 5 week culture showed a >10-fold increase in colony forming units compared to control. Cells treated with a 4-(2-(2-(benzo[b]thiophen-3-yl)-9-isopropyl-9H-purin-6- ylamino)ethyl)phenol (compound 1, table 1; example 1) generated more mixed colonies associated with a >10-fold increase in erythrocyte colonies, a >10-fold increase in granulocyte/macrophage colonies, and a >10-fold increase in macrophage colonies. Cells treated with 4-(2-(2-(benzo[b]thiophen-3-yl)-9-isopropyl-9H-purin-6-ylamino)ethyl)phenol (compound 1, table 1; example 1) also give rise mixed granulocyte/erythrocyte/monocyte/macrophage colonies, which are not observed in colonies derived from untreated cultures.

Cobblestone area-forming cell (CAFC) assays: The FBMD-1 stromal cells are maintained in 25-cm$^2$ flasks and are trypsinized after ⅓ confluence. Since this non-transformed line ages, and therefore gradually loses its potential to support CAFC growth at late stages, all feeders are used below passage 20. For supporting CAFC growth in 96-well plates, 1×10$^3$ stromal cells are seeded per well. The cultures are maintained in Iscove's medium supplemented with 10% fetal calf serum (FCS), 2.5% horse serum (HS), 1% L-glutamine, 1% penicillin-streptomycin, and 1×10$^{-5}$ M hydrocortisone at 37° C. in a humidified atmosphere of 5% $CO_2$ in air. After stromal layers reach confluency, they are inoculated with CD34$^+$ HSCs that have been cultured for 5 days with vehicle or a compound of the invention. MNCs are added at 8 serial 1:3 dilutions (starting at 25,000 cells/well), with 10 wells for each cell dose. The dilutions with wells with at least one phase-dark hematopoietic clone (cobblestone area) of at least five cells beneath the stromal layer are determined at week 4. At a test concentration of 1 micromilar, 4-(2-(2-(benzo[b]thiophen-3-yl)-9-isopropyl-9H-purin-6-ylamino)ethyl)phenol (compound 1, table 1; example 1), stimulates a greater than 2-fold increase in the number of cobblestone area forming cells derived from mPB CD34$^+$ HSCs after 5 days of culture, compared with control cultures that are treated with DMSO alone.

Surface Antigen Analysis: The cells are washed with staining media (Hanks balanced salt solution containing FBS (2%) and EDTA (2 mM)) and stained (at 4° C. for 30 minutes) with indicated primary conjugated antibodies. The cells are washed in the previously described buffer and analyzed using a BD LSR II flow cytometer (Becton Dickinson, San Jose, Calif.). The cells are passed at a rate of up to 1000 cells/second using 488-nm argon and 633-nm HeNe laser beams as the light source for excitation. Emission of 10$^4$ cells is measured using logarithmic amplification and analyzed using FlowJo software (TreeStar Inc. Ashland, Oreg.). Cells stained with primary conjugated isotype control antibodies are used to determine background fluorescence.

Determination of CD34$^+$ cell subsets: The percentages of CD34$^+$ cell subsets are determined from aliquots of the cell culture. Cells were stained with APC anti-Thy1.1, PerCP anti-CD34, PECy7 anti CD45RA, FITC anti CD38, and PE anti-CD133 for determination of CD34$^+$Thy1.1$^+$, CD34$^+$CD45RA$^-$, CD34$^+$CD38$^-$, CD133$^+$CD38$^-$ and CD34$^+$CD133$^+$ cells. Antibodies to CD34, CD38, Thy1.1 and CD45RA were purchased from Becton Dickinson and antibodies to CD133 were purchased Miltenyi Biotec. FACS analysis results of these subsets are given as percentage of the total population. The absolute number of each population of cells in the culture is calculated from the total number of cells multiplied by the percentage of each population. Starting with CB CD34+ cell, after five weeks the total cell number in the cultures increased on average greater than 2-fold in the 4-(2-(2-(benzo[b]thiophen-3-yl)-9-isopropyl-9H-purin-6-ylamino)ethyl)phenol (compound 1, table 1; example 1) 1 micromolar treated cells compared to control cultures. More importantly, >50% of 4-(2-(2-(benzo[b]thiophen-3-yl)-9-isopropyl-9H-purin-6-ylamino)ethyl)phenol (compound 1, table 1; example 1) cultured cells were CD34$^+$ compared to <10% of vehicle cultured cells resulting in a greater than 10-fold expansion of CD34$^+$ cells compared to control and a greater than 10,000-fold expansion compared to input cells. In addition, the presence of 1 micromolar 4-(2-(2-(benzo[b]thiophen-3-yl)-9-isopropyl-9H-purin-6-ylamino)ethyl)phenol (compound 1, table 1; example 1) increased both the percentage and total numbers of the CD34$^+$ subpopulations, CD34$^+$CD45RA$^-$, CD34$^+$CD38$^-$, CD133$^+$CD38$^-$, and CD34$^+$CD133$^+$ resulting in a net expansion of greater than 30-fold for each subset.

Transplantation of human CD34$^+$ cells into NOD.CB17-Prkdc$^{scid}$ mice (NOD/SCID): To assess the in vivo repopulating capacity of CD34$^+$ cells and their cultured progeny, uncultured CD34$^+$ or the progenies of cultured CD34$^+$ cells after 4 days (mPB) or 21 days (CB) with vehicle or a test compound were injected intravenously via the retro-orbital route into sub-lethally irradiated (3.0 Gy) 8- to 10-week-old NOD/SCID (for mPB HSC experiments) or NOD/SCIDgc–/– (for CB HSC experiments) mice. To monitor engraftment blood was drawn weekly via the retro-orbital and treated with erythrocyte lysis solution (Qiagen, Valencia, Calif.) to remove red blood cells, washed with staining media, and analyzed by flow Cytometry. Engraftment was measured by detection of anti-human CD45$^+$ cells in the blood. The mice are sacrificed at 10 weeks post-transplantation; BM is collected from both femurs and tibiae. BM cells are washed in staining media and stained with anti-human antibodies. Following incubation, the suspension is treated with erythrocyte lysis solution (Qiagen, Valencia, Calif.) to remove red blood cells, washed with staining media, and analyzed by flow Cytometry, as described earlier. Both mPB and CB derived HSCs cultured with 4-(2-(2-(benzo[b]thiophen-3-yl)-9-isopropyl-9H-purin-6-ylamino)ethyl)phenol (compound 1, table 1; example 1) at a concentration of 1 micromolar give rise to a statistically significant increase in the percentage of human cells 10 weeks after engraftment.

Target Identification

To identify the mechanism whereby a compound of the invention expands HSCs in an undifferentiated state, a genome-wide transcriptional profiling of mPB-derived CD34$^+$ cells treated for 24 hours with example 1 and a less active analog (~20-fold) of example 1 (2-(benzo[b]thiophen-3-yl)-N-(3-(3,5-dimethyl-1H-pyrazol-4-yl)propyl)-9-isopropyl-9H-purin-6-amine). Of the >50,000 probe sets analyzed, only 5 genes were up-regulated greater than 3-fold upon treatment with Example 1 and most were also induced to some degree by the inactive analog. In addition, 5 genes were down-regulated by >70% upon treatment with 1 μM of Example 1. All were down-regulated in a dose dependent fashion and none were significantly affected by the inactive analog. The two genes that were the most highly repressed by treatment with Example 1 (cytochrome P450 1B1 [CYP1B1] and the aryl hydrocarbon receptor repressor [AHRR]) are transcriptionally regulated by the aryl hydrocarbon receptor (AHR). Therefore, compounds of the invention could be acting as an antagonist of AHR signaling.

Further, the ability of Example 1 to block 2,3,7,8-tetrachlorodibenzo-p-dioxin (TCDD, dioxin)-mediated CYP1B1 mRNA expression by qPCR in mPB-derived CD34$^+$ cells was determined. Treatment with TCDD (3 nM) caused a 4.5-fold increase in the level of CYP1B1 mRNA compared with the vehicle control (0.01% toluene). This increase was inhibited by Example 1 in a dose-dependent manner indicating that compounds of the invention can antagonize AHR signaling. To determine the effects of Example 1 in AHR transcription the ability of Example 1 to inhibit a dioxin-induced AHR dependent luciferase reporter gene assay was tested. Inclusion of Example 1 (1 μM) completely abolished dioxin-induced AHR dependent transcription when used on cells expressing human AHR. Titration of Example 1 revealed an $EC_{50}$ of 127 nM, demonstrating that Example 1 is a potent AHR antagonist. Interestingly, Example 1 only weakly inhibited dioxin induced transcription in murine cells and had no activity on rat cells, suggesting that Example 1 preferentially inhibits human AHR. This correlates with a lack of activity of Example 1 on murine HSC, and can explain the species selectivity of Example 1. Finally, Example 1 had only weak agonist activity on murine or rat cells, and failed to induce AHR dependent transcription in human cells.

To further explore the role of AHR signaling in HSCs two other AHR antagonists (alpha-naphthoflavone and CH-223191) were tested. Both compounds lead to dose dependent increases in the number of $CD34^+$ cells when cultured with mPB-derived $CD34^+$ cell for 7 days: inclusion of 1 μM CH223191 afforded a 2.2-fold expansion of $CD34^+$ cells; 0.75 μM α-naphthoflavone afforded a 1.9-fold expansion of $CD34^+$ cells while 0.75 μM Example 1 afforded a 3.4-fold expansion of total $CD34^+$ cells. To show a direct role for the AHR in Example 1 induced HSC expansion, human CB-derived $CD34^+$ HSCs were treated with lentiviral particles containing a shRNA-targeting AHR that co-expressed GFP or control virus. Forty-eight hours following transduction, $CD34^+GFP^+$ cells were purified by cell sorting and the levels of AHR were determined by qPCR. Both AHR targeting shRNAs led to decreases in AHR expression following transduction (81% with shill and 51% with sh242). These decreases were not seen in cells lacking GFP or in cells transduced with control virus. CB-derived $CD34^+$ cells with decreased AHR expression displayed a phenotype similar to Example 1 treated cells with sustained expression of $CD34^+$. These data show that inhibition of AHR activity by a compound of the invention is sufficient to promote ex-vivo expansion of HSC.

Method of Expanding HSCs from Human Neonatal Umbilical Cord Blood

The culture medium used is StemSpan SFEM (StemCell Technologies, Cat. #09650) supplemented with the following recombinant human cytokines: TPO, IL6, Flt3 ligand, and SCF each at a final concentration of 50 ng/mL. The culture media is prepared fresh the day of use.

Compound dilution into media: a 10,000× concentrate of a compound of the invention is used for the dilutions. The addition of compound into the culture media occurs in two steps. The first step is a 1:100 dilution (10 μL of 10,000× concentrate into 990 μL of complete culture media (containing cytokines) in a 1.5 mL effendorf tube [USA Scientific, Cat #1615-5500]) to generate a 100× solution of compound in the culture media. The second step is a 1:100 dilution into the culture media that will be used to initiate the cell culture. The volume of the culture is variable depending on the input number of cord blood (CB) $CD34^+$ cells. For example, $1 \times 10^6$ CB $CD34^+$ cells are seeded into 20 mL of media ($5 \times 10^4$ cells/mL). In this case, 200 μL of the 100× Example 1 solution is added to the 20 mL of media in a 50 mL conical tube (Becton Dickinson, Cat #352098) to reach the final concentration (see Table 3).

Cell culture initiation: purified human CB $CD34^+$ cells are used for the ex vivo expansion experiments. After thawing, the cell viability, tested by trypan blue exclusion, is higher than 50%. The thawed cells are diluted 5-fold with culture media (no cytokines or compounds of the invention such as Example 1) and centrifuged at 300 g at 25° C. for 8 minutes. After aspirating the supernatant, the pellet is resuspended with the appropriate volume of culture medium ($5 \times 10^4$ cells/mL, Table 3) before being injected (22 gauge needle, Air-Tite products; 20 mL syringe, BD cat #309661) into AFC bags (Table 5) for immediate culture. Cells are cultured at 37° C. in 5% $CO_2$.

Addition of media to the cell culture: for media volumes up to 80 mL the procedure above (compound dilution into media) is used. For media volumes larger than 80 mL the first 1:100 dilution is carried out in 10 mL conical tubes (Corning, Cat #430052, Table 4).

The second step is a 1:100 dilution into the culture media, in sterile containers, (BD Falcon, Cat #354015) that is added to the AFC bag (22 gauge needle, Air-Tite products; 60 mL syringe, BD cat #309653).

TABLE 3

Example 1 dilutions for starting cord blood derived CD34+ cell expansion

| Number of cord blood derived CD34+ cells ($\times 10^6$) | Starting culture volume (mL) | volume of 100x Example 1 (μL) needed | volume of 100x Example 1 to prepare (mL) | volume of 10,000x Example 1 needed (μL) |
|---|---|---|---|---|
| 0.25 | 5 | 50 | 1 | 10 |
| 0.50 | 10 | 100 | 1 | 10 |
| 0.75 | 15 | 150 | 1 | 10 |
| 1.00 | 20 | 200 | 1 | 10 |
| 1.25 | 25 | 250 | 1 | 10 |
| 1.50 | 30 | 300 | 1 | 10 |
| 1.75 | 35 | 350 | 1 | 10 |
| 2.00 | 40 | 400 | 1 | 10 |
| 2.50 | 50 | 500 | 1 | 10 |
| 3.00 | 60 | 600 | 1 | 10 |
| 4.00 | 80 | 800 | 1 | 10 |

TABLE 4

Example 1 dilutions for adding media to the cord blood derived CD34+ cell expansion

| Volume of media to add (mL) | volume of 100x Example 1 (μL) needed | volume of 100x Example 1 to prepare (mL) | volume of 10,000x Example 1 needed (μL) |
|---|---|---|---|
| 10.00 | 100 | 1 | 10 |
| 20.00 | 200 | 1 | 10 |
| 30.00 | 300 | 1 | 10 |
| 40.00 | 400 | 1 | 10 |
| 50.00 | 500 | 1 | 10 |
| 60.00 | 600 | 1 | 10 |
| 70.00 | 700 | 1 | 10 |
| 80.00 | 800 | 1 | 10 |
| 100.00 | 1,000 | 5 | 50 |
| 120.00 | 1,200 | 5 | 50 |
| 160.00 | 1,600 | 5 | 50 |
| 250.00 | 2,500 | 5 | 50 |
| 500.00 | 5,000 | 10 | 100 |
| 750.00 | 7,500 | 10 | 100 |
| 1,000.00 | 10,000 | 10 | 100 |

TABLE 5

Volume restrictions for American Fluoroseal Corporation bags.

| AFC bag catalog number | Volume for optimal expansion (mL) | Maximum volume of the bag (mL) |
|---|---|---|
| 1PF-0007 | 7 | 7 |
| 2PF-0032 | 32 | 32 |
| 2PF-0072 | 71 | 130 |

TABLE 5-continued

Volume restrictions for American Fluoroseal Corporation bags.

| AFC bag catalog number | Volume for optimal expansion (mL) | Maximum volume of the bag (mL) |
|---|---|---|
| 2PF-0118 | 118 | 245 |
| 2PF-0197 | 179 | 580 |
| 2PF-0225 | 225 | 665 |
| 2PF-0270 | 270 | 960 |
| 2PF-750C | 750 | |

The same protocol can be used starting from mobilized peripheral blood cells from a patient for autologous graft transplantation.

A composition comprising a population of cells with expanded HSCs appropriate for intravenous administration as an infusion can also be prepared. To prepare cells for infusion, cultured cells are pelletted by centrifugation for 10 minutes at 300 g and resuspended in infusion buffer consisting of 5% HSA (Baxter) at a concentration of between $10^6$ to $10^8$ cells/ml.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A method of increasing the number of human stem and progenitor cells; said method comprising contacting the stem cells with an agent capable of antagonizing the activity and/or expression of aryl hydrocarbon receptor and/or a down-stream effector of aryl hydrocarbon receptor pathway, wherein said agent is a compound of the formula:

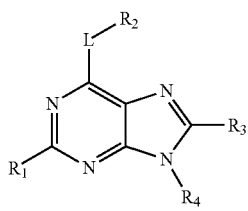

1a in which:
L is selected from —NH(CH$_2$)$_{2-3}$—;
R$_1$ is selected from thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-4-yl, 1H-imidazol-1-yl, pyrazin-2-yl, pyridin-3-yl, pyridazin-4-yl, 1H-pyrrol-2-yl and thiazol-5-yl; wherein
said thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridiny-2-yl, pyridin-4-yl, 1H-imidazol-1-yl, pyrazin-2-yl, pyridiny-3-yl, pyridazin-4-yl, 1H-pyrrol-2-yl, or thiazol-5-yl of R$_1$ can be optionally substituted by 1 to 3 radicals independently selected from cyano, C$_{1-4}$alkyl, C$_{1-4}$alkoxy, halo, halo-substituted-C$_{1-4}$alkyl, —S(O)$_{0-2}$R$_{8a}$ and —C(O)OR$_{8a}$; wherein R$_{8a}$ is selected from hydrogen and C$_{1-4}$alkyl;
R$_2$ is selected from phenyl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl; wherein
the phenyl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, or 2-oxo-2,3-dihydro-1H-benzo[d]imidazol-5-yl of R$_2$ is optionally substituted with hydroxy, methoxy, methyl, halo, and amino;
R$_3$ is selected from hydrogen; and
R$_4$ is selected from isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl;
or a salt thereof.
2. The method of claim 1 in which the method is carried out in vitro or ex vivo.
3. The method of claim 2, in which the stem cells are derived from bone marrow.
4. The method of claim 2, in which the stem cells are derived from umbilical cord blood.
5. The methods of claim 3 or 4 in which the stem cells are hematopoietic stem cells.
6. A method of expanding human hematopoietic stem cells, comprising (a) providing a starting cell population comprising human hematopoietic stem cells and
(b) culturing said starting cell population ex vivo in presence of an agent capable of antagonizing the activity and/or expression of aryl hydrocarbon receptor and/or a down-stream effector of aryl hydrocarbon receptor pathway, under suitable conditions for expanding hematopoietic stem cells, wherein said agent is a compound of the Formula 1a:

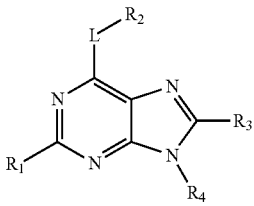

1a in which:
L is selected from —NH(CH$_2$)$_{2-3}$—;
R$_1$ is selected from thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-4-yl, 1H-imidazol-1-yl, pyrazin-2-yl, pyridin-3-yl, pyridazin-4-yl, 1H-pyrrol-2-yl and thiazol-5-yl; wherein
said thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridiny-2-yl, pyridin-4-yl, 1H-imidazol-1-yl, pyrazin-2-yl, pyridiny-3-yl, pyridazin-4-yl, 1H-pyrrol-2-yl or thiazol-5-yl of R$_1$ can be optionally substituted by 1 to 3 radicals independently selected from cyano, C$_{1-4}$alkyl, C$_{1-4}$alkoxy, halo, halo-substituted-C$_{1-4}$alkyl, —S(O)$_{0-2}$R$_{8a}$ and —C(O)OR$_{8a}$; wherein R$_{8a}$ is selected from hydrogen and C$_{1-4}$alkyl;
R$_2$ is selected from phenyl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, and 2-oxo-2,3-dihydro-1H-benzo[d]imidazol-5-yl; wherein
the phenyl, 1H-indol-3-yl, thiophen-3-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, or 2-oxo-2,3-dihydro-1H-benzo[d]imidazol-5-yl of R$_2$ is optionally substituted with hydroxy, methoxy, methyl, halo, and amino;
R$_3$ is selected from hydrogen; and
R$_4$ is selected from isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, and nonan-2-yl;
or a salt thereof.
7. The method of claim 6, wherein a down-stream effector of aryl hydrocarbon receptor pathway is selected from Cyp1B1, Cyp1A1, Beta catenin, AHRR, STAT5 and STAT1.
8. The method of claim 6, wherein said starting cell population is enriched in CD34+ cells.
9. The method of claim 6, wherein said starting cell population is derived from umbilical cord blood cells.
10. The method of claim 6, wherein said starting cell population is derived from one or two cord blood units, preferably one cord blood unit.

11. The method of claim 6, wherein said starting cell population is derived from mobilized peripheral blood cells.

12. The method of claim 11, wherein the mobilized peripheral blood cells are obtained from a single human subject.

13. The method of claim 6, wherein said starting cell population essentially consists of CD34+cells purified from one or two cord blood units, preferably one cord blood unit.

14. The method of claim 6, wherein said starting cell population essentially consists of CD34+cells purified from one or two cord blood units using affinity chromatography columns or magnetic beads comprising CD34 antigen binding antibody fragments.

15. The method of claim 6, wherein said conditions for hematopoietic stem cell expansion include culturing said starting cell population in presence of a sufficient amount of IL6, Flt3-L, TPO and SCF and said compound-of claim 6.

16. The method of claim 6, wherein said compound is administered in the cell culture medium at a concentration between 1 pM and 100 µM.

17. The method of claim 6, wherein said starting cell population essentially consists of CD34+ cells purified from one or two cord blood units, preferably one cord blood unit, and said starting cell population is cultured in presence of said compound from about 3 days to about 90 days.

18. The method of claim 6, wherein said starting cell population is cultured in presence of said compound during a time sufficient for a 10 to 50000 fold expansion of CD34+ cells.

19. The method of claim 6, in which L is —NH(CH$_2$)$_2$—.

20. The method of claim 6, wherein the compound is selected from:
- 4-(2-(2-(benzo[b]thiophen-3-yl)-9-isopropyl-9H-purin-6-ylamino)ethyl)phenol;
- 4-(2-(2-(benzo[b]thiophen-3-yl)-9-sec-butyl-9H-purin-6-ylamino)ethyl)phenol;
- 4-(9-benzhydryl-2-(benzo[b]thiophen-3-yl)-9H-purin-6-ylamino)ethyl)phenol;
- 4-(2-(2-(benzo[b]thiophen-3-yl)-9-(tetrahydro-2H-pyran-3-yl)-9H-purin-6-ylamino)ethyl)phenol;
- 4-(2-(9-isopropyl-2-(thiophen-2-yl)-9H-purin-6-ylamino)ethyl)phenol;
- 4-(2-(2-(benzo[b]thiophen-3-yl)-9-(4-(trifluoromethyl)benzyl)-9H-purin-6-ylamino)ethyl)phenol;
- 4-(2-(2-(benzo[b]thiophen-3-yl)-9-isobutyl-9H-purin-6-ylamino)ethyl)phenol;
- 4-(2-(2-(benzo[b]thiophen-3-yl)-9-methyl-9H-purin-6-ylamino)ethyl)phenol;
- 4-(2-(2-(benzo[b]thiophen-3-yl)-9-(4-methylbenzyl)-9H-purin-6-ylamino)ethyl)phenol;
- N-(2-(1H-indol-3-yl)ethyl)-2-(benzo[b]thiophen-3-yl)-9-isopropyl-9H-purin-6-amine;
- 2-(benzo[b]thiophen-3-yl)-9-isopropyl-N-(2-(thiophen-3-yl)ethyl)-9H-purin-6-amine;
- 3-(2-(2-(benzo[b]thiophen-3-yl)-9-isopropyl-9H-purin-6-ylamino)ethyl)phenol;
- 2-(benzo[b]thiophen-3-yl)-N-(4-fluorophenethyl)-9-isopropyl-9H-purin-6-amine;
- N-(4-aminophenethyl)-2-(benzo[b]thiophen-3-yl)-9-isopropyl-9H-purin-6-amine;
- 4-(2-(9-isopropyl-2-(pyrimidin-5-yl)-9H-purin-6-ylamino)ethyl)phenol;
- 4-(2-(9-isopropyl-2-(pyridin-3-yl)-9H-purin-6-ylamino)ethyl)phenol;
- 4-(2-(9-isopropyl-2-(thiophen-3-yl)-9H-purin-6-ylamino)ethyl)phenol;
- 4-(2-(2-(furan-3-yl)-9-isopropyl-9H-purin-6-ylamino)ethyl)phenol;
- 2-(benzo[b]thiophen-3-yl)-N-(4-fluorophenethyl)-9-phenyl-9H-purin-6-amine;
- 4-(2-(2-(benzo[b]thiophen-3-yl)-9-(nonan-2-yl)-9H-purin-6-ylamino)ethyl)phenol;
- N-(2-(1H-indol-3-yl)ethyl)-2-(benzo[b]thiophen-3-yl)-9-sec-butyl-9H-purin-6-amine;
- 4-(2-(9-isopropyl-2-(pyridin-4-yl)-9H-purin-6-ylamino)ethyl)phenol;
- ethyl 5-(6-(4-hydroxyphenethylamino)-9-isopropyl-9H-purin-2-yl)nicotinate;
- 4-(2-((9-isopropyl-2-(5-methoxypyridin-3-yl)-9H-purin-6-yl)amino)ethyl)phenol;
- 4-(2-(2-(6-fluoropyridin-3-yl)-9-isopropyl-9H-purin-6-ylamino)ethyl)phenol;
- 4-(2-(9-isopropyl-2-(4-methylpyridin-3-yl)-9H-purin-6-ylamino)ethyl)phenol;
- 5-(6-(4-hydroxyphenethylamino)-9-isopropyl-9H-purin-2-yl)nicotinonitrile;
- 4-(2-(2-(1H-imidazol-1-yl)-9-isopropyl-9H-purin-6-ylamino)ethyl)phenol;
- 4-(2-(9-isopropyl-2-(pyridazin-4-yl)-9H-purin-6-ylamino)ethyl)phenol;
- 4-(2-(9-isopropyl-2-(pyrazin-2-yl)-9H-purin-6-ylamino)ethyl)phenol;
- 4-(2-(9-isopropyl-2-(pyridin-2-yl)-9H-purin-6-ylamino)ethyl)phenol;
- 4-(2-(9-isopropyl-2-(5-(methylsulfonyl)pyridin-3-yl)-9H-purin-6-ylamino)ethyl)phenol;
- 4-(2-(9-isopropyl-2-(5-methylpyridin-3-yl)-9H-purin-6-ylamino)ethyl)phenol;
- 4-(2-(2-(4-chloropyridin-3-yl)-9-isopropyl-9H-purin-6-ylamino)ethyl)phenol;
- 4-(2-(2-(5-fluoropyridin-3-yl)-9-isopropyl-9H-purin-6-ylamino)ethyl)phenol;
- 4-(2-49-isopropyl-2-(4-methylthiophen-3-yl)-9H-purin-6-yl)amino)ethyl)phenol;
- 4-(2-(9-isopropyl-2-(pyridin-3-yl)-9H-purin-6-ylamino)ethyl)-2-methoxyphenol;
- N-[2-(6-methoxy-1H-indol-3-yl)ethyl]-9-(propan-2-yl)-2-(pyridin-3-yl)-9H-purin-6-amine;
- N-[2-(5-methyl-1H-indol-3-yl)ethyl]-9-(propan-2-yl)-2-(pyridin-3-yl)-9H-purin-6-amine;
- 1-(2-{[9-(propan-2-yl)-2-(pyridin-3-yl)-9H-purin-6-yl]amino}ethyl)imidazolidin-2-one;
- N-(2-{[9-(propan-2-yl)-2-(pyridin-3-yl)-9H-purin-6-yl]amino}ethyl)pyridin-2-amine;
- 9-(propan-2-yl)-N-[3-(1H-pyrazol-4-yl)propyl]-2-(pyridin-3-yl)-9H-purin-6-amine;
- N-{2-[(3-methyl-1H-1,2,4-triazol-5-yl)sulfanyl]ethyl}-9-(propan-2-yl)-2-(pyridin-3-yl)-9H-purin-6-amine;
- 1-(2-{[2-(1-benzothiophen-3-yl)-9-(propan-2-yl)-9H-purin-6-yl]amino}ethyl)imidazolidin-2-one;
- N-[2-(5-amino-1H-1,2,4-triazol-3-yl)ethyl]-2-(1-benzothiophen-3-yl)-9-(propan-2-yl)-9H-purin-6-amine;
- N-(2-{[2-(1-benzothiophen-3-yl)-9-(propan-2-yl)-9H-purin-6-yl]amino}ethyl)pyridin-2-amine;
- 2-(1-benzothiophen-3-yl)-9-(propan-2-yl)-N-[3-(1H-pyrazol-4-yl)propyl]-9H-purin-6-amine;
- 2-(1-benzothiophen-3-yl)-N-[3-(3,5-dimethyl-1H-pyrazol-4-yl)propyl]-9-(propan-2-yl)-9H-purin-6-amine;
- (2-{[2-(1-benzothiophen-3-yl)-9-(propan-2-yl)-9H-purin-6-yl]amino}ethyl)urea;
- N-[2-(1H-indol-3-yl)ethyl]-9-(propan-2-yl)-2-(pyridin-3-yl)-9H-purin-6-amine;
- N-(4-(2-(9-isopropyl-2-(pyridin-3-yl)-9H-purin-6-ylamino)ethyl)phenyl)methane-sulfonamide;

4-(2-(2-(pyridin-3-yl)-9-(tetrahydrofuran-3-yl)-9H-purin-6-ylamino)ethyl)phenol;
4-(2-(9-isopropyl-2-(pyridin-3-yl)-9H-purin-6-ylamino)propyl)phenol;
4-(2-(9-(oxetan-3-yl)-2-(pyridin-3-yl)-9H-purin-6-ylamino)ethyl)phenol;
N-(2-(1H-indazol-3-yl)ethyl)-9-isopropyl-2-(pyridin-3-yl)-9H-purin-6-amine;
4-(2-(9-(1-hydroxypropan-2-yl)-2-(pyridin-3-yl)-9H-purin-6-ylamino)ethyl)phenol;
4-(2-(9-isopropyl-2-(pyridin-3-yl)-9H-purin-6-ylamino)ethyl)phenyl sulfamate;
4-(2-(2-(2-fluoropyridin-3-yl)-9-isopropyl-9H-purin-6-ylamino)ethyl)phenol;
4-(2-(9-isopropyl-2-(1-methyl-1H-pyrrol-2-yl)-9H-purin-6-ylamino)ethyl)phenol;
4-(2-(9-isopropyl-2-(thiazol-5-yl)-9H-purin-6-ylamino)ethyl)phenol;
4-(2-(2-(1H-benzo[d]imidazol-1-yl)-9-isopropyl-9H-purin-6-ylamino)ethyl)phenol;
4-(2-(2-(2,4-dimethyl-1H-imidazol-1-yl)-9-isopropyl-9H-purin-6-ylamino)ethyl)phenol;
4-(2-(9-isopropyl-2-(2-methyl-1H-imidazol-1-yl)-9H-purin-6-ylamino)ethyl)phenol;
5-(9-sec-butyl-6-(4-hydroxy-3-methylphenethylamino)-9H-purin-2-yl)nicotinonitrile;
N-(2-(1H-pyrrolo[2,3-b]pyridin-5-yl)ethyl)-9-isopropyl-2-(pyridin-3-yl)-9H-purin-6-amine;
9-isopropyl-N-(2-(5-methyl-1H-pyrazol-3-yl)ethyl)-2-(pyridin-3-yl)-9H-purin-6-amine;
4-(2-(2-(5-fluoropyridin-3-yl)-9-(oxetan-3-yl)-9H-purin-6-ylamino)ethyl)phenol;
4-(2-(2-(5-chloropyridin-3-yl)-9-isopropyl-9H-purin-6-ylamino)ethyl)phenol;
4-(2-(9-isopropyl-2-(5-(trifluoromethyl)pyridin-3-yl)-9H-purin-6-ylamino)ethyl)phenol;
5-(6-(2-(1H-indol-3-yl)ethylamino)-9-sec-butyl-9H-purin-2-yl)nicotinonitrile;
N-(2-(1H-indol-3-yl)ethyl)-9-sec-butyl-2-(5-methylpyridin-3-yl)-9H-purin-6-amine;
(R)-N-(2-(1H-indol-3-yl)ethyl)-9-sec-butyl-2-(5-fluoropyridin-3-yl)-9H-purin-6-amine;
(S)-N-(2-(1H-indol-3-yl)ethyl)-9-sec-butyl-2-(5-fluoropyridin-3-yl)-9H-purin-6-amine;
N-(2-(1H-indol-3-yl)ethyl)-9-sec-butyl-2-(5-fluoropyridin-3-yl)-9H-purin-6-amine;
(R)-N-(2-(1H-indol-3-yl)ethyl)-9-sec-butyl-2-(5-methylpyridin-3-yl)-9H-purin-6-amine;
(S)-N-(2-(1H-indol-3-yl)ethyl)-9-sec-butyl-2-(5-methylpyridin-3-yl)-9H-purin-6-amine;
5-(6-(4-hydroxyphenethylamino)-9-(oxetan-3-yl)-9H-purin-2-yl)nicotinonitrile;
(R)-4-(2-(2-(5-fluoropyridin-3-yl)-9-(tetrahydrofuran-3-yl)-9H-purin-6-ylamino)ethyl)phenol;
4-(2-(9-isopropyl-2-(pyridin-3-yl)-9H-purin-6-ylamino)ethyl)-3-methylphenol;
5-(6-(4-hydroxyphenethylamino)-9-isopropyl-9H-purin-2-yl)picolinonitrile;
3-(6-(4-hydroxyphenethylamino)-9-isopropyl-9H-purin-2-yl)isonicotinonitrile;
3-(6-(4-hydroxyphenethylamino)-9-isopropyl-9H-purin-2-yl)picolinonitrile;
4-(2-(9-isopropyl-2-(6-methylpyridin-3-yl)-9H-purin-6-ylamino)ethyl)phenol;
4-(2-(9-isopropyl-2-(isoquinolin-4-yl)-9H-purin-6-ylamino)ethyl)phenol;
2-chloro-4-(2-(9-isopropyl-2-(pyridin-3-yl)-9H-purin-6-ylamino)ethyl)phenol;
3-fluoro-4-(2-(9-isopropyl-2-(pyridin-3-yl)-9H-purin-6-ylamino)ethyl)phenol;
N-(2-(5-chloro-1H-indol-3-yl)ethyl)-9-isopropyl-2-(pyridin-3-yl)-9H-purin-6-amine;
N-(2-(5-fluoro-1H-indol-3-yl)ethyl)-9-isopropyl-2-(pyridin-3-yl)-9H-purin-6-amine;
4-(2-(9-isopropyl-2-(pyridin-3-yl)-9H-purin-6-ylamino)ethyl)-2-methylphenol;
4-(2-(2-(benzo[b]thiophen-3-yl)-9-(oxetan-3-yl)-9H-purin-6-ylamino)ethyl)phenol;
(S)-4-(2-(2-(benzo[b]thiophen-3-yl)-9-(tetrahydrofuran-3-yl)-9H-purin-6-ylamino)ethyl)phenol;
(R)-4-(2-(2-(benzo[b]thiophen-3-yl)-9-(tetrahydrofuran-3-yl)-9H-purin-6-ylamino)ethyl)phenol;
2-(6-(2-(1H-indol-3-yl)ethylamino)-2-(5-fluoropyridin-3-yl)-9H-purin-9-yl)propan-1-ol;
(R)-2-(6-(2-(1H-indol-3-yl)ethylamino)-2-(5-fluoropyridin-3-yl)-9H-purin-9-yl)propan-1-ol;
(S)-2-(6-(2-(1H-indol-3-yl)ethylamino)-2-(5-fluoropyridin-3-yl)-9H-purin-9-yl)propan-1-ol;
(R)-N-(2-(1H-indol-3-yl)ethyl)-2-(5-fluoropyridin-3-yl)-9-(tetrahydrofuran-3-yl)-9H-purin-6-amine;
4-(2-(2-(1H-imidazo[4,5-b]pyridin-1-yl)-9-isopropyl-9H-purin-6-ylamino)ethyl)phenol;
4-(2-(2-(4,5-dimethyl-1H-imidazol-1-yl)-9-isopropyl-9H-purin-6-ylamino)ethyl)phenol;
2-(5-fluoropyridin-3-yl)-9-isopropyl-N-(2-(pyridin-3-yl)ethyl)-9H-purin-6-amine;
4-(2-(2-(5-fluoropyridin-3-yl)-9-isopropyl-9H-purin-6-ylamino)-1-hydroxyethyl)phenol;
2-(5-fluoropyridin-3-yl)-9-isopropyl-N-(2-(6-methoxy-1H-indol-3-yl)ethyl)-9H-purin-6-amine;
N-(2-(1H-indol-3-yl)ethyl)-2-(5-fluoropyridin-3-yl)-9-isopropyl-9H-purin-6-amine;
2-(5-fluoropyridin-3-yl)-9-isopropyl-N-(2-(5-methoxy-1H-indol-3-yl)ethyl)-9H-purin-6-amine;
N-(2-(1H-indol-3-yl)ethyl)-2-(5-fluoropyridin-3-yl)-9-(prop-1-en-2-yl)-9H-purin-6-amine;
5-(2-(2-(5-fluoropyridin-3-yl)-9-isopropyl-9H-purin-6-ylamino)ethyl)pyridin-2-ol;
N-(2-(1H-pyrrolo[2,3-b]pyridin-3-yl)ethyl)-2-(5-fluoropyridin-3-yl)-9-isopropyl-9H-purin-6-amine;
N-(2-(6-(2-(diethylamino)ethoxy)-1H-indol-3-yl)ethyl)-2-(5-fluoropyridin-3-yl)-9-isopropyl-9H-purin-6-amine;
N-(2-(1H-indol-3-yl)ethyl)-9-sec-butyl-2-(2-methyl-1H-imidazol-1-yl)-9H-purin-6-amine;
4-(2-(2-(2-ethyl-1H-imidazol-1-yl)-9-isopropyl-9H-purin-6-ylamino)ethyl)phenol;
4-(2-(9-isopropyl-2-(2-propyl-1H-imidazol-1-yl)-9H-purin-6-ylamino)ethyl)phenol;
3-(2-(2-(5-fluoropyridin-3-yl)-9-isopropyl-9H-purin-6-ylamino)ethyl)-1H-indol-6-ol;
N-(2-(1H-indol-3-yl)ethyl)-9-isopropyl-2-(5-methylpyridin-3-yl)-9H-purin-6-amine;
N-(2-(1H-indol-3-yl)ethyl)-9-isopropyl-2-(2-methyl-1H-imidazol-1-yl)-9H-purin-6-amine;
2-(5-fluoropyridin-3-yl)-9-isopropyl-N-(2-(7-methyl-1H-indol-3-yl)ethyl)-9H-purin-6-amine;
N-(2-(1H-indol-3-yl)ethyl)-2-(5-fluoropyridin-3-yl)-9-(oxetan-3-yl)-9H-purin-6-amine;
N-(2-(1H-indol-3-yl)ethyl)-2-(5-methylpyridin-3-yl)-9-(oxetan-3-yl)-9H-purin-6-amine;
N-(2-(6-fluoro-1H-indol-3-yl)ethyl)-2-(5-fluoropyridin-3-yl)-9-isopropyl-9H-purin-6-amine;

2-(5-fluoropyridin-3-yl)-9-isopropyl-N-(2-(6-methyl-1H-indol-3-yl)ethyl)-9H-purin-6-amine;

2-(5-fluoropyridin-3-yl)-9-isopropyl-N-(2-(2-methyl-1H-indol-3-yl)ethyl)-9H-purin-6-amine;

N-(2-(4-fluoro-1H-indol-3-yl)ethyl)-2-(5-fluoropyridin-3-yl)-9-isopropyl-9H-purin-6-amine;

N-(2-(7-fluoro-1H-indol-3-yl)ethyl)-2-(5-fluoropyridin-3-yl)-9-isopropyl-9H-purin-6-amine;

2-(5-fluoropyridin-3-yl)-9-isopropyl-N-(2-(4-methyl-1H-indol-3-yl)ethyl)-9H-purin-6-amine;

N-(2-(1H-pyrrolo[2,3-b]pyridin-5-yl)ethyl)-9-isopropyl-2-(pyridin-3-yl)-9H-purin-6-amine;

4-(2-(2-(5-fluoropyridin-3-yl)-9-(1-hydroxypropan-2-yl)-9H-purin-6-ylamino)ethyl)-2-methylphenol;

4-(2-(2-(benzo[b]thiophen-3-yl)-9-cyclohexyl-9H-purin-6-ylamino)ethyl)phenol;

4-(2-(9-isopropyl-2-(thiophen-3-yl)-9H-purin-6-ylamino)ethyl)phenol; and 1-(2-(2-(benzo[b]thiophen-3-yl)-6-(4-hydroxyphenethylamino)-9H-purin-9-yl)ethyl)pyrrolidin-2-one;

or a salt thereof.

21. The method of claim 16, wherein said compound is administered in the cell culture medium at a concentration between 100 pM and 1 μM.

22. The method of claim 17, wherein said starting cell population is cultured in presence of said compound from about 7 to 35 days.

* * * * *